United States Patent
Nilsson et al.

(10) Patent No.: US 11,897,869 B2
(45) Date of Patent: *Feb. 13, 2024

(54) JAK1 SELECTIVE INHIBITORS

(71) Applicant: AstraZeneca AB, Södertälje (SE)

(72) Inventors: Karl Magnus Nilsson, Mölndal (SE); Annika Birgitta Margareta Åstrand, Mölndal (SE); Anna Ingrid Kristina Berggren, Mölndal (SE); Johan R. Johansson, Mölndal (SE); Matti Juhani Lepistö, Mölndal (SE); Sameer Pralhad Kawatkar, Wilmington, DE (US); Qibin Su, Wilmington, DE (US); Jason Grant Kettle, Cambridge (GB)

(73) Assignee: AstaZeneca AB, Sodertalje (SE)

( * ) Notice: Subject to any disclaimer, the term of this patent is extended or adjusted under 35 U.S.C. 154(b) by 132 days.

This patent is subject to a terminal disclaimer.

(21) Appl. No.: 17/188,097

(22) Filed: Mar. 1, 2021

(65) Prior Publication Data

US 2021/0188821 A1 Jun. 24, 2021

Related U.S. Application Data

(63) Continuation of application No. 16/478,168, filed as application No. PCT/EP2018/051038 on Jan. 16, 2018, now Pat. No. 10,961,228.

(60) Provisional application No. 62/447,057, filed on Jan. 17, 2017.

(51) Int. Cl.
  *C07D 403/14* (2006.01)
  *A61P 17/14* (2006.01)
  *A61K 9/00* (2006.01)

(52) U.S. Cl.
  CPC ......... *C07D 403/14* (2013.01); *A61K 9/0075* (2013.01); *A61P 17/14* (2018.01)

(58) Field of Classification Search
  CPC ......... C07D 403/14; A61P 17/14; A61K 9/00
  See application file for complete search history.

(56) References Cited

U.S. PATENT DOCUMENTS 10,695,337 B2   6/2020   Huang et al.
10,961,228 B2 *  3/2021   Nilsson ............... A61P 37/00

FOREIGN PATENT DOCUMENTS

| CL | 201202501 A1 | 12/2012 | |
| WO | 2009046416 A1 | 4/2009 | |
| WO | WO 2009/046416 | * 4/2009 | ........... C07D 409/04 |
| WO | 2009118567 A2 | 10/2009 | |
| WO | 2017050938 A1 | 3/2017 | |

OTHER PUBLICATIONS

International Search Report and Written Opinion dated Mar. 21, 2018 for Application No. PCT/EP2018/051038.
International Preliminary Report on Patentability dated Aug. 1, 2019 for Application No. PCT/EP2018/051038.

* cited by examiner

*Primary Examiner* — Erich A Leeser

(57) ABSTRACT

Disclosed herein are compounds of Formula (I),

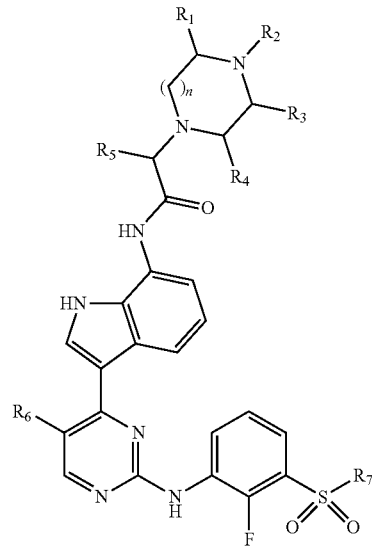

and pharmaceutically acceptable salts thereof, wherein $R_1$-$R_8$ have any of the meanings defined herein. Also disclosed are pharmaceutical compositions comprising compounds of Formula (I) and methods of using the same.

24 Claims, 3 Drawing Sheets

Specification includes a Sequence Listing.

JAK1 SELECTIVE INHIBITORS

BACKGROUND

The JAK (Janus-associated kinase) family includes four non-receptor tyrosine kinases, JAK1, JAK2, JAK3 and Tyk2, which play a critical role in cytokine and growth factor mediated signal transduction (Schindler C, and Darnell JE Jr., *Annu. Rev. Biochem.* 1995;64;621-651). The kinase JAK1 interacts with, among others, the receptors of type I interferon (e.g., IFNalpha), type II interferon (e.g., IFNgamma), the common gamma chain γc (e.g., IL-2, IL-4, IL-7, IL-9, IL-15 and IL-21), and the interleukin-6 family (IL-10, IL-13 and IL-22) (*N Engl J Med* 2013, 368, 161-170). After these cytokines bind to their receptors, receptor oligomerization occurs, resulting in the cytoplasmic tails of associated JAK kinases moving into proximity and facilitating the trans-phosphorylation and activation of tyrosine residues on the JAK kinase. Phosphorylated JAK kinases bind and activate various Signal Transducer and Activator of Transcription (STAT) proteins. These STAT proteins then dimerize and translocate to the nucleus where they function as both signalling molecules and transcription factors and ultimately bind to specific DNA sequences present in the promoters of cytokine-responsive genes (Leonard et al., (2000), *J. Allergy Clin. Immunol.* 105:877-888). Various immunodeficiency and autoimmune diseases such as allergies, asthma, alopecia areata, transplant (allograft) rejection, rheumatoid arthritis, amyotrophic lateral sclerosis and multiple sclerosis, and solid and hematologic cancers result from signalling disruption in the JAK/STAT pathway. See e.g., Frank, (1999), *Mol. Med.* 5:432-456 Vijayakriishnan et al, *Trends Pharmacol. Sci* 2011, 32, 25-34 and Flanagan et al,; *Open Rheumatol. J.* 2012, 6, 232-244; *N Engl J Med* 2013, 368, 161-170; *Exp. Dermatol.* 2014, 23, 7-11; *J. Med. Chem.* 2014, 57, 5023-5038, *J Allergy Clin Immunol* 2014; 133:1162-74, and *Expert Opin Orp Drug* (2015) 3 (4), 419-431.

An important element of JAK1 is the ability to pair with other JAK kinases at the intracellular domains of different subunits of the receptor. For example, JAK3 associates with the common gamma chain (γc) of the various cytokine receptors and pairs with JAK1 (*Immunol. Rev.* 2008, 223, 132-142). It has been indicated that JAK1 is dominant over JAK3, and inhibition of JAK1 is sufficient to inactivate signalling through the common gamma chain despite JAK3 activity (*Chem. Biol*. 2011, 18 (3), 314-323). Thus, selective inhibition of JAK1 may be sufficient to treat a number of inflammatory and autoimmune diseases associated with cytokine signalling via the JAK1/JAK3-STAT pathway. However, developing selective JAK1 inhibitors that have little to no off-target activity against other JAK kinases has been challenging. In particular, compounds identified as JAK1 selective inhibitors currently in clinical development exhibit only marginal JAK1 selectivity. (*Future Med. Chem.* (2015) 7(2), 203-235). For example, the reported JAK1/JAK2 selectivity ratios in biochemical assays for JAK1 inhibitors in active development for treatment of autoimmune diseases, such as Filgotinib (*J. Med. Chem.* 2014, 57, 9323-9342) and ABT-494 (WO2015061665-FIG. 1) are 2.8 based on $IC_{50}$ measured at approximately the Km of ATP. Thus, it is expected that those compounds will have some target activity against other JAK kinases and thus, additional side effects that could be limited with more selective JAK1 inhibitors. There is a need, therefore, to develop highly potent and selective JAK1 inhibitors to treat JAK1-related disorders, for instance, leukemia, lymphoma, transplant rejection (e.g., pancreas islet transplant rejection, bone marrow transplant applications (e.g., graft-versus-host disease), autoimmune diseases (e.g., Type 1 diabetes), and inflammation (e.g., asthma, allergic reactions), with no real or perceived side effects associated with off-target activity, such as anaemia.

SUMMARY

The present disclosure relates to novel compounds that possess selective JAK1 inhibition. Accordingly, provided herein are compounds of Formula (I):

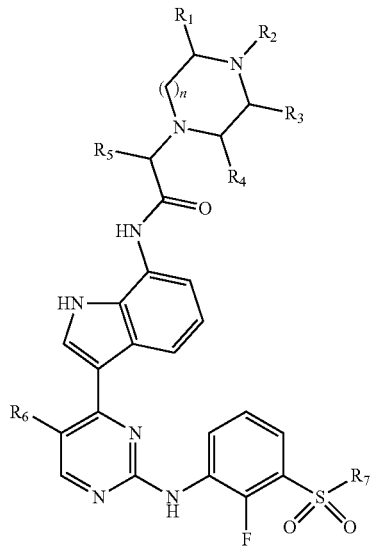

Formula (I)

wherein:
$R_1$, $R_3$, and $R_4$ are each individually chosen from hydrogen and methyl;
$R_2$ is chosen from hydrogen, methyl, and —$CH_2CH_2OH$;
n is 1 or 2;
$R_5$ is chosen from methyl, ethyl, and —$CH_2OR_8$;
$R_6$ is chosen from methyl, chlorine, and fluorine;
$R_7$ is selected from methyl, ethyl, and cyclopropyl; and
$R_8$ is selected from methyl, ethyl and benzyl;
or a pharmaceutically acceptable salt thereof.

The present disclosure also provides pharmaceutical compositions comprising a compound of Formula (I), or a pharmaceutically acceptable salt thereof, and a pharmaceutically acceptable diluent, excipient or carrier.

Also disclosed are methods of treating a JAK1-related disorder (e.g., Type 1 diabetes, lupus, multiple sclerosis, rheumatoid arthritis, psoriasis, asthma, atopic dermatitis, autoimmune thyroid disorders, ulcerative colitis, Crohn's disease, COPD, vitiligo, and alopecia areata) comprising administering to a subject an effective amount of a compound of Formula (I), or a pharmaceutically acceptable salt thereof. In another embodiment, disclosed is the use of a compound of Formula (I) for treating a JAK1-related disorder comprising administering to a subject an effective amount of a compound of Formula (I), or a pharmaceutically acceptable salt thereof. In another embodiment, disclosed is the use of a compound of Formula (I), or a pharmaceutically acceptable salt thereof, in the manufacture of a medicament or formulation for treating a JAK1-related disorder. In another embodiment, disclosed are pharmaceutical compositions comprising a compound of Formula (I), or a pharmaceutically acceptable salt thereof, for the treatment of a JAK1-related disorder.

Also disclosed are methods of inhibiting JAK1 in a subject comprising administering to a subject an effective amount of a compound of Formula (I), or a pharmaceutically acceptable salt thereof. In another embodiment, disclosed is the use of a compound of Formula (I), or a pharmaceutically acceptable salt thereof, for inhibiting JAK1 in a subject comprising administering to a subject an effective amount of a compound of Formula (I), or a pharmaceutically acceptable salt thereof. In another embodiment, disclosed is the use of a compound of Formula (I), or a pharmaceutically acceptable salt thereof, in the manufacture of a medicament or formulation for inhibiting JAK1 in a subject. In another embodiment, disclosed are pharmaceutical compositions comprising a compound of Formula (I), or a pharmaceutically acceptable salt thereof, for inhibiting JAK1 in a subject.

The present disclosure also provides processes and intermediates useful in the preparation of compounds of Formula (I).

DETAILED DESCRIPTION

Compounds

Figure 1:
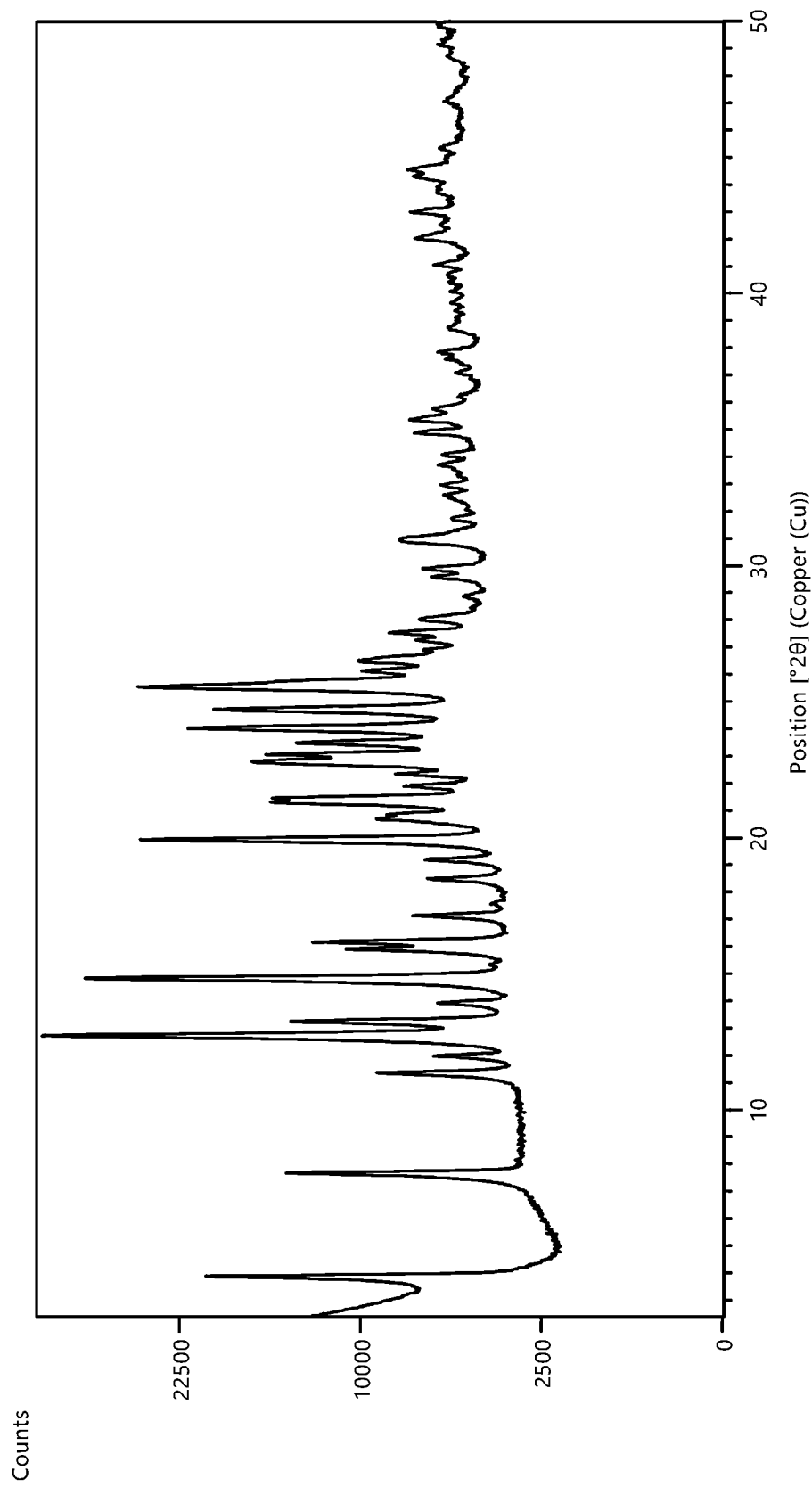
FIG. 1 illustrates the powder X-ray diffraction diagram of the crystalline form of the title compound listed for Example 35.

In one embodiment, disclosed are compounds of formula (I):

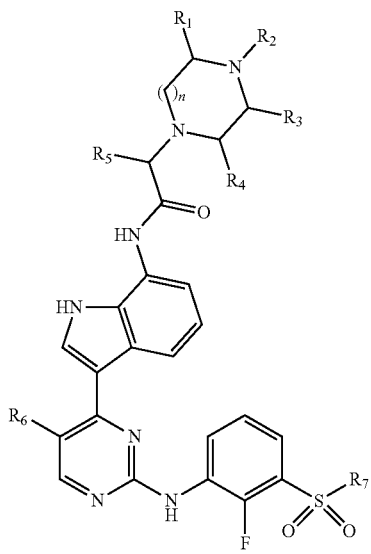

Formula (I)

wherein:
$R_1$, $R_3$, and $R_4$ are each individually chosen from hydrogen and methyl;
$R_2$ is chosen from hydrogen, methyl, and —$CH_2CH_2OH$;
n is 1 or 2;
$R_5$ is chosen from methyl, ethyl, and —$CH_2OR_8$;
$R_6$ is chosen from methyl, chlorine, and fluorine;
$R_7$ is selected from methyl, ethyl, and cyclopropyl; and
$R_8$ is selected from methyl, ethyl and benzyl;
or a pharmaceutically acceptable salt thereof.

In some embodiments, each of $R_1$-$R_4$ is chosen independently from hydrogen and methyl.
In some embodiments, $R_1$, $R_3$, and $R_4$ are all hydrogen.
In some embodiments, n is 1.
In some embodiments, $R_5$ is methyl or —$CH_2OR_8$.
In some embodiments, $R_6$ is methyl or fluorine.
In some embodiments, $R_7$ is methyl.
In some embodiments, $R_8$ is methyl.
In at least one embodiment, $R_1$, $R_3$ and $R_4$ are H; $R_2$ is methyl; $R_6$ is fluorine; $R_7$ is methyl; $R_5$ is —$CH_2OR_8$; and $R_8$ is methyl.

In one embodiment, the compounds of Formula (I) are compounds of Formula (Ia):

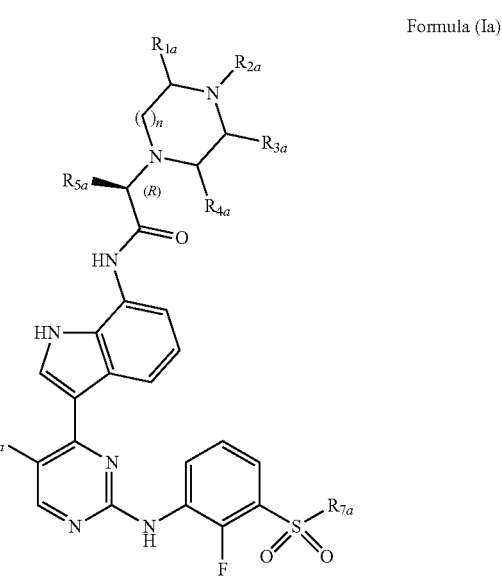

Formula (Ia)

wherein:
$R^{1a}$, $R_{3a}$, and $R_{4a}$ are each individually chosen from hydrogen and methyl;
$R_{2a}$ is chosen from hydrogen, methyl, and —$CH_2CH_2OH$;
n is 1 or 2;
$R_{5a}$ is chosen from methyl, ethyl, and —$CH_2OR_{8a}$;
$R_{6a}$ is chosen from methyl, chlorine, and fluorine;
$R_{7a}$ is selected from methyl, ethyl, and cyclopropyl; and
$R_{8a}$ is selected from methyl, ethyl and benzyl;
or a pharmaceutically acceptable salt thereof.

In some embodiments, each of $R_{1a}$-$R_{4a}$ is chosen independently from hydrogen and methyl.
In some embodiments, $R_{1a}$, $R_{3a}$, and $R_{4a}$ are all hydrogen.
In some embodiments, n is 1.
In some embodiments, $R_{5a}$ is methyl or —$CH_2OR_{8a}$.
In some embodiments, $R_{6a}$ is methyl or fluorine.
In some embodiments, $R_{7a}$ is methyl.
In some embodiments, $R_{8a}$ is methyl.
In at least one embodiment, $R_{1a}$, $R_{3a}$ and $R_{4a}$ are H; $R_{2a}$ is methyl; $R_{6a}$ is fluorine; $R_{7a}$ is methyl; $R_{5a}$ is —$CH_2OR_{8a}$; and $R_{8a}$ is methyl.

In one embodiment, the compounds of Formula (I) are compounds of Formula (Ib):

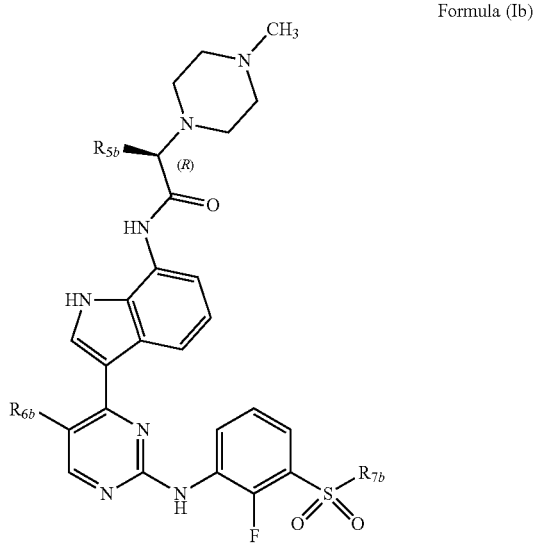

Formula (Ib)

wherein:
$R_{5b}$ is chosen from methyl, ethyl, and —$CH_2OR_{8b}$;
$R_{6b}$ is chosen from methyl, chlorine, and fluorine;
$R_{7b}$ is selected from methyl, ethyl, and cyclopropyl; and
$R_{8b}$ is selected from methyl, ethyl and benzyl;
or a pharmaceutically acceptable salt thereof.

In some embodiments, $R_{5b}$ is methyl or —$CH_2OR_{8b}$.
In some embodiments, $R_{6b}$ is methyl or fluorine.
In some embodiments, $R_{7b}$ is methyl.
In some embodiments, $R_{6b}$ is methyl.

In at least one embodiment, $R_{6b}$ is fluorine; $R_{7b}$ is methyl; $R_{5b}$ is —$CH_2OR_{8b}$; and $R_{8b}$ is methyl.

In some embodiments, disclosed are the compounds of Table 1, or a pharmaceutically salt thereof:

TABLE 1

| Example No. | Chemical Structure | Name |
|---|---|---|
| Ex. 1 | 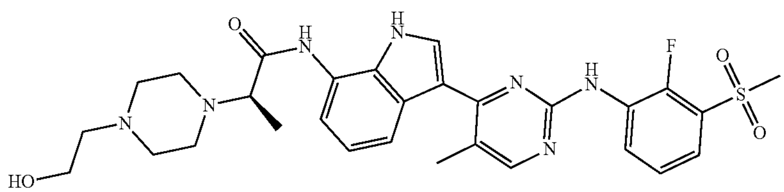 [SMILES: Cc1cnc(Nc2cccc(S(C)(=O)=O)c2F)nc1-c1c[nH]c2c(NC(=O)[C@@H](C)N3CCN(CCO)CC3)cccc12] | (R)-N-(3-(2-((2-fluoro-3-(methylsulfonyl)phenyl)amino)-5-methylpyrimidin-4-yl)-1H-indol-7-yl)-2-(4-(2-hydroxyethyl)piperazin-1-yl)propanamide |
| Ex. 2 | 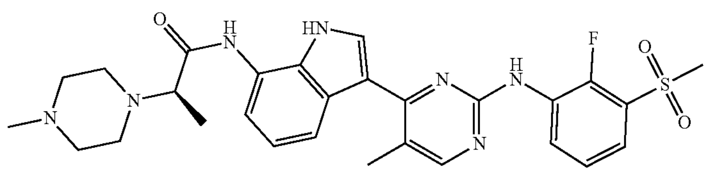 | (R)-N-(3-(2-(2-fluoro-3-(methylsulfonyl)phenylamino)-5-methylpyrimidin-4-yl)-1H-indol-7-yl)-2-(4-methylpiperazin-1-yl)propanamide |
| Ex. 3 | 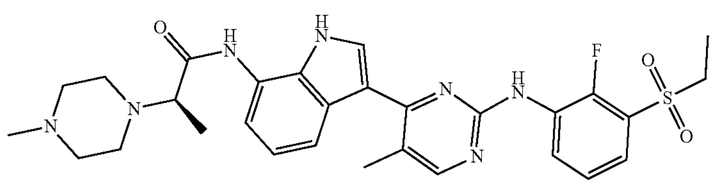 [SMILES: CCS(=O)(=O)c1cccc(Nc2ncc(C)c(-c3c[nH]c4c(NC(=O)[C@@H](C)N5CCN(C)CC5)cccc34)n2)c1F] | (R)-N-(3-(2-(3-(ethylsulfonyl)-2-fluorophenylamino)-5-methylpyrimidin-4-yl)-1H-indol-7-yl)-2-(4-methylpiperazin-1-yl)propanamide |
| Ex. 4 | 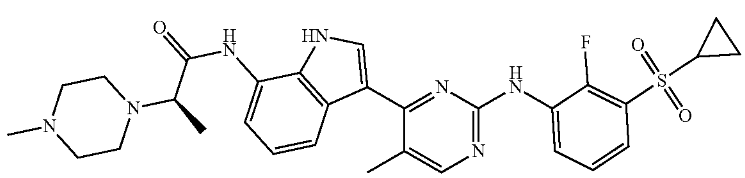 [SMILES: Cc1cnc(Nc2cccc(S(=O)(=O)C3CC3)c2F)nc1-c1c[nH]c2c(NC(=O)[C@@H](C)N3CCN(C)CC3)cccc12] | (R)-N-(3-(2-(3-(cyclopropylsulfonyl)-2-fluorophenylamino)-5-methylpyrimidin-4-yl)-1H-indol-7-yl)-2-(4-methylpiperazin-1-yl)propanamide |
| Ex. 5 | 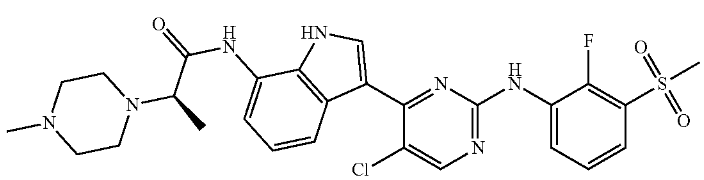 | (R)-N-(3-(5-chloro-2-((2-fluoro-3-(methylsulfonyl)phenyl)amino)pyrimidin-4-yl)-1H-indol-7-yl)-2-(4-methylpiperazin-1-yl)propanamide |

TABLE 1-continued

| Example No. | Chemical Structure | Name |
|---|---|---|
| Ex. 6 | 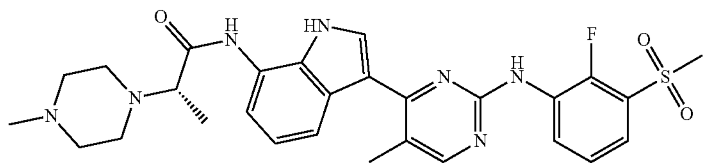 | (S)-N-(3-(2-((2-fluoro-3-(methylsulfonyl)phenyl)amino)-5-methylpyrimidin-4-yl)-1H-indol-7-yl)-2-(4-methylpiperazin-1-yl)propanamide |
| Ex. 7 | 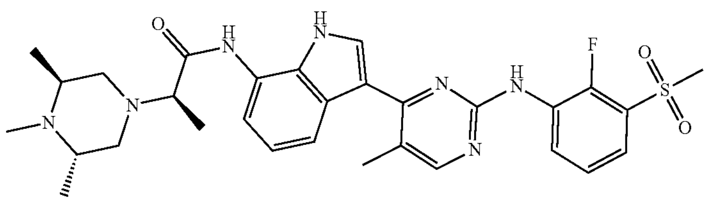 | (R)-N-(3-(2-((2-fluoro-3-(methylsulfonyl)phenyl)amino)-5-methylpyrimidin-4-yl)-1H-indol-7-yl)-2-((3S,5S)-3,4,5-trimethylpiperazin-1-yl)propanamide |
| Ex. 8 | 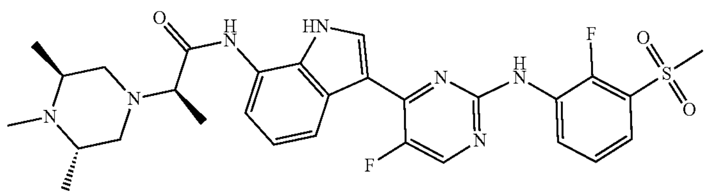 | (R)-N-(3-(5-fluoro-2-((2-fluoro-3-(methylsulfonyl)phenyl)amino)pyrimidin-4-yl)-1H-indol-7-yl)-2-((3S,5S)-3,4,5-trimethylpiperazin-1-yl)propanamide |
| Ex. 9 | 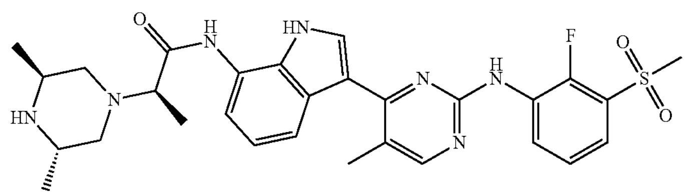 | (R)-2-((3S,5S)-3,5-dimethylpiperazin-1-yl)-N-(3-(2-((2-fluoro-3-(methylsulfonyl)phenyl)amino)-5-methylpyrimidin-4-yl)-1H-indol-7-yl)propanamide |
| Ex. 10 | 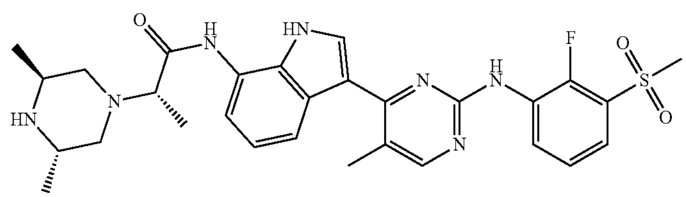 | (S)-2-((3S,5S)-3,5-dimethylpiperazin-1-yl)-N-(3-(2-((2-fluoro-3-(methylsulfonyl)phenyl)amino)-5-methylpyrimidin-4-yl)-1H-indol-7-yl)propanamide |
| Ex. 11 | 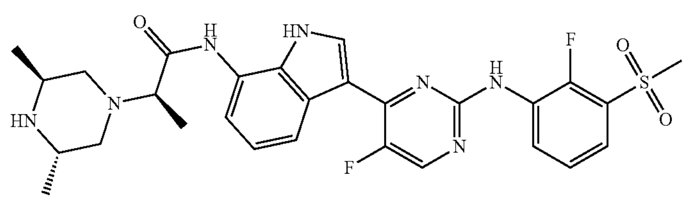 | (R)-2-((3S,5S)-3,5-dimethylpiperazin-1-yl)-N-(3-(5-fluoro-2-((2-fluoro-3-(methylsulfonyl)phenyl)amino)pyrimidin-4-yl)-1H-indol-7-yl)propanamide |
| Ex. 12 | 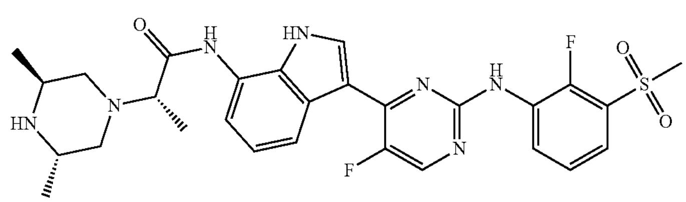 | (S)-2-((3S,5S)-3,5-dimethylpiperazin-1-yl)-N-(3-(5-fluoro-2-((2-fluoro-3-(methylsulfonyl)phenyl)amino)pyrimidin-4-yl)-1H-indol-7-yl)propanamide |

TABLE 1-continued

| Example No. | Chemical Structure | Name |
|---|---|---|
| Ex. 13 | 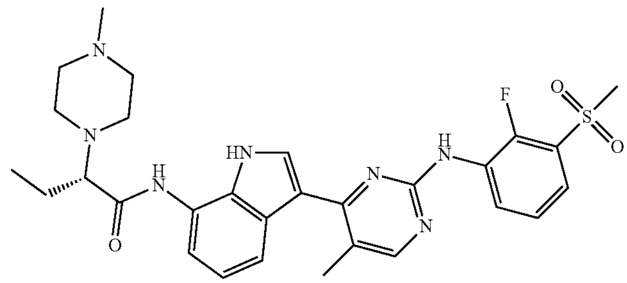 [SMILES: CC[C@@H](C(=O)Nc1cccc2c(-c3nc(Nc4cccc(S(C)(=O)=O)c4F)ncc3C)c[nH]c12)N1CCN(C)CC1] | (S)-N-(3-(2-((2-fluoro-3-(methylsulfonyl)phenyl)amino)-5-methylpyrimidin-4-yl)-1H-indol-7-yl)-2-(4-methylpiperazin-1-yl)butanamide |
| Ex. 14 | 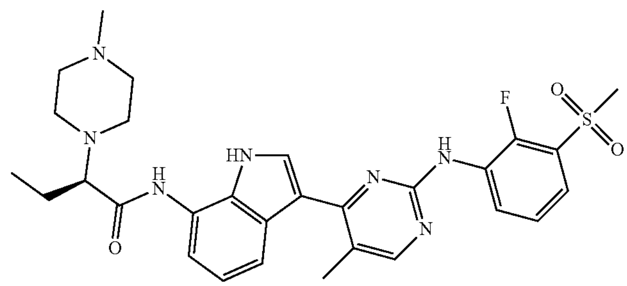 [SMILES: CC[C@H](C(=O)Nc1cccc2c(-c3nc(Nc4cccc(S(C)(=O)=O)c4F)ncc3C)c[nH]c12)N1CCN(C)CC1] | (R)-N-(3-(2-((2-fluoro-3-(methylsulfonyl)phenyl)amino)-5-methylpyrimidin-4-yl)-1H-indol-7-yl)-2-(4-methylpiperazin-1-yl)butanamide |
| Ex. 15 | 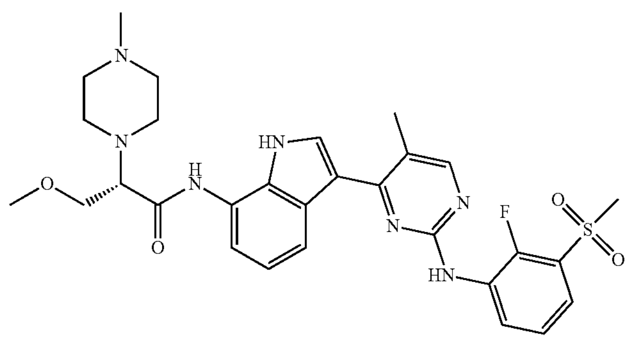 | (S)-N-(3-(2-((2-fluoro-3-(methylsulfonyl)phenyl)amino)-5-methylpyrimidin-4-yl)-1H-indol-7-yl)-3-methoxy-2-(4-methylpiperazin-1-yl)propanamide |
| Ex. 16 | 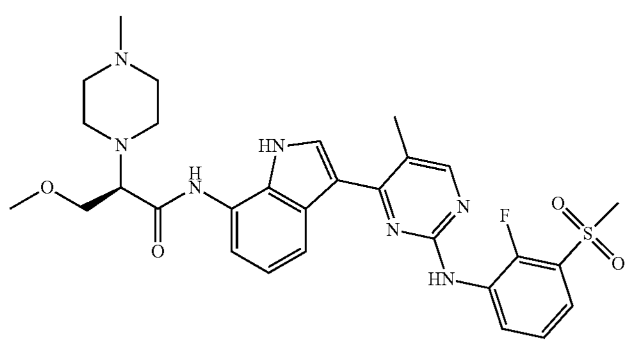 | (R)-N-(3-(2-((2-fluoro-3-(methylsulfonyl)phenyl)amino)-5-methylpyrimidin-4-yl)-1H-indol-7-yl)-3-methoxy-2-(4-methylpiperazin-1-yl)propanamide |
| Ex. 17 | 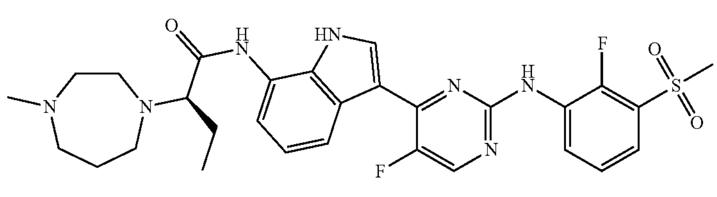 | (R)-N-(3-(5-fluoro-2-((2-fluoro-3-(methylsulfonyl)phenyl)amino)pyrimidin-4-yl)-1H-indol-7-yl)-2-(4-methyl-1,4-diazepan-1-yl)butanamide |

TABLE 1-continued

| Example No. | Chemical Structure | Name |
|---|---|---|
| Ex. 18 | 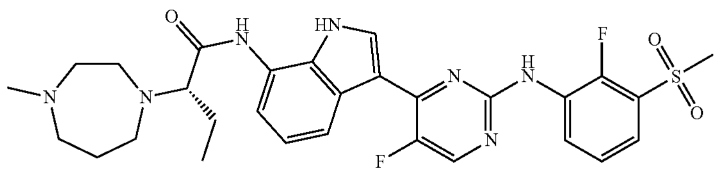 | (S)-N-(3-(5-fluoro-2-((2-fluoro-3-(methylsulfonyl)phenyl)amino)pyrimidin-4-yl)-1H-indol-7-yl)-2-(4-methyl-1,4-diazepan-1-yl)butanamide |
| Ex. 19 | 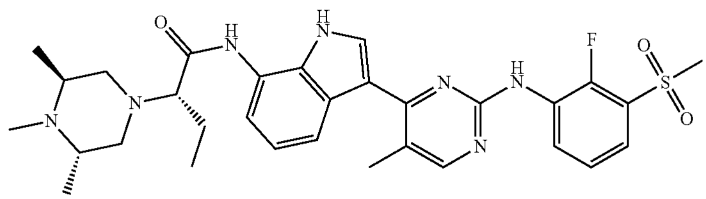 | (S)-N-(3-(2-((2-fluoro-3-(methylsulfonyl)phenyl)amino)-5-methylpyrimidin-4-yl)-1H-indol-7-yl)-2-((3S,5S)-3,4,5-trimethylpiperazin-1-yl)butanamide |
| Ex. 20 | 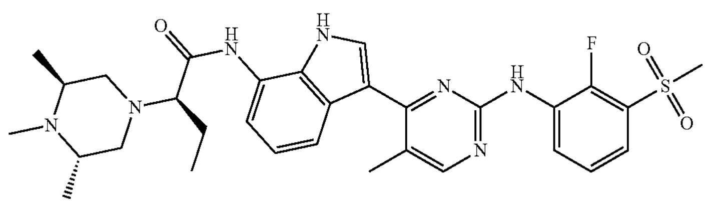 | (R)-N-(3-(2-((2-fluoro-3-(methylsulfonyl)phenyl)amino)-5-methylpyrimidin-4-yl)-1H-indol-7-yl)-2-((3S,5S)-3,4,5-trimethylpiperazin-1-yl)butanamide |
| Ex. 21 | 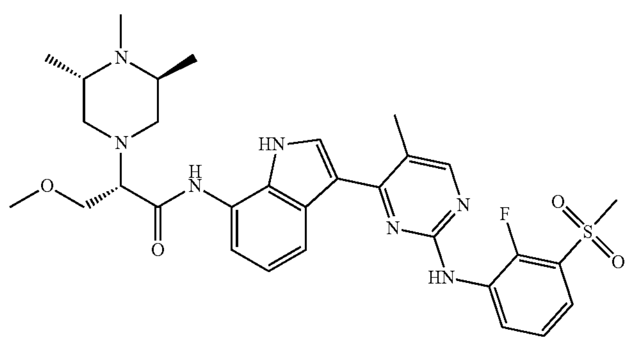 [SMILES: COC[C@@H](C(=O)Nc1cccc2c(-c3nc(Nc4cccc(S(C)(=O)=O)c4F)ncc3C)c[nH]c12)N1C[C@H](C)N(C)[C@@H](C)C1] | (S)-N-(3-(2-((2-fluoro-3-(methylsulfonyl)phenyl)amino)-5-methylpyrimidin-4-yl)-1H-indol-7-yl)-3-methoxy-2-((3S,5S)-3,4,5-trimethylpiperazin-1-yl)propanamide |
| Ex. 22 | 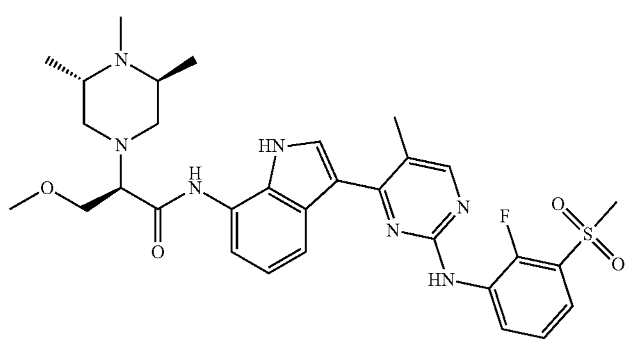 [SMILES: COC[C@H](C(=O)Nc1cccc2c(-c3nc(Nc4cccc(S(C)(=O)=O)c4F)ncc3C)c[nH]c12)N1C[C@H](C)N(C)[C@@H](C)C1] | (R)-N-(3-(2-((2-fluoro-3-(methylsulfonyl)phenyl)amino)-5-methylpyrimidin-4-yl)-1H-indol-7-yl)-3-methoxy-2-((3S,5S)-3,4,5-trimethylpiperazin-1-yl)propanamide |
| Ex. 23 | 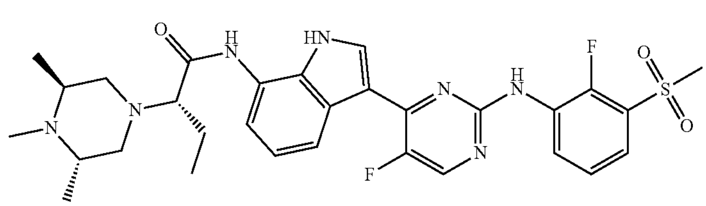 | (S)-N-(3-(5-fluoro-2-(2-fluoro-3-(methylsulfonyl)phenylamino)pyrimidin-4-yl)-1H-indol-7-yl)-2-((3S,5S)-3,4,5-trimethylpiperazin-1-yl)butanamide |

TABLE 1-continued

| Example No. | Chemical Structure | Name |
|---|---|---|
| Ex. 24 | 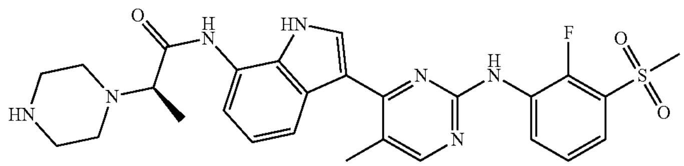 [SMILES: Cc1cnc(Nc2cccc(S(C)(=O)=O)c2F)nc1-c1c[nH]c2c(NC(=O)[C@@H](C)N3CCNCC3)cccc12] | (R)-N-(3-(2-((2-fluoro-3-(methylsulfonyl)phenyl)amino)-5-methylpyrimidin-4-yl)-1H-indol-7-yl)-2-(piperazin-1-yl)propanamide |
| Ex. 25 | 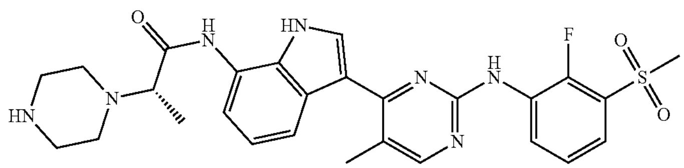 [SMILES: Cc1cnc(Nc2cccc(S(C)(=O)=O)c2F)nc1-c1c[nH]c2c(NC(=O)[C@H](C)N3CCNCC3)cccc12] | (S)-N-(3-(2-((2-fluoro-3-(methylsulfonyl)phenyl)amino)-5-methylpyrimidin-4-yl)-1H-indol-7-yl)-2-(piperazin-1-yl)propanamide |
| Ex. 26 | 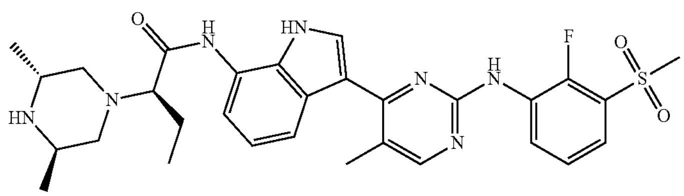 | (R)-2-((3R,5R)-3,5-dimethylpiperazin-1-yl)-N-(3-(2-((2-fluoro-3-(methylsulfonyl)phenyl)amino)-5-methylpyrimidin-4-yl)-1H-indol-7-yl)butanamide |
| Ex. 27 | 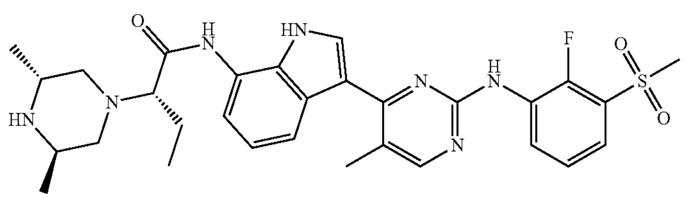 | (S)-2-((3R,5R)-3,5-dimethylpiperazin-1-yl)-N-(3-(2-((2-fluoro-3-(methylsulfonyl)phenyl)amino)-5-methylpyrimidin-4-yl)-1H-indol-7-yl)butanamide |
| Ex. 28 | 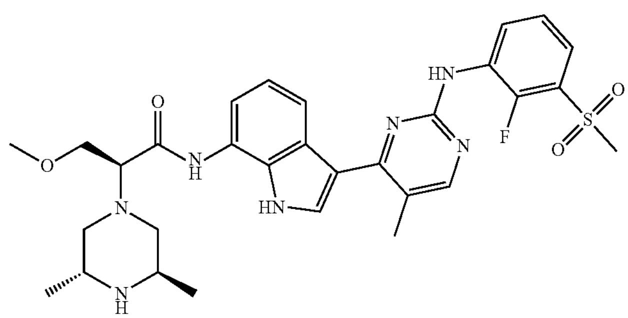 [SMILES: COC[C@@H](C(=O)Nc1cccc2c(-c3nc(Nc4cccc(S(C)(=O)=O)c4F)ncc3C)c[nH]c12)N1C[C@@H](C)N[C@H](C)C1] | (S)-2-((3R,5R)-3,5-dimethylpiperazin-1-yl)-N-(3-(2-((2-fluoro-3-(methylsulfonyl)phenyl)amino)-5-methylpyrimidin-4-yl)-1H-indol-7-yl)-3-methoxypropanamide |
| Ex. 29 | 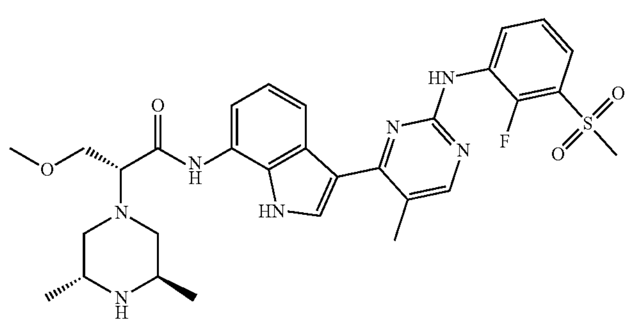 [SMILES: COC[C@H](C(=O)Nc1cccc2c(-c3nc(Nc4cccc(S(C)(=O)=O)c4F)ncc3C)c[nH]c12)N1C[C@@H](C)N[C@H](C)C1] | (R)-2-((3R,5R)-3,5-dimethylpiperazin-1-yl)-N-(3-(2-((2-fluoro-3-(methylsulfonyl)phenyl)amino)-5-methylpyrimidin-4-yl)-1H-indol-7-yl)-3-methoxypropanamide |
| Ex. 30 | 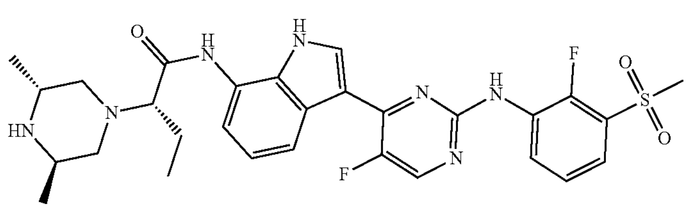 | (S)-2-((3R,5R)-3,5-dimethylpiperazin-1-yl)-N-(3-(5-fluoro-2-((2-fluoro-3-(methylsulfonyl)phenyl)amino)pyrimidin-4-yl)-1H-indol-7-yl)butanamide |

TABLE 1-continued

| Example No. | Chemical Structure | Name |
|---|---|---|
| Ex. 31 | 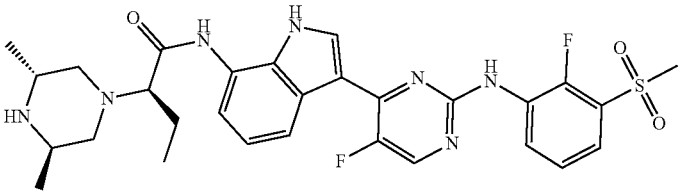 | (R)-2-((3R,5R)-3,5-dimethylpiperazin-1-yl)-N-(3-(5-fluoro-2-((2-fluoro-3-(methylsulfonyl)phenyl)amino)pyrimidin-4-yl)-1H-indol-7-yl)butanamide |
| Ex. 32 | 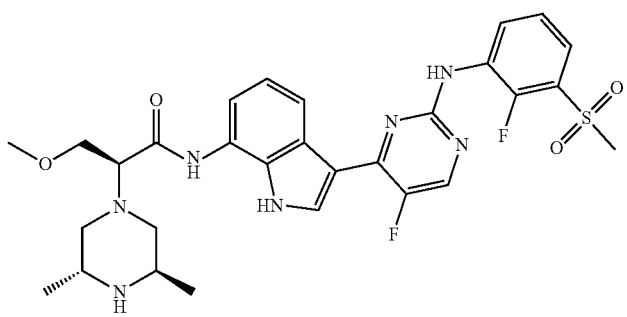 [SMILES: COC[C@@H](C(=O)Nc1cccc2c(-c3nc(Nc4cccc(S(C)(=O)=O)c4F)ncc3F)c[nH]c12)N1C[C@@H](C)N[C@H](C)C1] | (S)-2-((3R,5R)-3,5-dimethylpiperazin-1-yl)-N-(3-(5-fluoro-2-((2-fluoro-3-(methylsulfonyl)phenyl)amino)pyrimidin-4-yl)-1H-indol-7-yl)-3-methoxypropanamide |
| Ex. 33 | 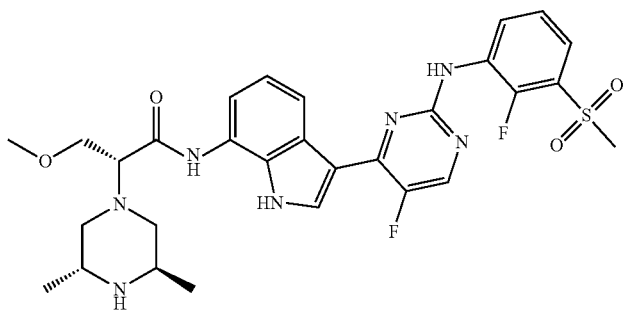 | (R)-2-((3R,5R)-3,5-dimethylpiperazin-1-yl)-N-(3-(5-fluoro-2-((2-fluoro-3-(methylsulfonyl)phenyl)amino)pyrimidin-4-yl)-1H-indol-7-yl)-3-methoxypropanamide |
| Ex. 34 | 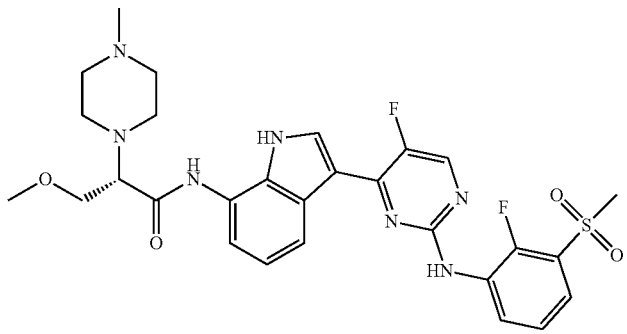 | (S)-N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide |
| Ex. 35 | 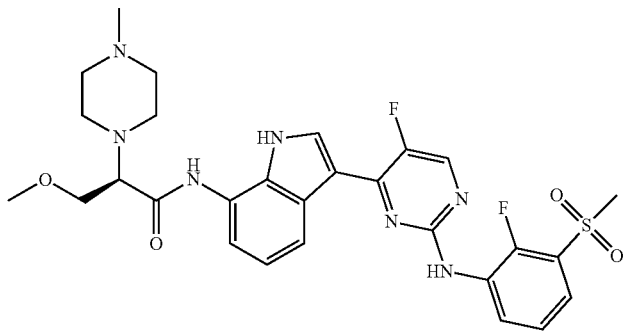 | (R)-N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide |

TABLE 1-continued

| Example No. | Chemical Structure | Name |
|---|---|---|
| Ex. 36 | 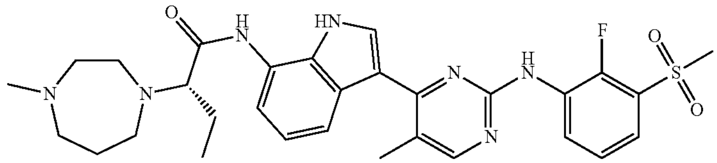 | (S)-N-(3-(2-((2-fluoro-3-(methylsulfonyl)phenyl)amino)-5-methylpyrimidin-4-yl)-1H-indol-7-yl)-2-(4-methyl-1,4-diazepan-1-yl)butanamide |
| Ex. 37 | 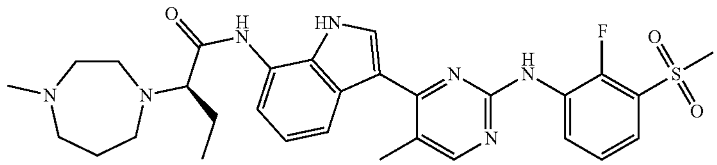 | (R)-N-(3-(2-((2-fluoro-3-(methylsulfonyl)phenyl)amino)-5-methylpyrimidin-4-yl)-1H-indol-7-yl)-2-(4-methyl-1,4-diazepan-1-yl)butanamide |
| Ex. 38 | 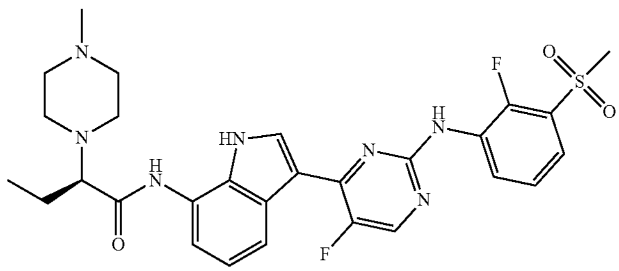 [SMILES: CC[C@H](C(=O)Nc1cccc2c(-c3nc(Nc4cccc(S(C)(=O)=O)c4F)ncc3F)c[nH]c12)N1CCN(C)CC1] | (R)-N-(3-(5-fluoro-2-((2-fluoro-3-(methylsulfonyl)phenyl)amino)pyrimidin-4-yl)-1H-indol-7-yl)-2-(4-methylpiperazin-1-yl)butanamide |
| Ex. 39 | 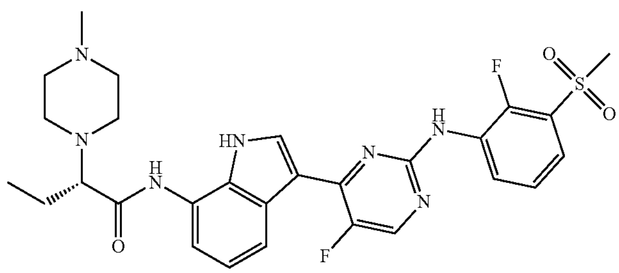 [SMILES: CC[C@@H](C(=O)Nc1cccc2c(-c3nc(Nc4cccc(S(C)(=O)=O)c4F)ncc3F)c[nH]c12)N1CCN(C)CC1] | (S)-N-(3-(5-fluoro-2-((2-fluoro-3-(methylsulfonyl)phenyl)amino)pyrimidin-4-yl)-1H-indol-7-yl)-2-(4-methylpiperazin-1-yl)butanamide |
| Ex. 40 | 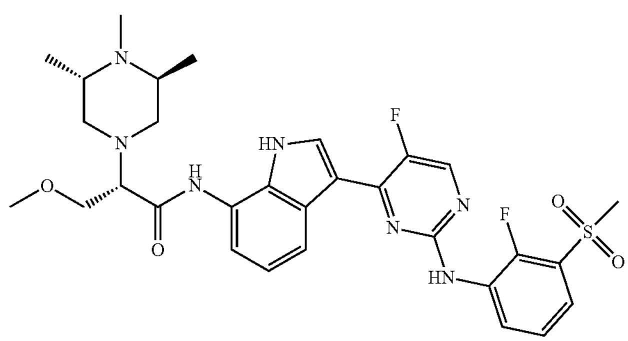 | (S)-N-(3-(5-fluoro-2-((2-fluoro-3-(methylsulfonyl)phenyl)amino)pyrimidin-4-yl)-1H-indol-7-yl)-3-methoxy-2-((3S,5S)-3,4,5-trimethylpiperazin-1-yl)propanamide |
| Ex. 41 | 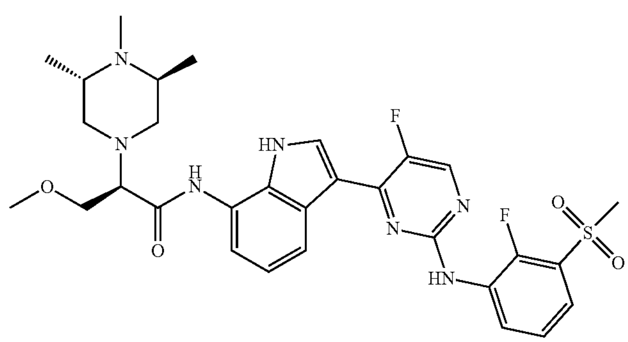 | (R)-N-(3-(5-fluoro-2-((2-fluoro-3-(methylsulfonyl)phenyl)amino)pyrimidin-4-yl)-1H-indol-7-yl)-3-methoxy-2-((3S,5S)-3,4,5-trimethylpiperazin-1-yl)propanamide |

TABLE 1-continued

| Example No. | Chemical Structure | Name |
|---|---|---|
| Ex. 42 | 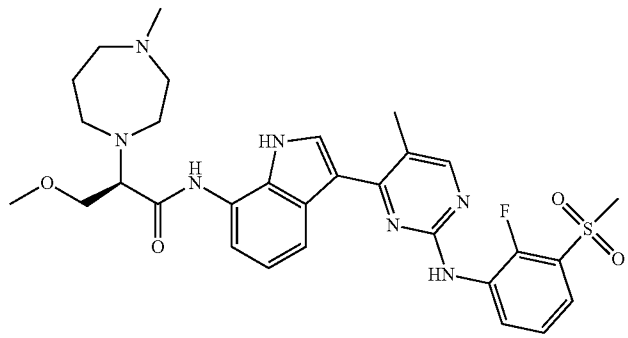 | (R)-N-(3-(2-((2-fluoro-3-(methylsulfonyl)phenyl)amino)-5-methylpyrimidin-4-yl)-1H-indol-7-yl)-3-methoxy-2-(4-methyl-1,4-diazepan-1-yl)propanamide |
| Ex. 43 | 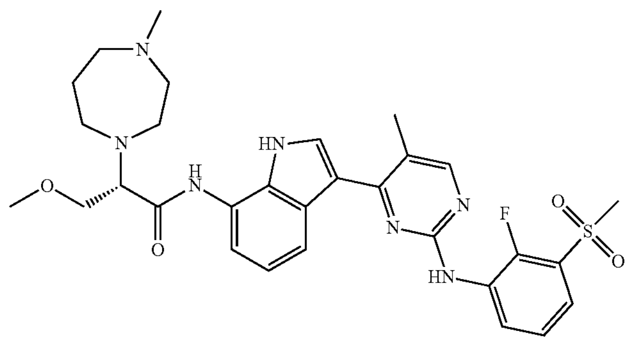 | (S)-N-(3-(2-((2-fluoro-3-(methylsulfonyl)phenyl)amino)-5-methylpyrimidin-4-yl)-1H-indol-7-yl)-3-methoxy-2-(4-methyl-1,4-diazepan-1-yl)propanamide |
| Ex. 44 | 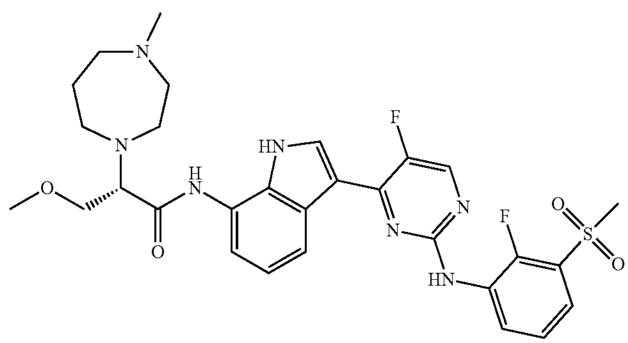 | (S)-N-(3-(5-fluoro-2-((2-fluoro-3-(methylsulfonyl)phenyl)amino)pyrimidin-4-yl)-1H-indol-7-yl)-3-methoxy-2-(4-methyl-1,4-diazepan-1-yl)propanamide |
| Ex. 45 | 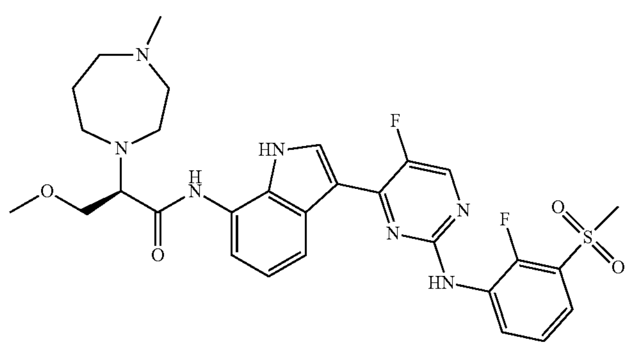 | (R)-N-(3-(5-fluoro-2-((2-fluoro-3-(methylsulfonyl)phenyl)amino)pyrimidin-4-yl)-1H-indol-7-yl)-3-methoxy-2-(4-methyl-1,4-diazepan-1-yl)propanamide |
| Ex. 46 | 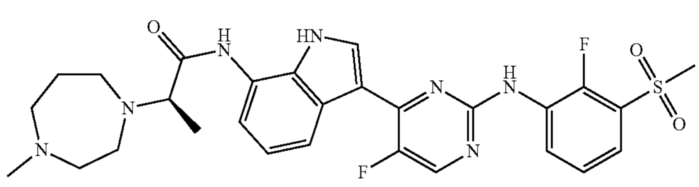 | (R)-N-(3-(5-fluoro-2-((2-fluoro-3-(methylsulfonyl)phenyl)amino)pyrimidin-4-yl)-1H-indol-7-yl)-2-(4-methyl-1,4-diazepan-1-yl)propanamide |

TABLE 1-continued

| Example No. | Chemical Structure | Name |
|---|---|---|
| Ex. 47 | 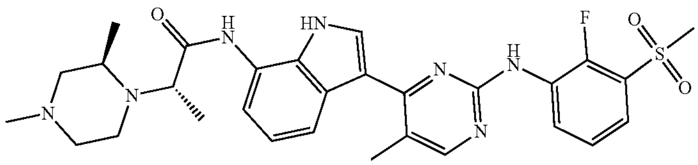 | (S)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)propanamide |
| Ex. 48 | 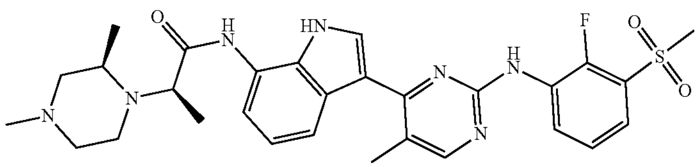 | (R)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)propanamide |
| Ex. 49 | 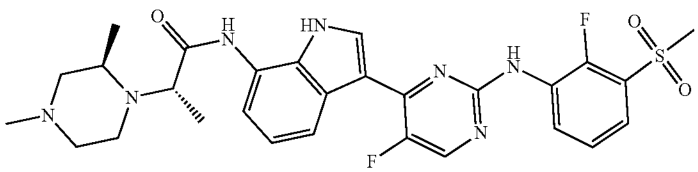 | (R)-2-((R)-2,4-dimethylpiperazin-1-yl)-N-(3-(5-fluoro-2-((2-fluoro-3-(methylsulfonyl)phenyl)amino)pyrimidin-4-yl)-1H-indol-7-yl)propanamide |
| Ex. 50 | 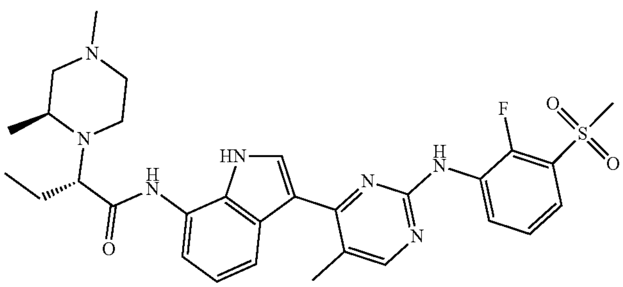 [SMILES: CC[C@@H](C(=O)Nc1cccc2c(-c3nc(Nc4cccc(S(C)(=O)=O)c4F)ncc3C)c[nH]c12)N1CCN(C)C[C@@H]1C] | (S)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide |
| Ex. 51 | 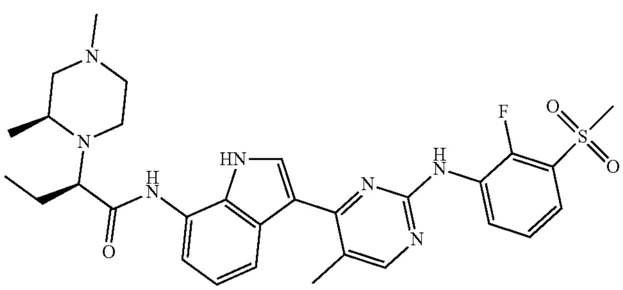 [SMILES: CC[C@H](C(=O)Nc1cccc2c(-c3nc(Nc4cccc(S(C)(=O)=O)c4F)ncc3C)c[nH]c12)N1CCN(C)C[C@@H]1C] | (R)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide |
| Ex. 52 | 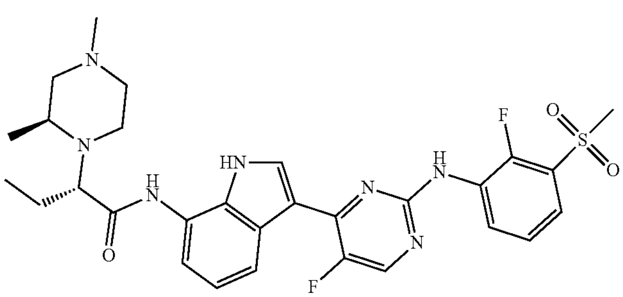 [SMILES: CC[C@@H](C(=O)Nc1cccc2c(-c3nc(Nc4cccc(S(C)(=O)=O)c4F)ncc3F)c[nH]c12)N1CCN(C)C[C@@H]1C] | (S)-2-((R)-2,4-dimethylpiperazin-1-yl)-N-(3-(5-fluoro-2-((2-fluoro-3-(methylsulfonyl)phenyl)amino)pyrimidin-4-yl)-1H-indol-7-yl)butanamide |

TABLE 1-continued

| Example No. | Chemical Structure | Name |
|---|---|---|
| Ex. 53 | 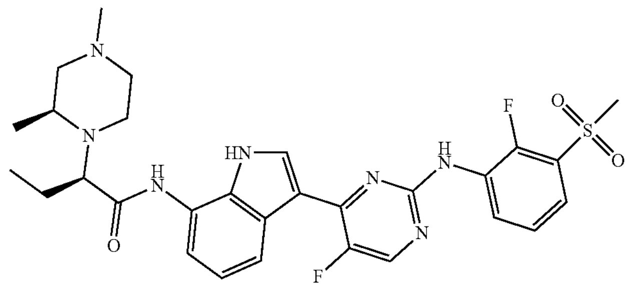 [SMILES: CC[C@H](C(=O)Nc1cccc2c(-c3nc(Nc4cccc(S(C)(=O)=O)c4F)ncc3F)c[nH]c12)N1CCN(C)C[C@@H]1C] | (R)-2-((R)-2,4-dimethylpiperazin-1-yl)-N-(3-(5-fluoro-2-((2-fluoro-3-(methylsulfonyl)phenyl)amino)pyrimidin-4-yl)-1H-indol-7-yl)butanamide |
| Ex. 54 | 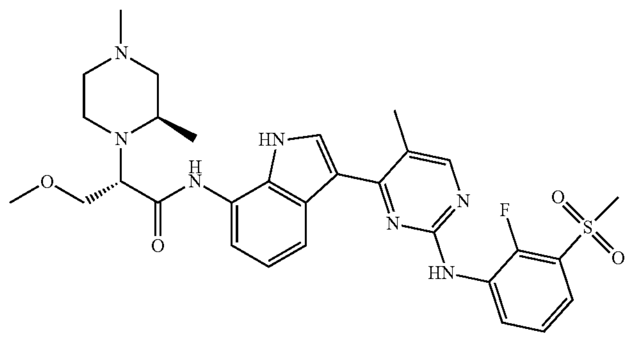 | (S)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)-3-methoxypropanamide |
| Ex. 55 | 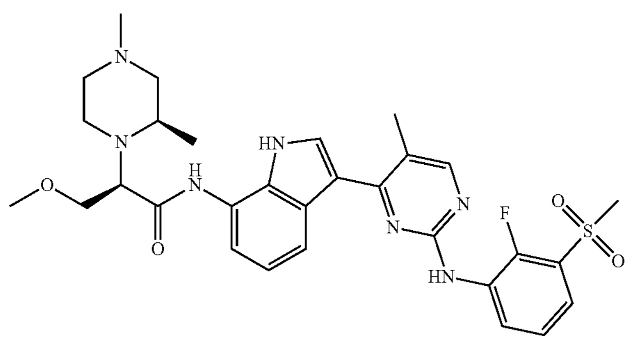 | (R)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)-3-methoxypropanamide |
| Ex. 56 | 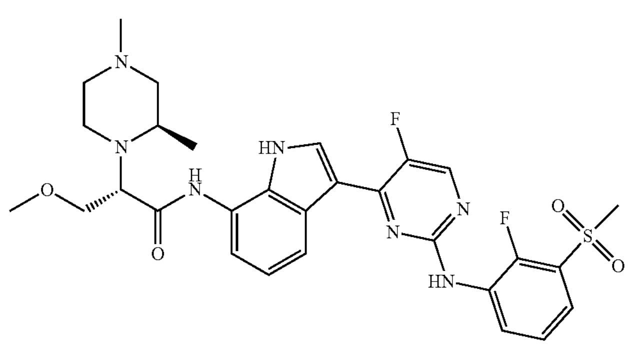 | (S)-2-((R)-2,4-dimethylpiperazin-1-yl)-N-(3-(5-fluoro-2-((2-fluoro-3-(methylsulfonyl)phenyl)amino)pyrimidin-4-yl)-1H-indol-7-yl)-3-methoxypropanamide |

TABLE 1-continued

| Example No. | Chemical Structure | Name |
|---|---|---|
| Ex. 57 | 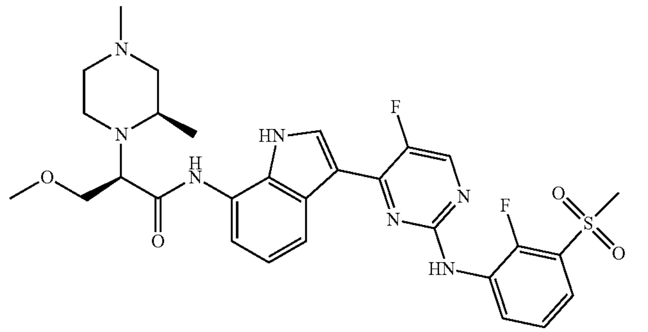 | (R)-2-((R)-2,4-dimethylpiperazin-1-yl)-N-(3-(5-fluoro-2-((2-fluoro-3-(methylsulfonyl)phenyl)amino)pyrimidin-4-yl)-1H-indol-7-yl)-3-methoxypropanamide |
| Ex. 58 | 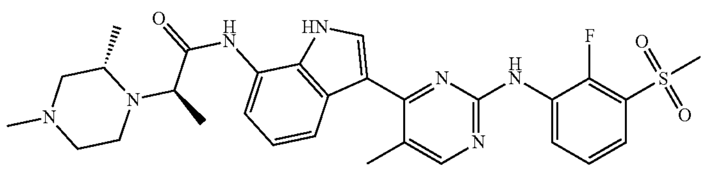 | (R)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)propanamide |
| Ex. 59 | 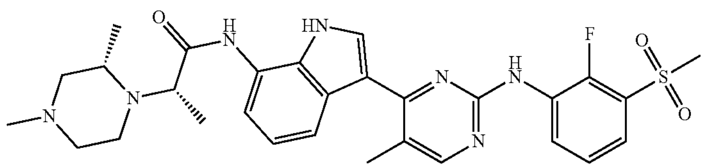 | (S)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)propanamide |
| Ex. 60 | 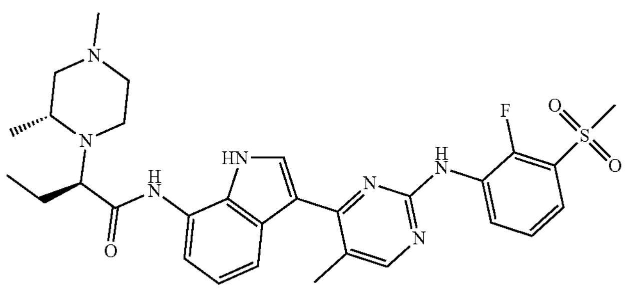 [SMILES: CC[C@H](C(=O)Nc1cccc2c(-c3nc(Nc4cccc(S(C)(=O)=O)c4F)ncc3C)c[nH]c12)N1CCN(C)C[C@H]1C] | (R)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide |
| Ex. 61 | 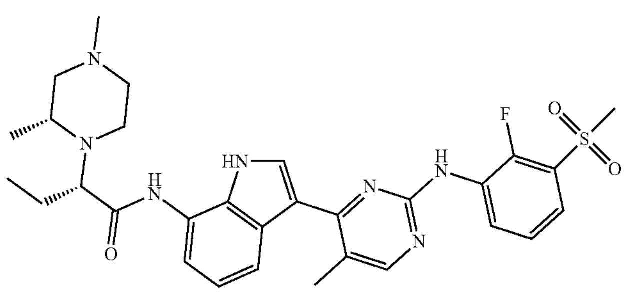 [SMILES: CC[C@@H](C(=O)Nc1cccc2c(-c3nc(Nc4cccc(S(C)(=O)=O)c4F)ncc3C)c[nH]c12)N1CCN(C)C[C@H]1C] | (S)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide |
| Ex. 62 | 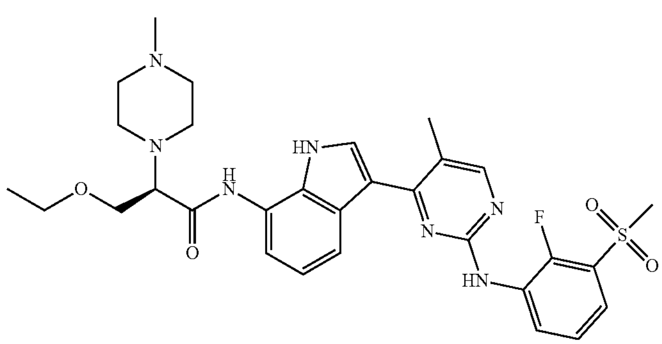 [SMILES: CCOC[C@H](C(=O)Nc1cccc2c(-c3nc(Nc4cccc(S(C)(=O)=O)c4F)ncc3C)c[nH]c12)N1CCN(C)CC1] | (R)-3-ethoxy-N-(3-(2-((2-fluoro-3-(methylsulfonyl)phenyl)amino)-5-methylpyrimidin-4-yl)-1H-indol-7-yl)-2-(4-methylpiperazin-1-yl)propanamide |

TABLE 1-continued

| Example No. | Chemical Structure | Name |
|---|---|---|
| Ex. 63 | 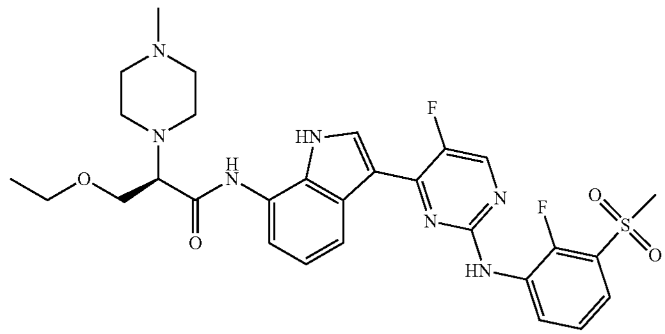 [SMILES: CCOC[C@H](C(=O)Nc1cccc2c(-c3nc(Nc4cccc(S(C)(=O)=O)c4F)ncc3F)c[nH]c12)N1CCN(C)CC1] | (R)-3-ethoxy-N-(3-(5-fluoro-2-((2-fluoro-3-(methylsulfonyl)phenyl)amino)pyrimidin-4-yl)-1H-indol-7-yl)-2-(4-methylpiperazin-1-yl)propanamide |
| Ex. 64 | 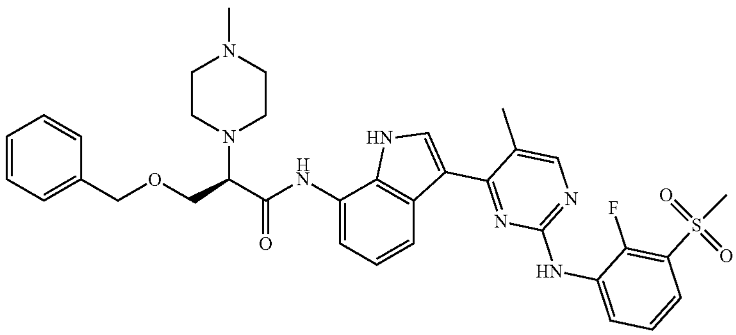 [SMILES: Cc1cnc(Nc2cccc(S(C)(=O)=O)c2F)nc1-c1c[nH]c2c(NC(=O)[C@@H](COCc3ccccc3)N3CCN(C)CC3)cccc12] | (R)-3-(benzyloxy)-N-(3-(2-((2-fluoro-3-(methylsulfonyl)phenyl)amino)-5-methylpyrimidin-4-yl)-1H-indol-7-yl)-2-(4-methylpiperazin-1-yl)propanamide |
| Ex. 65 | 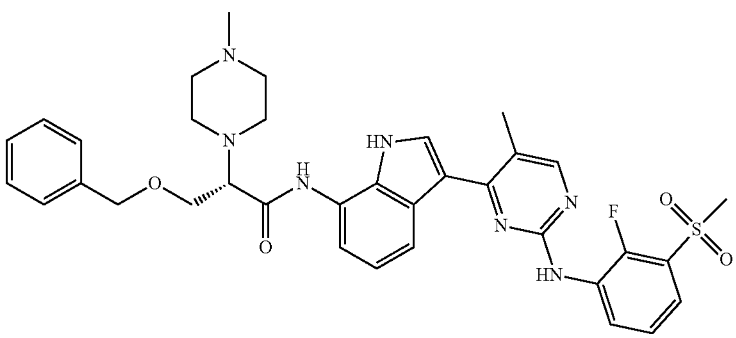 [SMILES: Cc1cnc(Nc2cccc(S(C)(=O)=O)c2F)nc1-c1c[nH]c2c(NC(=O)[C@H](COCc3ccccc3)N3CCN(C)CC3)cccc12] | (S)-3-(benzyloxy)-N-(3-(2-((2-fluoro-3-(methylsulfonyl)phenyl)amino)-5-methylpyrimidin-4-yl)-1H-indol-7-yl)-2-(4-methylpiperazin-1-yl)propanamide |
| Ex. 66 | 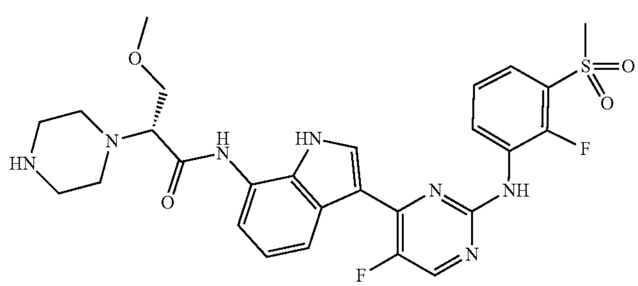 [SMILES: COC[C@H](C(=O)Nc1cccc2c(-c3nc(Nc4cccc(S(C)(=O)=O)c4F)ncc3F)c[nH]c12)N1CCNCC1] | (R)-N-(3-(5-fluoro-2-(2-fluoro-3-(methylsulfonyl)phenylamino)pyrimidin-4-yl)-1H-indol-7-yl)-3-methoxy-2-(piperazin-1-yl)propanamide |
| Ex. 67 | 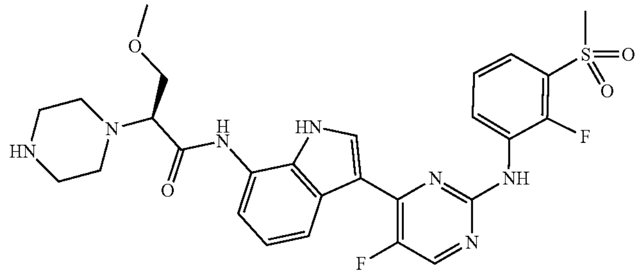 [SMILES: COC[C@@H](C(=O)Nc1cccc2c(-c3nc(Nc4cccc(S(C)(=O)=O)c4F)ncc3F)c[nH]c12)N1CCNCC1] | (S)-N-(3-(5-fluoro-2-(2-fluoro-3-(methylsulfonyl)phenylamino)pyrimidin-4-yl)-1H-indol-7-yl)-3-methoxy-2-(piperazin-1-yl)propanamide |

The disclosed compounds of Formula (I), (Ia), (Ib), or Table 1 may be prepared using the methods and processes described herein. In one aspect, the disclosed compounds of Formula (I), (Ia), (Ib), or Table 1 are prepared according to the processes described in the Examples.

Compounds of Formula (I), (Ia), (Ib), or Table 1 are capable of existing in various stereoisomeric forms and the present disclosure relates to each of the stereoisomeric forms that may exist for each compound and to mixtures thereof including racemates. It is understood that a substituent may be attached at a chiral center of a carbon atom and, therefore, the disclosed compounds include enantiomers, diastereomers and racemates. The term "enantiomer" includes pairs of stereoisomers that are non-superimposable mirror images of each other. A 1:1 mixture of a pair of enantiomers is a racemic mixture. The term is used to designate a racemic mixture where appropriate. The terms "diastereomers" or "diastereoisomers" include stereoisomers that have at least two asymmetric atoms, but which are not mirror images of each other. The absolute stereochemistry is specified according to the Cahn-Ingold-Prelog R-S system. When a compound is a pure enantiomer, the stereochemistry at each chiral center may be specified by either R or S. Resolved compounds whose absolute configuration is unknown can be designated (+) or (−) depending on the direction (dextro- or levorotatory) which they rotate plane polarized light at the wavelength of the sodium D line. To the extent a structure or chemical name does not indicate the chirality, the structure or name is intended to encompass any single stereoisomer corresponding to that structure or name, as well as any mixture of stereoisomers including racemates The language "pharmaceutically acceptable salt" includes acid addition salts that retain the biological effectiveness and properties of the compounds of Formula (I), (Ia), (Ib), or Table 1. Pharmaceutically acceptable salts can be formed with inorganic acids or organic acids, such as acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, palmoate, phosphate/hydrogen phosphate/dihydrogen phosphate, polygalacturonate, propionate, stearate, succinate, subsalicylate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoroacetic acid, sulfosalicylic acid, and the like.

The pharmaceutically acceptable salts of the compounds Formula (I), (Ia), (Ib), or Table 1 can be synthesized from a basic or acidic moiety, by conventional chemical methods. Generally, such salts can be prepared by reacting free acid forms of these compounds with a stoichiometric amount of the appropriate base (such as $Na^+$, $Ca^{2+}$, $Mg^{2+}$, or $K^+$ hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms for the compounds of Formula (I), (Ia), (Ib), or Table 1. Isotopically labeled compounds have structures depicted by the formulas given herein except that one or more atoms are replaced by an atom having a selected atomic mass or mass number. Examples of isotopes that can be incorporated into the compounds of Formula (I), (Ia), (Ib), or Table 1 include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{16}F$, $^{31}P$, $^{32}P$, $^{35}S$, $^{36}Cl$ and $^{125}I$. The compounds of Formula (I), (Ia), (Ib), or Table 1 may include various isotopically labeled compounds into which radioactive isotopes, such as $^2H$, $^3H$, $^{13}C$ and $^{14}C$, are present. Isotopically labeled compounds of Formula (I), (Ia), (Ib), or Table 1 can generally be prepared by convention techniques known to those skilled in the art or by processes analogous to those described in the accompanying Examples using appropriate isotopically labeled reagents in place of the non-labeled reagents previously employed.

Pharmaceutical Compositions

The present disclosure includes, in at least one embodiment, pharmaceutical compositions comprising a compound of Formula (I), (Ia), (Ib), or Table 1, and a pharmaceutically acceptable excipient, carrier or diluent.

The language "pharmaceutically acceptable excipient, carrier or diluent" includes compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Pharmaceutically acceptable excipients, carriers, and diluents are well known in the art and any selection of actual pharmaceutically acceptable excipients, carriers, and diluents depend on the intended use and method of administration of the pharmaceutical composition.

The disclosed compositions may be in a form suitable for oral use (for example, as tablets, lozenges, hard or soft capsules, aqueous or oily suspensions, emulsions, dispersible powders or granules, syrups or elixirs), for topical use (for example, as creams, ointments, gels, or aqueous or oily solutions or suspensions), for administration by inhalation (for example, as a finely divided powder or a liquid aerosol), for administration by insufflation (for example, as a finely divided powder) or for parenteral administration (for example, as a sterile aqueous or oily solution for intravenous, subcutaneous, intramuscular or intramuscular dosing or as a suppository for rectal dosing).

The disclosed compositions may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or oil, such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinyl pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid; coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation and/or insufflation may be in the form of a conventional pressurized aerosol arranged to dispense the active ingredient either as an aerosol containing finely divided solid or liquid droplets. Conventional aerosol propellants such as volatile fluorinated hydrocarbons may be used and the aerosol device is conveniently arranged to dispense a metered quantity of active ingredient. For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990. Depending on, for instance, potency and physical characteristics of the compound of Formula (I), (Ia), (Ib), or Table 1, and pharmaceutically acceptable salts thereof (i.e., active ingredient), pharmaceutical compositions that may be mentioned include those in which the active ingredient is present in at least 1% (or at least 10%, at least 30% or at least 50%) by weight. That is, the ratio of active ingredient to the other components (i.e. the addition of excipient, carrier, and diluents) of the pharmaceutical composition is at least 1:99 (or at least 10:90, at least 30:70 or at least 50:50) by weight.

The compounds of Formula (I), (Ia), (Ib), or Table 1, and pharmaceutically acceptable salts thereof may be administered once, twice, three times a day or as many times in a 24 hour period as medically necessary. One of skill in the art would readily be able to determine the amount of each individual dose based on the subject. In some embodiments, the compounds of Formula (I), (Ia), (Ib), or Table 1, and pharmaceutically acceptable salts thereof are administered in one dosage form, or in some embodiments, are administered in multiple dosage forms.

Methods

Compounds of Formula (I), (Ia), (Ib), or Table 1, and pharmaceutically acceptable salts thereof may inhibit JAK1 kinase, and associated protein activity related to JAK1 kinase, for example as may be shown in the tests exemplified below, and may therefore be useful in the treatment of those conditions in which such inhibition is desired and/or required. Thus, compounds of Formula (I), (Ia), (Ib), or Table 1, and pharmaceutically acceptable salts thereof may be useful in the treatment of those conditions in which it is desired and/or required that JAK1 kinase is inhibited or decreased, or in some embodiments, conditions in which it is desired and/or required that protein activity related to JAK1 kinase is inhibited or decreased. Compounds of Formula (I), (Ia), (Ib), or Table 1, and pharmaceutically acceptable salts thereof are thus expected to be useful in the treatment of disorders that may benefit from inhibition of JAK1 kinase, for example a respiratory disease/disorder and/or inflammation and/or a disease that has an inflammatory component.

Accordingly, in at least one embodiment, disclosed are methods of inhibiting JAK1 kinase in a subject comprising administering to the subject an effective amount of a compound of Formula (I), (Ia), (Ib), or Table 1, or a pharmaceutically acceptable salt thereof.

In another embodiment, disclosed is the use of a compound of Formula (I), (Ia), (Ib), or Table 1, or a pharmaceutically acceptable salt thereof, for inhibiting JAK1 kinase.

In another embodiment, disclosed is the use of a compound of Formula (I), (Ia), (Ib), or Table 1, or a pharmaceutically acceptable salt thereof, in the manufacture of a medicament for inhibiting JAK1 kinase.

Yet in another embodiment, disclosed are pharmaceutical compositions comprising a compound of Formula (I), (Ia), (Ib), or Table 1, or a pharmaceutically acceptable salt thereof, for inhibiting JAK1 kinase.

In at least one embodiment of the present disclosure, the compounds of Formula (I), (Ia), (Ib), or Table 1, or a pharmaceutically acceptable salt thereof, exhibit a JAK1 enzyme inhibitory activity ($IC_{50}$) of less than or equal to about 0.010 micromolar at physiological ATP concentration of 5 mM. In at least one other embodiment, the compounds of Formula (I), (Ia), (Ib), or Table 1, or a pharmaceutically acceptable salt thereof, exhibit an inhibitory activity ($IC_{50}$) of less than or equal to about 0.050 micromolar in a cellular IL-13 induced JAK-STAT6-luciferase assay.

In another embodiment of the present disclosure, the compounds of Formula (I), (Ia), (Ib), or Table 1, or a pharmaceutically acceptable salt thereof, exhibit a JAK1 enzyme inhibitory activity ($IC_{50}$) of less than or equal to about 0.010 micromolar at physiological ATP concentration of 5 mM, and a JAK2 and JAK3 enzyme inhibitory activity ($IC_{50}$) of greater than or equal to about 0.5 micromolar at physiological ATP concentration of 5 mM. In at least one other embodiment, the compounds of Formula (I), (Ia), (Ib), or Table 1, or a pharmaceutically acceptable salt thereof, exhibit a JAK1 enzyme inhibitory activity ($IC_{50}$) of less than or equal to about 0.010 micromolar at physiological ATP concentration of 5 mM, a JAK2 and JAK3 enzyme inhibitory activity ($IC_{50}$) of greater than or equal to about 0.5 micromolar at physiological ATP concentration of 5 mM, and an inhibitory activity ($IC_{50}$) of less than or equal to about 0.050 micromolar in a cellular IL-13 induced JAK-STAT6-luciferase assay.

In another embodiment, disclosed are methods of treating a JAK1-related disorder comprising administering to a subject an effective amount of a compound of Formula (I), (Ia), (Ib), or Table 1, or a pharmaceutically acceptable salt thereof In another embodiment, disclosed is the use of a compound of Formula (I) (Ia), (Ib), or Table 1 for treating a JAK1-related disorder comprising administering to a subject an effective amount of a compound of Formula (I), (Ia), (Ib), or Table 1, or a pharmaceutically acceptable salt thereof.

In another embodiment, disclosed is the use of a compound of Formula (I), (Ia), (Ib), or is Table 1, or a pharmaceutically acceptable salt thereof, in the manufacture of a medicament or formulation for treating a JAK1-related disorder.

In another embodiment, disclosed is the use of a compound of Formula (I), (Ia), (Ib), or Table 1, or a pharmaceutically acceptable salt thereof, in the manufacture of a medicament for treating a JAK-related disorder.

In another embodiment, disclosed are pharmaceutical compositions comprising a compound of Formula (I), (Ia), (Ib), or Table 1, or a pharmaceutically acceptable salt thereof, for the treatment of a JAK1-related disorder.

According to the present disclosure, the term "JAK1-related disorder" includes, for example, Type 1 diabetes, lupus, multiple sclerosis, rheumatoid arthritis, psoriasis, asthma, atopic dermatitis, autoimmune thyroid disorders, ulcerative colitis, Crohn's disease, COPD, vitiligo, and alopecia areata.

Compounds of Formula (I), (Ia), (Ib), or Table 1, and pharmaceutically acceptable salts thereof, may be administered at varying doses depending upon the route of administration. For instance, oral dosages may range between about 0.01 mg/kg of body weight per day (mg/kg/day) to about 100 mg/kg/day, such as about 0.01 to about 20 mg/kg/day, for example about 1.0 to about 15 mg/kg/day, for instance about 12.5 mg/kg/day. Intravenous dosages may range from between from about 0.5 mg/kg/day to about 50 mg/kg/day during constant rate infusion. Inhaled dosages may range between about 0.0001 mg/kg/day to about 0.10000 mg/kg/day, such as about 0.0001 mg/kg/day to about 0.001 mg/kg/day, for example about 0.0006 mg/kg/day. Inhaled dosages may also vary according to the delivery device utilized. For example, inhaled dosages via a dry powder inhaler device may range between about 0.010 mg/kg/day to about 0.020 mg/kg/day.

In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention As used herein, the term "effective amount" includes an amount of a compound of Formula (I), (Ia), (Ib), or Table 1, or a pharmaceutically salt thereof, that will elicit a biological or medical response in a subject, for example, the reduction or inhibition of enzyme or protein activity related to JAK1 and/or amelioration of symptoms of a JAK1-related disorder and/or the slowing or delaying of progression of a JAK1-related disorder. The effect may be objective (i.e. measurable by some test or marker) or subjective (i.e. the subject gives an indication of or feels an effect).

The term "subject" includes warm-blooded mammals, for example, primates, cows, pigs, sheep, dogs, cats, rabbits, rats, and mice. In some embodiments, the subject is a primate, for example, a human. In some embodiments, the subject is suffering from a JAK1-related disorder. In some embodiments, the subject is in need of treatment (e.g., the subject would benefit biologically or medically from treatment).

The language "inhibit," "inhibition" or "inhibiting" includes a decrease in the baseline activity of a biological activity or process. In some embodiments, the compounds of Formula (I), (Ia), (Ib), or Table 1, or a pharmaceutically acceptable salt thereof, inhibit JAK1 kinase. In some embodiments, the compounds of Formula (I), (Ia), (Ib), or Table 1, or pharmaceutically acceptable salts thereof, are selective JAK1 inhibitors. The language "selective JAK1 inhibitor" includes the compounds of Formula (I), (Ia), (Ib), or Table 1, and pharmaceutically acceptable salts thereof, that inhibit JAK1 but are inactive or less active against JAK2 or JAK3, or against both JAK2 and JAK3. Thus, in some embodiments, the compounds of Formula (I), (Ia), (Ib), or Table 1, or a pharmaceutically acceptable salt thereof, inhibit JAK1 kinase but are inactive or less active against JAK2 or JAK3, or against both JAK2 and JAK3. For example, the compounds of Formula (I), (Ia), (Ib), or Table 1, or a pharmaceutically acceptable salt thereof, exhibit a JAK1 enzyme inhibitory activity ($IC_{50}$) of less than or equal to about 0.010 micromolar at physiological ATP concentration of 5 mM, and a JAK2 and JAK3 enzyme inhibitory activity ($IC_{50}$) of greater than or equal to about 0.5 micromolar at physiological ATP concentration of 5 mM. In at least one other embodiment, the compounds of Formula (I), (Ia), (Ib), or Table 1, or a pharmaceutically acceptable salt thereof, exhibit a JAK1 enzyme inhibitory activity ($IC_{50}$) of less than or equal to about 0.010 micromolar at physiological ATP concentration of 5 mM, a JAK2 and JAK3 enzyme inhibitory activity ($IC_{50}$) of greater than or equal to about 0.5 micromolar at physiological ATP concentration of 5 mM, and an inhibitory activity ($IC_{50}$) of less than or equal to about 0.050 micromolar in a cellular IL-13 induced JAK-STAT6-luciferase assay.

The language "treat," "treating" and "treatment" includes the reduction or inhibition of enzyme or protein activity related to JAK1 kinase and amelioration of one or more symptoms of a JAK1-related disorder in a subject, or the slowing or delaying of progression of a JAK1-related disorder in a subject. Compounds of Formula (I), (Ia), (Ib), or Table 1, and pharmaceutically acceptable salts thereof, are thus indicated both in the therapeutic and/or prophylactic treatment of the above-mentioned conditions.

Examples

Compounds of Formula (I), (Ia), (Ib), or Table 1, and pharmaceutically acceptable salts thereof may be prepared using the methods and procedures described herein, or using similar methods and procedures. It will be appreciated that where typical or exemplified process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions may be determined by one skilled in the art.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection are well-known in the art. For example, numerous protecting groups, and their introduction and removal, are described in T. W. Greene and G. M. Wuts, Protecting Groups in Organic Synthesis, Third Edition, Wiley, New York, 1999, and references cited therein. Processes for preparing compounds of the invention are provided as further embodiments of the invention and are illustrated by the procedures below. Stereochemical assignment of the isolated enantiomers was made based on biological activity against JAK1 in the Enzyme Inhibition Studies, as shown in Table 24.

Intermediate 1: 7-nitro-3-(4,4,5,5-tetramethyl-1,3,2-dioxaborolan-2-yl)-1-tosyl-1H-indole Step 1

A solution of NaOH (599 g, 14986.55 mmol) in water (1500 mL) was added to a stirred mixture of 7-nitro-1H-indole (243 g, 1498.65 mmol) and tetrabutylammonium hydrogen sulfate (50.9 g, 149.87 mmol) in DCM (3000 mL) at 25° C., over a period of 5 minutes under air. The resulting mixture was stirred at 25° C. for 20 minutes. 4-methylphenylsulfonyl chloride (371 g, 1948.25 mmol) was added under air and the resulting mixture was stirred at 25° C. for 16 hours. The reaction mixture was diluted with DCM (2000 mL), and washed sequentially with water (2×500 mL), 10% aqueous $K_2CO_3$ (2×500 mL), and 1 M HCl (2×500 mL) and saturated NaCl (2×500 mL). The organic layer was dried over $Na_2SO_4$, filtered and evaporated. When approximately 200 mL DCM was left, EtOAc (500 mL) was added. The solvent was removed under reduced pressure. When approximately 200 mL EtOAc was left, MTBE (1000 mL) was added. The precipitate was collected by filtration, washed with MTBE (1000 mL) and dried under vacuum to afford 7-nitro-1-tosyl-1H-indole (402 g, 85%) as a white solid.

$^1$H NMR (300 MHz, DMSO-$d_6$) δ 2.39 (s, 3H), 7.09 (d, 1H), 7.40-7.55 (m, 3H), 7.75-7.85 (m, 3H), 7.95-8.00 (m, 1H), 8.06 (d, 1H). m/z (ES+), [M+H]$^+$=317.

Step 2

Bromine (81 mL, 1580 mmol) was added dropwise to 7-nitro-1-tosyl-1H-indole (50 g, 158 mmol) in $CCl_4$ (1000 mL) at 80° C. The resulting solution was stirred at 80° C. for 6 hours. The mixture was cooled to room temperature, concentrated in vacuo and the residue was washed with EtOAc to afford 3-bromo-7-nitro-1-tosyl-1H-indole (53 g, 85%) as a brown solid.

$^1$H NMR (300 MHz, DMSO-$d_6$) δ 2.41 (s, 3H), 7.55-7.62 (m, 2H), 7.57 (t, 1H), 7.85-7.92 (m, 3H), 7.96 (d, 1H), 8.49 (s, 1H). m/z (ES−), [M−H]$^+$=393.

Step 3

A solution 3-bromo-7-nitro-1-tosyl-1H-indole (200 g, 506 mmol), 4,4,4',4',5,5,5',5'-octamethyl -2,2'-bi(1,3,2-dioxaborolane) (193 g, 759 mmol), potassium acetate (99 g, 1012 mmol) and PdCl$_2$(dppf) (18.5 g, 25.3 mmol) in 1,4-dioxane (1500 mL) was degassed with nitrogen three times and the reaction mixture stirred at 90° C. for 8 hours. The mixture was cooled to room temperature and concentrated in vacuo. The solid was treated with water, filtered, washed with methanol and dried in vacuo to afford 7-nitro-3-(4,4,5,5-tetramethyl-1,3,2-dioxaborolan-2-yl)-1-tosyl-1H-indole (150 g, 67%) as a grey solid.

$^1$H NMR (400 MHz, CDCl$_3$) δ 1.41 (s, 12H), 2.47 (s, 3H), 7.38-7.43 (m, 3H), 7.66 (d, 1H), 7.87 (d, 2H), 8.24 (s, 1H), 8.29-8.32 (d, 1H). m/z (ES+), [M+H]$^+$=443.

Intermediate 2: 3-(2-chloro-5-methylpyrimidin-4-yl)-7-nitro-1-tosyl-1H-indole 7-nitro-3-(4,4,5,5-tetramethyl-1,3,2-dioxaborolan-2-yl)-1-tosyl-1H-indole, Intermediate 1 (50 g, 113 mmol) was charged in to a 1L reactor equipped with a condenser and nitrogen inlet. 2,4-dichloro-5-methylpyrimidine (24 g, 147 mmol) and 2-methyltetrahydrofuran (200 mL, 4 vol) as added to the reactor. A solution of potassium carbonate (46.9 g, 339 mmol) in water (10 mL, 2 vol) was degassed and back filled with N$_2$ and added to the reaction mixture. The reactor was degassed and backfilled (3×N$_2$), dichloro[1,1'-bis(diphenylphosphino)ferrocene]palladium dichloromethane adduct (4.62 g, 5.65 mmol) was added to the reaction mixture, degassed and backfilled with N$_2$ again (3×) and the reaction was then slowly heated to 60° C. After 30 min a precipitate was formed. The reaction was stirred for 1 h and the reactor temperature set to 25° C. After 30 min cooling, the internal temperature was 42° C. and heptane (1 vol) added. The reactor temperature was then set to +5° C. At 20° C., water (4 vol) was added and cooling contined to +5 ° C. over 1 hour and then stirred for 2 hours. The reaction mixture was filtered on Büchner funnel and the solid washed with water (4 vol) and EtOAc (2 vol) to afford a light yellow solid that was dried under a nitrogen flow. The solid was stirred in EtOAc (1 vol), filtered and resulting solid was dried under vacuum to afford (42.8 g). Mother liqours were combined and evaporated in vacuo to afford (20 g). 700 g of silica slurried in heptane was packed on a column (10×300 mm). Solids were dissolved in DCM, combined and loaded to the column. After complete elution of DCM, the column was eluted with 20% EtOAc in heptanes, followed by a gradient from 20-50% EtOAc in heptane. The desired compound was combined and evaporated in vacuo. The residue was slurried in 50% EtOAc in heptane (0.5 vol), filtered and dried under a flow of nitrogen to afford 3-(2-chloro-5-methylpyrimidin-4-yl)-7-nitro-1-tosyl-1H-indole (35.6 g, 71%) as a solid.

$^1$H NMR (400 MHz, DMSO-$d_6$) δ 2.40 (s, 3H), 2.44 (s, 3H), 7.54 (d, 2H), 7.61 (t, 1H), 7.91 (d, 2H), 7.95-8.04 (m, 1H), 8.40 (dd, 1H), 8.62 (s, 1H), 8.79 (s, 1H). m/z (ES+), [M+H]$^+$=442.9.

Intermediate 3: 3-(2-chloro-5-methylpyrimidin-4-yl)-7-nitro-1H-indole 3-(2-chloro-5-methylpyrimidin-4-yl)-7-nitro-1-tosyl-1H-indole, Intermediate 2 (2.477 g, 5.59 mmol) was dissolved in 1,4-dioxane/water 2:1 (75 mL) and 3.8 M sodium hydroxide (22 mL, 83.9 mmol) was added. The resulting reaction mixture was heated to 50° C. for 2 h. The reaction mixture was allowed to cool to room temperature and neutralized by addition of 2 M HCl. The formed solid was filtered off, washed with EtOAc, Et$_2$O and dried under vacuum to afford 3-(2-chloro-5-methylpyrimidin-4-yl)-7-nitro-1H-indole (1.894 g, 117% (wet)) as a solid.

$^1$H NMR (500 MHz, DMSO-$d_6$) δ 2.52 (s, 3H), 7.47 (t, 1H), 8.20 (d, 1H), 8.25 (d, 1H), 8.63 (s, 1H), 8.90 (d, 1H), 12.66 (s, 1H). m/z (ES+), [M+H]$^+$=289.2.

Intermediate 4: 3-(2,5-dichloropyrimidin-4-yl)-7-nitro-1H-indole

Step 1

PdCl$_2$(dppf)*CH$_2$Cl$_2$ (0.554 g, 0.68 mmol) was added to 7-nitro-3-(4,4,5,5-tetramethyl-1,3,2-dioxaborolan-2-yl)-1-tosyl-1H-indole, Intermediate 1 (3.00 g, 6.78 mmol), 2,4,5-trichloropyrimidine (1.617 g, 8.82 mmol) and K$_2$CO$_3$ (2.81 g, 20.35 mmol) in THF/water 4:1 (75 mL) at 25° C. under nitrogen. The resulting mixture was stirred at 80° C. for 4 hours. The reaction mixture was allowed to cool to room temperature, diluted with EtOAc (150 mL) and washed with brine (150 mL). The organic layer was dried over Na$_2$SO$_4$, filtered and evaporated in vacuo. The residue was purified by flash silica chromatography using a gradient of 8-30% EtOAc in petroleum ether as mobile phase. Pure fractions were evaporated in vacuo and the residue crystallized from acetonitrile to afford 1-((4-chlorophenyl)sulfonyl)-3-(2,5-dichloropyrimidin-4-yl)-7-nitro-1H-indole (1.43 g, 43.4%) as a white solid.

$^1$H NMR (300 MHz, DMSO-$d_6$) δ 2.42 (s, 3H), 7.52 (d, 2H), 7.66 (t, 1H), 7.91-8.14 (m, 3H), 8.52 (dd, 1H), 8.90 (s, 1H), 9.08 (s, 1H). m/z (ES+), [M+H]$^+$=463.

Step 2

A solution of NaOH (2.202 g, 55.05 mmol) in water (30 mL) was added to a stirred suspension of 3-(2,5-dichloropyrimidin-4-yl)-7-nitro-1-tosyl-1H-indole (1.7 g, 3.67 mmol) in 1,4-dioxane (30 mL) at 25° C. The resulting mixture was stirred at 50° C. for 1 hours and was then cooled to room temperature. The reaction mixture was diluted with EtOAc (200 mL), washed with water (50 mL), saturated NaHCO$_3$ (50 mL), brine (50 mL). The organic layer was dried over Na$_2$SO$_4$, filtered and evaporated in vacuo to afford 3-(2,5-dichloropyrimidin-4-yl)-7-nitro-1H-indole, (0.500 g, 44.1%) as a yellow solid.

$^1$H NMR (300 MHz, DMSO-$d_6$) δ 7.34 (t, 1H), 8.06 (dd, 1H), 8.67 (s, 1H), 8.78 (s, 1H), 8.87 (dd, 1H). m/z (ES+), [M+H]$^+$=309.

Intermediate 5: 2-fluoro-3-(methylsulfonyl)aniline

Step 1

Copper(I) iodide (1.002 g, 5.26 mmol) was added in one portion to 3-bromo-2-fluoroaniline (5 g, 26.31 mmol), N1,N2-dimethylethane-1,2-diamine (0.464 g, 5.26 mmol) and sodium iodide (7.89 g, 52.63 mmol) in 1,4-dioxane (10 mL) at 25° C. over a period of 1 minute under nitrogen. The resulting suspension was stirred at 110° C. for 1 day. The reaction mixture was filtered through celite and concentrated in vacuo. The crude product was purified by flash silica chromatography using a gradient 5-30% EtOAc in petroleum ether as mobile phase. Pure fractions were evaporated in vacuo to afford 2-fluoro-3-iodoaniline (5.00 g, 80%) as a brown oil.

$^1$H NMR (400 MHz, DMSO-$d_6$) δ 5.32 (bs, 2H), 6.59-6.83 (m, 2H), 6.83-6.93 (m, 1H). m/z (ES+), [M+H]$^+$=238.

Step 2

Copper(I) iodide (0.402 g, 2.11 mmol) was added to 2-fluoro-3-iodoaniline (5.00 g, 21.10 mmol), sodium methanesulfinate (3.23 g, 31.64 mmol), N1,N2-dimethylethane-1,2-diamine (0.558 g, 6.33 mmol) in DMSO (20 mL) under nitrogen. The resulting suspension was stirred at 95° C. for 18 hours. The reaction mixture was diluted with EtOAc (50 mL), washed with water (50 mL) and brine (50 mL). The organic layer was dried over Na$_2$SO$_4$, filtered and evaporated in vacuo. The residue was purified by preparative TLC using EtOAc/petroleum ether 1:1 to afford 2-fluoro-3-(methylsulfonyl)aniline (3.20 g, 80%) as a colourless oil which solidified on standing.

$^1$H NMR (400 MHz, CDCl$_3$) δ 3.20 (s, 3H), 3.96 (bs, 2H), 6.97-7.13 (m, 2H), 7.20-7.31 (m, 1H). m/z (ES+), [M+H]$^+$=190.

The procedure described above was repeated using the indicated sulfinate to give Intermediate 6 described in Table 2:

TABLE 2

| Intermediate | Sulfinate | ¹H NMR δ (CDCl₃, 400 MHz) | m/z (ES+), [M + H]⁺ | Yield % |
|---|---|---|---|---|
| 6 3-(cyclopropylsulfonyl)-2-fluoroaniline | 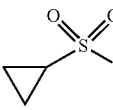 | 0.95 - 1.15 (m, 2H), 1.30 - 1.43 (m, 2H), 2.65 - 2.80 (m, 1H), 4.01 (bs, 2H), 6.91 - 7.11 (m, 2H), 7.11 - 7.25 (m, 1H). | 216 | 60 |

Intermediate 7: (3-bromo-2-fluorophenyl)(ethyl)sulfane

Lithium diisopropylamide (17.14 mL, 34.29 mmol) was added dropwise to 1-bromo-2-fluorobenzene (5.00 g, 28.57 mmol) in THF (250 mL) at −78° C. over a period of 10 minutes under nitrogen. The resulting mixture was stirred at −78° C. for 60 minutes. 1,2-diethyldisulfane (5.20 g, 42.54 mmol) was added dropwise over 20 minutes. The resulting mixture was stirred at −78° C. for 60 minutes and then at room temperature overnight. The reaction mixture was quenched with water (50 mL) and extracted with EtOAc (2×250 mL). The combined organic extracts were dried over Na₂SO₄, filtered and evaporated in vacuo. The residue was purified by flash silica chromatography using a gradient of 0-10% EtOAc in pentane as eluent. Pure fractions were evaporated in vacuo to afford (3-bromo-2-fluorophenyl)(ethyl)sulfane (5.27 g, 78%) as a colourless oil.

¹H NMR (300 MHz, CDCl₃) 1.32 (t, 3H), 2.95 (q, 2H), 6.90-7.04 (m, 1H), 7.22-7.34 (m, 1H), 7.35-7.47 (m, 1H).

Intermediate 8: tert-butyl (3-(ethylthio)-2-fluorophenyl)carbamate (3-bromo-2-fluorophenyl)(ethyl)sulfane, Intermediate 7 (4.14 g, 17.61 mmol) was added in one portion to cyclohexane-1,2-diamine (6.03 g, 52.82 mmol) phosphoric acid, potassium salt (3.74 g, 17.61 mmol), copper(I) iodide (8.38 g, 44.02 mmol) and tent-butyl carbamate (10.31 g, 88.04 mmol) in 1,4-dioxane (80 mL) at 25° C. under nitrogen. The resulting mixture was stirred at 100° C. for 6 hours and then allowed to cool to room temperature. The reaction mixture was filtered and evaporated in vacuo. The residue was purified by flash silica chromatography using a gradient of 0-10% EtOAc in pentane. Pure fractions were evaporated in vacuo to afford tert -butyl (3-(ethylthio)-2-fluorophenyl) carbamate (1.412 g, 29.6%) as a yellow oil.

¹H NMR (400 MHz, CDCl₃) δ 1.31 (t, 3H), 1.55 (s, 9H), 2.94 (q, 2H), 6.73 (bs, 1H), 6.91-7.19 (m, 2H), 7.92-8.05 (m, 1H).

Intermediate 9: tert-butyl (3-(ethylsulfonyl)-2-fluorophenyl)carbamate tert-butyl (3-(ethylthio)-2-fluorophenyl)carbamate, Intermediate 8 (1.4 g, 5.16 mmol) was added in one portion to 3-chlorobenzene-1-carboperoxoic acid (2.67 g, 15.48 mmol) in DCM (15 mL) at 0° C. under nitrogen. The resulting mixture was stirred at room temperature for 16 hours. The reaction mixture was diluted with DCM (50 mL), filtered, washed with saturated NaHCO₃ (2×50 mL) and brine (50 mL). The organic layer was dried over Na₂SO₄, filtered and evaporated in vacuo. The residue was purified by preparative TLC developed with petroleum ether/EtOAc 3:1 to afford tert-butyl (3-(ethylsulfonyl)-2-fluorophenyl)carbamate, (1.650 g, 105%) as a yellow oil. m/z (ES−), [M−H]⁺=302.

Intermediate 10: 3-(ethylsulfonyl)-2-fluoroaniline 2,2,2-trifluoroacetic acid (10.0 g, 87.70 mmol) was added to tert-butyl (3-(ethylsulfonyl)-2-fluorophenyl)carbamate, Intermediate 9 (1.65 g, 5.44 mmol) in DCM (20 mL) at 20° C. The resulting mixture was stirred at 25° C. for 1 hour. The reaction mixture was evaporated in vacuo, redissolved in DCM (50 mL), washed with saturated NaHCO₃ (2×100 mL) and brine (100 mL). The organic layer was dried over Na₂SO₄, filtered and evaporated in vacuo to afford 3-(ethylsulfonyl)-2-fluoroaniline (0.786 g, 71.1%) as yellow oil.

¹H NMR δ (CDCl₃, 400 MHz) δ 1.32 (t, 3H), 3.32 (q, 2H), 3.60-4.10 (bs, 2H), 7.00-7.17 (m, 2H), 7.17-7.34 (m, 1H). m/z (ES+), [M+H]⁺=204.

Intermediate 11: 3-(2-((2-fluoro-3-(methylsulfonyl)phenyl)amino)-5-methylpyrimidin-4-yl) -1H-indol-7-amine

Step 1

3-(2-chloro-5-methylpyrimidin-4-yl)-7-nitro-1-tosyl-1H-indole, Intermediate 2 (20.0 g, 45.16 mmol), 2-fluoro-3-(methylsulfonyl)aniline hydrochloride, Intermediate 5 (11.2 g, 49.68 mmol), cesium carbonate 30.9 g, 94.8 mmol), Pd₂(dba)₃ (4.14 g, 4.52 mmol) and 2'-(dicyclohexylphosphino)-N,N-dimethyl-[1,1'-biphenyl]-2-amine (3.55 g, 9.03 mmol) were charged in a 1L reactor under nitrogen. 2-methyltetrahydrofuran (200 mL) and water (100 mL) were added at room temperature. The reaction was evacuated and back-filled with N₂ (3×) and was then heated to 72.5° C. (T,=80° C.) and stirred for 4 h (brown precipitate formed after 3 h).

Heptane (400 mL, 20 vol) was added, the heating stopped and the reaction cooled to 17° C. over 30 min. The precipitate was stirred for 10 min and was then filtered on a buchner funnel. The filter cake was washed with water (2 vol×3), EtOAc/heptane 1:2 (3 vol×3) and then dried under vacuum/nitrogen to afford N-(2-fluoro-3-(methylsulfonyl)phenyl)-5-methyl-4-(7-nitro-1-tosyl -1H-indol-3-yl)pyrimidin-2-amine (25.93 g, 96%) as a brown solid. Continued without further purification. m/z (ES+), [M+H]⁺=596.2.

Step 2

In a 1L reactor, 3-(2-chloro-5-methylpyrimidin-4-yl)-7-nitro-1-tosyl-1H-indole (27.0 g, 45.3 mmol) was charged at room temperature, 2-methyltetrahydrofuran (250 mL) and 3.8 M NaOH (aq.) (250 mL) were added to give a brown insoluble mixture. The mixture was heated to 85° C. and stirred overnight. Heptane (10 vol) was charged to the reaction mixture, cooled to 17° C. over 40 min and stirred for 30 min. The solid was filtered with a buchner funnel and the filter cake washed with water (3×40 mL). pH of the aq wash: 10-11 by pH paper. Charged 40 mL of water to the filter cake and slurried while adjusting the pH to 7 by 0.5 N HCl. The solid was again filtered with a buchner funnel, washed with water (50 mL), dried under nitrogen/vacuum for 20 min and then washed with heptane/EtOAc (4×40 mL). (45% unreacted starting material by LCMS, the compound was reacted again under same conditions). The solid was charged to a 1L reactor and 2-methyltetrahydrofuran (250 mL) and 3.8 M NaOH (aq.) (250 mL) were added to give a brown insoluble mixture. The mixture was heated to 85° C. and stirred overnight. Heptane (10 vol) was charged to the reaction mixture, cooled to 17° C. over 40 min and stirred for 30 min. The solid was filtered with a bUchner funnel and the filter cake washed with water (3×40 mL). pH of the aq wash: 10-11 by pH paper. Charged 40 mL of water to the filter cake and slurried while adjusting the pH to 7 by 0.5 N HCl. The solid was again filtered with a bUchner funnel, washed with water (50 mL), dried under nitrogen/vacuum for 20 min and then washed with heptane/EtOAc (4×40 mL) and dried to afford N-(2-fluoro-3-(methylsulfonyl)phenyl)-5-methyl -4-(7-nitro-1H-indol-3-yl)pyrimidin-2-amine (20.0 g, 100%). m/z (ES+), [M+H]$^+$=442.1.

Step 3

N-(2-fluoro-3-(methylsulfonyl)phenyl)-5-methyl-4-(7-nitro-1H-indol-3-yl)pyrimidin-2-amine (11.0 g, 24.9 mmol) was charged to a 1L reactor and 2-methyltetrahydrofuran/EtOH 2:1 (330 mL) added. The reactor was heated to 80° C., stirred for 10 min for solubility and then slowly cooled to 30° C. 10% Pd-C (2.00 g, 24.9 mmol, 50% wet) and solution of ammonium formate (9.43 g, 149.5 mmol) in water (10 mL) (endothermic) was added at room temperature under nitrogen. The reaction mixture was slowly heated to 80° C. and stirred for 15 min. It was then allowed to cool to 40-50° C., filtered on a Büchner funnel under nitrogen (causion), washed the cake with hot THF/EtOH 1:1 (50 mL) and the filtrate concentrated and coevaporated in vacuo with DCM (50 mL) to afford 3-(2-((2-fluoro-3-(methylsulfonyl)phenyl) amino)-5-methylpyrimidin-4-yl)-1H-indol-7-amine 10.0 g, 98%) as a brown solid. m/z (ES+), [M+H]$^+$=412.4.

Intermediate 12: N-(3-(ethylsulfonyl)-2-fluorophenyl)-5-methyl-4-(7-nitro-1H-indol-3-yl)pyrimidin-2-amine Pd$_2$(dba)$_3$ (159 mg, 0.17 mmol) and 2'-(dicyclohexylphosphino)-N,N-dimethyl-[1,1'-biphenyl]-2-amine (136 mg, 0.35 mmol) was added to 3-(2-chloro-5-methylpyrimidin-4-yl)-7-nitro-1H-indole, Intermediate 3 (500 mg, 1.73 mmol), 3-(ethylsulfonyl)-2-fluoroaniline, Intermediate 10 (352 mg, 1.73 mmol) and cesium carbonate (1693 mg, 5.20 mmol) in DMF (15 mL) at 23° C. under nitrogen. The resulting solution was stirred at 80° C. for 3 hours. The reaction mixture was filtered through celite and the solvent evaporated in vacuo to afford N-(3-(ethylsulfonyl)-2-fluorophenyl)-5-methyl-4-(7-nitro-1H-indol-3-yl)pyrimidin-2-amine (1.22 g, 155%) as dark solid. Used without further purification. m/z (ES+), [M+H]$^+$=456.

The procedure described above was repeated using the indicated starting intermediates to give Intermediates 13-14 described in Table 6:

TABLE 6

| Intermediate | Starting intermediates | $^1$H NMR (300 MHz) δ | m/z (ES+) [M + H]$^+$ | Yield % |
|---|---|---|---|---|
| 13$^a$ N-(3-(cyclopropylsulfonyl)-2-fluorophenyl)-5-methyl-4-(7-nitro-1H-indol-3-yl)pyrimidin-2-amine | 3, 6 | | 468 | 103 |
| 14$^b$ 5-chloro-N-(2-fluoro-3-(methylsulfonyl)phenyl)-4-(7-nitro-1H-indol-3-yl)pyrimidin-2-amine | 4, 5 | (DMSO-d$_6$) 3.30 (s, 3H), 7.24-7.34 (m, 1H), 7.44-7.52 (m, 1H), 7.64-7.73 (m, 1H), 8.08-8.30 (m, 2H), 8.55-8.62 (m, 2H), 8.83 (d, 1H), 9.77 (s, 1H), 12.59 (s, 1H). | 462 | 40 |

$^a$The reaction mixture was concentrated in vacuo.
$^b$The reaction mixture was diluted with EtOAc (200 mL), washed with water (50 mL) and brine (200 mL). The organic layer was dried over Na$_2$SO$_4$, filtered and evaporated in vacuo. The residue was purified by preparative TLC using DCM/MeOH 5:1 as eluent.

Intermediate 15: 3-(2-((3-(ethylsulfonyl)-2-fluorophenyl)amino)-5-methylpyrimidin-4-yl) -1H-indol-7-amine N-(3-(ethylsulfonyl)-2-fluorophenyl)-5-methyl -4-(7-nitro-1H-indol-3 -yl)pyrimidin-2-amine, Intermediate 12 (1.406 g, 3.09 mmol), ammonium chloride (0.991 g, 18.52 mmol) and iron (1.034 g, 18.52 mmol) in MeOH/THF/water 1:1:1 (75 mL) were stirred at 60° C. for 3 hours. The reaction mixture was filtered through celite and the solvent removed under reduced pressure. The residue was purified by preparative TLC using DCM/MeOH 10:1 as eluent to afford 3-(2-((3-(ethylsulfonyl)-2-fluorophenyl)amino)-5-methylpyrimidin-4-yl)-1H-indol-7-amine (0.600 g, 46%) as a brown solid.

$^1$H NMR (300 MHz, DMSO-d$_6$) δ 1.11 (t, 3H), 2.37 (s, 3H), 3.33 (q, 2H), 5.12 (bs, 2H), 6.39 (d, 1H), 6.74 (t, 1H), 7.38 (t, 1H), 7.44-7.66 (m, 2H), 7.94 (d, 1H), 8.25 (s, 1H), 8.34 (t, 1H), 9.03 (s, 1H), 11.34 (s, 1H). m/z (ES+), [M+H]$^+$=426.

The procedure described above was repeated using the indicated starting intermediate to give Intermediates 16-17 described in Table 7:

TABLE 7

| Intermediate | Starting intermediate | m/z (ES+), [M + H]+ | Yield % |
|---|---|---|---|
| 16[b] 3-(2-((3-(cyclopropylsulfonyl)-2-fluorophenyl)amino)-5-methylpyrimidin-4-yl)-1H-indol-7-amine | 13 | 438 | 63 |
| 17[a] 3-(5-chloro-2-((2-fluoro-3-(methylsulfonyl)phenyl)amino)pyrimidin-4-yl)-1H-indol-7-amine | 14 | 432 | 87 |

[a]The reaction mixture was filtered through celite, evaporated in vacuo and redissolved in DCM (50 mL). The organic phase was washed with water (2 × 50 mL), dried over $Na_2SO_4$, filtered and evaporated in vacuo.
[b]The reaction was stirred for 2 h. The reaction mixture was filtered through celite, diluted with EtOAc (100 mL). The organic layer was dried over $Na_2SO_4$, filtered and evaporated in vacuo.

Intermediate 18: 3-(5-fluoro-2-((2-fluoro-3-(methylsulfonyl)phenyl)amino)pyrimidin-4-yl) -1H-indol-7-amine Step 1

A solution of potassium carbonate (40.9 mL, 678.28 mmol) was charged to a 1L reactor equipped with a thermometer and nitrogen inlet. The mixture was degassed three times with $N_2$ at room temperature (23° C.). 7-nitro-3-(4,4,5,5-tetramethyl-1,3,2-dioxaborolan-2-yl)-1-tosyl-1H -indole, Intermediate 1 (100 g, 226.09 mmol), 2,4-dichloro-5-fluoropyrimidine (49.1 g, 293.92 mmol) and methyl THF (1000 mL) were added and stirred for 10 min at room temperature. The resulting mixture was degassed 3 times with nitrogen. Dichloro[1,1'-bis(diphenylphosphino)ferrocene]palladium dichloromethane adduct (9.23 g, 11.30 mmol) was added to the reaction mixture and the resulting mixture was degassed and backfilled again (3×$N_2$) and stirred at 23° C. over night to give a yellow precipitate. Heptane (500 mL) was charged to the reaction mixture at room temperature and stirred for 10 min. The stirring was then stopped and the precipitate allowed to settle down. The reaction mixture was cooled to 5° C. and stirred for 1 h. The precipitate was filtered through a Glass-funnel, washed with water until water reached the neutral pH (13 vol, displacement wash, 1.3L). The filter cake was then washed with EtOAc/heptane mixture 1:1 (5×2 vol, 1L) at room temperature, heptane (2×200 mL, 2×2 vol) and the solid dried under vacuum at 35° C. over night to afford 3-(2-chloro-5-fluoropyrimidin-4-yl) -7-nitro-1-tosyl-1H-indole (97 g, 89% effective yield).
$^1$H NMR (400 MHz, DMSO-$d_6$) δ 2.41 (s, 3H), 7.51 (d, 2H), 7.69 (t, 1H), 7.95 (d, 2H), 8.01 (dd, 1H), 8.75 (d, 1H), 8.81 (dd, 1H), 9.01 (d, 1H). m/z (ES+), [M+H]$^+$=447.2.

Step 2

3-(2-chloro-5-fluoropyrimidin-4-yl)-7-nitro-1-tosyl-1H-indole (89.5 g, 200.30 mmol) , 2-fluoro -3-(methylsulfonyl) aniline hydrochloride, Intermediate 5 (54.2 g, 240.36 mmol), Pd$_2$(dba)$_3$ (9.17 g, 10.01 mmol) and 2'-(dicyclohexylphosphino)-N,N-dimethyl-[1,1'-biphenyl]-2-amine (7.88 g, 20.03 mmol) was added to a 2 L reactor under nitrogen. Degassed 2-2-methyltetrahydrofuran (1000 mL) and a solution of cesium carbonate (137 g, 420.62 mmol) in water (450 mL) were added at room temperature and the reaction mixture was degassed (x7). The reaction was then heated to 72.6° C. and then stirred overnight. The reaction was cooled to 4-5° C. and stirred for at least 30 min. The solid was filtered on a Büchner funnel, washed with cold 2-2-methyltetrahydrofuran (300 mL, 3 vol), water (3×300 mL, 3 vol) and EtOAc/heptane mixture 1:2 (3×300 mL, 3 vol) and dried under vacuum at 40° C. to afford 5-fluoro-N-(2-fluoro-3-(methylsulfonyl)phenyl)-4-(7-nitro-1-tosyl-1H-indol-3-yl) pyrimidin-2-amine (77.89 g, 65% effective yield) as a brown solid.
$^1$H NMR (400 MHz, DMSO-$d_6$) δ 2.56-2.64 (m, 3H), 3.42 (d, 3H), 7.52-7.64 (m, 4H), 7.73 (t, 1H), 7.98-8.09 (m, 3H), 8.22 (t, 1H), 8.71 (s, 1H), 8.79 (d, 1H), 8.94 (d, 1H), 9.89 (s, 1H). m/z (ES+), [M+H]$^+$=600.2.

Step 3

5-fluoro-N-(2-fluoro-3-(methylsulfonyl)phenyl)-4-(7-nitro-1-tosyl-1H-indol-3-yl)pyrimidin-2-amine (97.7 g, 129.87 mmol) was charged to a 5 L reactor at room temperature. A mixture of THF (100 mL) and 3.8 M NaOH (aq) (1000 mL) were added to give a brown insoluble mixture. The mixture was heated to 75° C. with reflux and stirred over the weekend. THF (10 vol) and heptane (10 vol) were charged to the reaction mixture. It was then allowed to cool to 17° C. over 40 min, stirred for 60 min and the solid filtered on a Büchner funnel. The filter cake was washed with 1M citic acid (500 mL, until pH neutral), water (5×300 mL, until pH neutral) followed by heptane/EtOAc (4×400 mL). The solid was dried under vacuum to afford 5-fluoro-N-(2-fluoro-3-(methylsulfonyl)phenyl)-4-(7-nitro-1H-indol-3-yl)pyrimidin-2-amine (55.0 g, 95%).
$^1$H NMR (400 MHz, DMSO-$d_6$) δ 3.27-3.38 (m, 3H), 7.30 (t, 1H), 7.47 (t, 1H), 7.64 (t, 1H), 8.11-8.29 (m, 3H), 8.52 (d, 1H), 8.98 (d, 1H), 9.60 (s, 1H), 12.57 (s, 1H). m/z (ES+), [M+H]$^+$=446.2.

Step 4

To as stirred suspension of 5-fluoro-N-(2-fluoro-3-(methylsulfonyl)phenyl)-4-(7-nitro-1H-indol -3-yl)pyrimidin-2-amine (59.5 g, 123.5 mmol, 92.5% Wt) in THF/EtOH 2:1 (600 mL) at room temperature and under nitrogen were added 10% Pd/C (12.0 g, 123.5 mmol, 50% wet) and a solution of ammonium formate (46.8 g, 741.4 mmol) in water (50 mL). The reaction mixture was slowly heated to 70° C. and stirred for 30 min. 12 g activated carbon was added and the mixture was stirred for 15 min. The reaction mixture was cooled to 40° C. and filtered on a Büchner funnel (paper) under nitrogen. The filter cake was washed with THF/EtOH (160 mL). The filtrate was concentrated to 4 vol and resulting slurry cooled to room temperature and filtered under nitrogen. The solid was washed with water (2 vol), ethanol (2 vol) and dried under nitrogen/vacuum at 40° C. to afford 3-(5-fluoro-2-((2-fluoro-3-(methylsulfonyl)phenyl)amino)pyrimidin-4-yl)-1H-indol-7-amine (44.3 g, 86%) as a light brown solid.
$^1$H NMR (400 MHz, DMSO-$d_6$) δ 3.28 (s, 3H), 5.20 (bs, 2H), 6.43 (dd, 1H), 6.78 (t, 1H), 7.44 (t, 1H), 7.57-7.63 (m, 1H), 7.66 (d, 1H), 8.09-8.25 (m, 2H), 8.38 (d, 1H), 9.34 (s, 1H), 11.57 (s, 1H). m/z (ES+), [M+H]$^+$=416.3.

Intermediate 19: 3-(2-chloro-5-methylpyrimidin-4-yl)-7-nitro-1-((2-(trimethylsilyl)ethoxy)methyl)-1H-indole Sodium hydride (60% dispersion in mineral oil) (1.32 g, 33.10 mmol) was added portion-wise to a stirring yellow suspension of 3-(2-chloro-5-methylpyrimidin-4-yl)-7-nitro- 1H-indole, Intermediate 3 (6.37 g, 22.07 mmol) in anhydrous THF (150 mL) at 0° C. After stirring for 25 min (cessation of gas evolution) (2-(chloromethoxy)ethyl)trimethylsilane (4.10 mL, 23.17 mmol) was added rapidly dropwise. After 5 minutes, the cooling bath was removed and the reaction left to stir at ambient temperature for 1.5 hour. Additional sodium hydride (60% dispersion in mineral oil) (130 mg, 3.3 mmol) and (2-(chloromethoxy)ethyl)trimethylsilane (0.4 mL, 2.3 mmol) were added. The reaction was stirred for an additional 40 min then quenched with saturated NaHCO$_3$ (aq) and the pale yellow mixture was dilute with Et$_2$O. The layers were separated and the aqueous layer extracted with Et$_2$O (x2). The combined organic layer was washed with brine, dried over MgSO$_4$, filtered and evaporated in vacuo. The residue was dissolved in chloroform and purified by automated silica gel flash chromatography using a 120 g column. A gradient of 5% EtOAc in hexane for 3 min followed by 5-45% EtOAc in hexane over 25 min was used as mobile phase. The product was collected using the wavelength 254 nm to afford 3-(2-chloro-5-methylpyrimidin-4-yl)-7-nitro-1-((2-(trimethylsilyl)ethoxy)methyl)-1H-indole (9.21 g, 100%) as a yellow solid.

$^1$H NMR (400 MHz, DMSO-d$_6$) δ −0.16 (s, 9H) 0.60-0.73 (m, 2H) 2.51-2.52 (m, 3H) 3.11-3.22 (m, 2H) 5.72 (s, 2H) 7.48 (t, 1H) 7.94 (d, 1H) 8.57 (s, 1H) 8.64 (s, 1H) 8.84 (d, 1H). m/z (ES+), [M+H]$^+$=419.2.

Intermediate 20: 3-(2-((2-fluoro-3-(methylsulfonyl)phenyl)amino)-5-methylpyrimidin-4-yl) -1-((2-(trimethylsilyl)ethoxy)methyl)-1H-indol-7-amine Step 1

Cesium carbonate (2.333 g, 7.16 mmol) was added to 3-(2-chloro-5-methylpyrimidin-4-yl)-7-nitro-1-((2-(trimethylsilyl)ethoxy)methyl)-1H-indole, Intermediate 19 (1.0 g, 2.39 mmol), 2-fluoro-3-(methylsulfonyl)aniline, Intermediate 5 (0.542 g, 2.86 mmol), Pd$_2$(dba)$_3$ (0.219 g, 0.24 mmol) and 2-dicyclohexylphosphino-2'-(N,N-dimethylamino)-biphenyl (Davephos) (0.188 g, 0.48 mmol) in DMF (20 mL) at 25° C. under nitrogen. The resulting mixture was stirred at 80° C. for 3 hours and was the allowed to cool to room temperature. The reaction mixture was diluted with EtOAc (200 mL), washed with water (50 mL), saturated NaHCO$_3$ (50 mL) and brine (100 mL). The organic layer was dried over Na$_2$SO$_4$, filtered and evaporated in vacuo. The residue was purified by flash silica chromatography using a gradient of 5-60% EtOAc in petroleum ether as mobile phase. Pure fractions were evaporated in vacuo to afford N-(2-fluoro-3-(methylsulfonyl)phenyl)-5-methyl-4-(7-nitro-1-((2-(trimethylsilyl)ethoxy)methyl)-1H-indol-3-yl)pyrimidin-2-amine (0.940 g, 69%) as a yellow solid.

$^1$H NMR (300 MHz, CDCl$_3$) δ −0.08 (s, 9H), 0.74-0.87 (m, 2H), 2.44 (s, 3H), 3.22-3.38 (m, 5 H), 5.67 (s, 2H), 7.21-7.33 (m, 2H), 7.42 (s, 1H), 7.48-7.60 (m, 1H), 7.72 (s, 1H), 7.89 (d, 1H), 8.39 (s, 1H), 8.62 (d, 1H), 8.89 (t, 1H). m/z (ES+), [M+H]$^+$=572.2.

Step 2

N-(2-fluoro-3-(methylsulfonyl)phenyl)-5-methyl-4-(7-nitro-1-((2-(trimethylsilyl)ethoxy)methyl) -1H-indol-3-yl)pyrimidin-2-amine (2.76 g, 4.83 mmol), iron (11.59 g, 207.59 mmol) and ammonium hydrochloride (11.10 g, 207.59 mmol) were dissolved in MeOH/THF/water 1:1:1 (120 mL) and stirred at 70° C. for 4 h. The reaction mixture was allowed to cool to room temperature. The solid filtered off, the filtrate poured into water (200 mL) and extracted with DCM (8×40 mL). The combined organic extracts were filtered through a phase separator and evaporated in vacuo to afford 3-(2-((2-fluoro-3-(methylsulfonyl)phenyl)amino)-5-methylpyrimidin-4-yl)-1-((2-(trimethylsilyl)ethoxy)methyl)-1H-indol-7-amine (2.52 g, 96%) as an orange gum.

$^1$H NMR (500 MHz, DMSO-d$_6$) δ −0.05 (s, 9H), 0.87-0.93 (m, 2H), 2.37 (s, 3H), 3.22 (s, 3H), 3.56-3.65 (m, 2H), 5.05 (s, 2H), 5.73 (s, 2H), 6.53 (d, 1H), 6.78 (t, 1H), 7.38 (t, 1H), 7.53 (d, 1H), 7.58 (d, 1H), 8.03 (s, 1H), 8.28 (d, 2H), 9.13 (s, 1H). m/z (ES+), [M+H]$^+$=542.3.

Intermediate 21: (S)-2-bromo-N-(3-(2-((2-fluoro-3-(methylsulfonyl)phenyl)amino)-5-methylpyrimidin-4-yl)-1H-indol-7-yl)propanamide DIPEA (0.679 mL, 3.89 mmol) was added in one portion to 3-(2-((2-fluoro-3-(methylsulfonyl)phenyl)amino)-5-methylpyrimidin-4-yl)-1H-indol-7-amine, Intermediate 11 (200 mg, 0.49 mmol) and (S)-2-bromopropanoic acid (149 mg, 0.97 mmol) in DMF (3 mL) at 25° C. The resulting solution was cooled to −40° C. and 1-propanephosphonic acid cyclic anhydride (619 mg, 0.97 mmol) added dropwise at −40° C. and stirring continued for 30 min. The reaction mixture was diluted with DCM (25 mL) and washed with brine (2×50 mL). The organic layer was dried over Na$_2$SO$_4$, filtered and evaporated in vacuo. The residue was purified by preparative TLC using MeOH/DCM 1:20 as eluent to afford (S)-2-bromo-N-(3-(2-((2-fluoro-3-(methylsulfonyl)phenyl)amino)-5-methylpyrimidin-4-yl)-1H-indol-7-yl)propanamide, (224 mg, 84%) as a brown solid.

$^1$H NMR (300 MHz, DMSO-d$_6$) δ 1.86 (d, 3H), 2.42 (s, 3H), 3.26 (s, 3H), 4.78-4.90 (m, 1H), 7.01 (t, 1H), 7.38-7.52 (m, 2H), 7.57 (t, 1H), 8.09 (d, 1H), 8.18 (d, 1H), 8.25-8.34 (m, 2H), 9.21 (s, 1H), 10.20 (s, 1H), 11.37 (s, 1H). m/z (ES+), [M+H]$^+$=546.

Intermediate 22: (R)-2-(4-methylpiperazin-1-yl)propanoic acid dihydrochloride

Step 1

(S)-methyl 2-hydroxypropanoate (250 g, 2.40 mol), DCM (1500 mL) and 2,6-dimethylpyridine (656.7 g, 6.13 mol) were placed in a 3000 mL 4-necked round-bottom flask and the mixture cooled to −78° C. Trifluoromethanesulfonic anhydride (630 g, 2.23 mol) was added dropwise with stirring at −78° C. and the resulting solution was then stirred at room temperature for 3 h.

The reaction mixture was diluted with water (1000 mL), washed with 1M HCl (3×500 mL) and brine (1×500 mL). The organic phase was dried over anhydrous Na$_2$SO$_4$, filtered and concentrated in vacuo. The residue was then added dropwise into a stirred 3000 mL 4-necked round-bottom flask, containing 1-methylpiperazine (213.3 g, 2.13 mol), DCM (800 mL), water (400 mL,) and potassium carbonate (491.3 g, 3.53 mol) at 0° C. The resulting solution was stirred at room temperature over night and was then diluted with DCM (500 mL). The resulting mixture was washed with water (1×500 mL) and brine (500 mL). The organic phase was dried over Na$_2$SO$_4$, filtrated and concentrated in vacuo. The residue was purified by preparative silica gel chromatography using a gradient of 17-50% ethyl acetate in petroleum ether as mobile phases to afford (R)- methyl 2-(4-methylpiperazin-1-yl)propanoate (226 g, 68%) as light yellow oil. m/z (ES+), [M+H]⁺=187.

Step 2

Into a 3000 mL 4-necked round-bottom flask, was placed hydrogen chloride (2000 mL, 60.34 mol, 6M/L) followed by (R)-methyl 2-(4-methylpiperazin-1-yl)propanoate (226 g, 1.21 mol). The resulting solution was stirred overnight at 100° C. and was then concentrated in vacuo. The resulting mixture diluted with acetonitrile (1000 mL) and the solid collected by filtration. The product was re-crystallized (x5) at room temperature from ethanol (1 g/20 mL) to afford (R)-2-(4-methylpiperazin-1-yl)propanoic acid dihydrochloride (124 g, 42%) as a white solid. ¹H NMR (300 MHZ, CD₃OD) δ 1.69-1.71 (d, 3H), 3.04 (s, 3H), 3.83 (m, 8H), 4.35-4.42 (m, 1H). m/z (ES+), [M+H]⁺=173.

Intermediate 23: (R)-methyl 2-((S)-3,4-dimethylpiperazin-1-yl)propanoate 2,6-dimethylpyridine (0.672 mL, 5.77 mmol) was added to a cooled -78° C. solution of (S)-methyl 2-hydroxypropanoate (500 mg, 4.81 mmol) in DCM (5 mL). The mixture was stirred for 5 min and trifluoromethanesulfonic anhydride (0.974 mL, 5.77 mmol) was then added dropwise. The reaction was stirred for 30 min, the cooling removed and the reaction mixture allowed to attain room temperature over 30 min. The solution was washed with 1M HCl (aq) (20 mL), dried with a phase separator and then added slowly to a mixture of (S)-1,2-dimethylpiperazine dihydrochloride (0.944 g, 5.05 mmol) suspended in DCM (10 mL) and a solution of potassium carbonate (1.993 g, 14.42 mmol) in water (10 mL). The reaction was stirred at room temperature for 18 h. The phases were separated. The organic phase was washed with brine (25 mL), dried with a phase separator and evaporated in vacuo to yield (R)-methyl 2-((S)-3,4-dimethylpiperazin-1-yl)propanoate (0.726 g, 75%) as a light orange oil.

¹H NMR (500 MHz, CDCl₃) δ 1.05 (d, 3H), 1.29 (d, 3H), 2.1-2.25 (m, 2H), 2.25-2.37 (m, 4H), 2.46 (t, 1H), 2.69-2.83 (m, 3H), 3.28 (q, 1H), 3.70 (s, 3H).

The procedure described above was repeated using the indicated amine to give Intermediate 24 described in Table 8:

TABLE 8

| Intermediate | Starting amine | ¹H NMR δ (500 MHz, CDCl₃) | m/z (ES+) [M + H]⁺ | Yield % |
|---|---|---|---|---|
| 24ᵃ (R)-methyl 2-((3S,5S)-3,4,5-trimethylpiperazin-1-yl)propanoate | (structure: (3S,5S)-3,4,5-trimethylpiperazine · 2 × HCl) | 1.03 (d, 6H), 1.25 (d, 3H), 2.30 (s, 3H), 2.36 - 2.46 (m, 2H), 2.60 (d, 2H), 2.76 - 2.88 (m, 2H), 3.27 (q, 1H), 3.68 (s, 3H). | NV | 91 |

Intermediate 25: (R)-2-((S)-3,4-dimethylpiperazin-1-yl)propanoic acid dihydrochloride (R)-methyl 2-((S)-3,4-dimethylpiperazin-1-yl)propanoate, Intermediate 23 (726 mg, 3.62 mmol) was stirred in 6M HCl (6 mL, 36.00 mmol) at reflux for 16 h. (The reaction had run dry). Added water (6 mL) and stirred for 2 h. The reaction was cooled to room temperature and the solvent concentrated in vacuo. The residue was suspended in acetonitrile and stirred at room temperature for 1 h. The solid was filtrated off, washed with acetonitrile and dried in vacuo to yield (R)-2-((S)-3,4-dimethylpiperazin-1-yl)propanoic acid dihydrochloride (626 mg, 66.6%) as a solid. ¹H NMR (500 MHz, D₂O) δ 1.33 (d, 3H), 1.37-1.48 (m, 3H), 2.88 (s, 3H), 3.07-3.23 (m, 1H), 3.28-3.85 (m, 7H).

The procedure described above was repeated using the indicated starting intermediate to give Intermediate 26 described in Table 9:

TABLE 9

| Intermediate | Starting intermediate | ¹H NMR δ (500 MHz, D₂O) | m/z (ES+) [M + H]⁺ | Yield % |
|---|---|---|---|---|
| 26ᵃ (R)-2-((3S,5S)-3,4,5-trimethylpiperazin-1-yl)propanoic acid dihydrochloride | 24 | 1.3-1.47 (m, 9H), 2.82 (s, 3H), 3.05-4.05 (m, 7H). | NV | 91 |

ᵃThe residue was dissolved in water/acetonitrile and freeze dried. The residual semisolid was suspended in acetonitrile and stirred for 1 h at room temperature. The solid was filtrated off, washed with acetonitrile and dried in vacuo.

Intermediate 27: (R)-2-((R)-2,4-dimethylpiperazin-1-yl)propanoic acid dihydrochloride Step 1

2,6-dimethylpyridine (0.868 mL, 7.45 mmol) was added to a cooled −78° C. solution of (S)-methyl 2-hydroxypropanoate (0.646 g, 6.21 mmol) in DCM (10 mL). The mixture was stirred for 5 min and trifluoromethanesulfonic anhydride (1.259 mL, 7.45 mmol) was then added dropwise. The reaction was stirred for 45 min, the cooling removed and the reaction mixture allowed to attain room temperature and stirred for 1 h. The solution was washed with 1M HCl (aq) (20 mL), dried with a phase separator and concentrated in vacuo. The residue was dissolved in acetonitrile (5 mL) and added to a suspension of (R)-1,3-dimethylpiperazine dihydrochloride (1.22 g, 6.52 mmol) and potassium carbonate (2.57 g, 18.63 mmol) in acetonitrile (10 mL). The reaction was heated to 60° C. under a N₂ atmosphere for 20 h. The reaction was cooled to room temperature, the solid filtered off, washed with acetonitrile and the filtrate evaporated in vacuo. The residue was dissolved in DCM (10 mL) and 8% NaHCO₃ (aq) (10 mL), shaken and the phases separated. The aqueous phase was extracted with DCM (10 mL). The combined extracts were dried with a phase separator and evaporated in vacuo to yield (R)-methyl 2-((R)-2,4-dimethylpiperazin-1-yl)propanoate (0.589 g, 47.4%, 80% de) as a pale oil ¹H NMR (500 MHz, DMSO-d₆) δ 0.94 (d, 3H), 1.06 (d, 3H), 1.82 (t, 1H), 2.03 (t, 1H), 2.10 (s, 3H), 2.37-2.55 (m, 3H), 2.55-2.67 (m, 2H), 3.61 (s, 3H), 3.66-3.74 (m, 1H). (most abundant diastereoisomer described)

Step 2

(R)-methyl 2-((R)-2,4-dimethylpiperazin-1-yl)propanoate (589 mg, 2.94 mmol) was dissolved in 6 M HCl (aq) (5 mL, 30.00 mmol) and refluxed for 18 h. The reaction was cooled to room temperature and the solvent evaporated in vacuo to a semisolid residue. Diethyl ether was added to the residue, stirred for 30 min and the solid filtrated off and dried in vacuo to yield (R)-2-((R) -2,4-dimethylpiperazin-1-yl) propanoic acid dihydrochloride (623 mg, 82%) as a pale solid.

¹H NMR (500 MHz, D₂O) δ 1.32 (d, 3H), 1.41 (d, 3H), 2.89 (s, 3H), 3.08-3.91 (m, 7H), 4.25-4.51 (m, 1H). (most abundant diastereoisomer described)

Intermediate 28: methyl 3-methoxy-2-(4-methylpiperazin-1-yl)propanoate 1-methylpiperazine (100 g, 988.4 mmol) and potassium carbonate (164 g, 1186 mmol) were slurried in dry acetonitrile (800 mL) under nitrogen. Methyl 2-bromo-3-methoxypropanoate (201 g, 988.4 mmol) was added to the slurry at 50-60° C. over a period of 40 minutes. The resulting mixture was heated under nitrogen at 61° C. for 23 hours and was then cooled to 20° C. The solid was filtered off. The filtrate was evaporated to an oily residue that was dissolved in 1M HCl (1000 mL). pH was then adjusted to 1 with 4M HCl (~300 mL). The resulting solution was extracted with DCM (200 mL). The water solution was made basic with saturated Na₂CO₃ (1000 mL) to pH 9 and extracted with DCM (2×500 mL). pH of the aqueous phase was then raised to 10-11 with sodium hydroxide and extracted with DCM (2×500 mL). The four organic phases were combined and evaporated in vacuo to yield methyl 3-methoxy-2-(4-methylpiperazin-1-yl)propanoate (181 g, 85%).

¹H NMR (400 MHz, CDCl₃) δ 2.07 (s, 3H), 2.14-2.34 (m, 4H), 2.39-2.52 (m, 4H), 3.14 (s, 3H), 3.22 (dd, 1H), 3.42 (dd, 1H), 3.48-3.56 (m, 4H).

Intermediate 29: methyl 2-(4-methylpiperazin-1-yl)propanoate

Potassium carbonate (1.987 g, 14.38 mmol) was added to methyl 2-bromopropanoate (2.041 g, 12.22 mmol) and 1-methylpiperazine (1.20 g, 11.98 mmol) in acetonitrile (20 mL) at 20° C. under nitrogen. The resulting mixture was stirred at 60° C. for 18 hours. The vibrant orange mixture was cooled to room temperature, dilute with ethyl acetate and filtered. The orange solution was concentrated in vacuo. The residue was dissolved in diethyl ether and filtered. The filtrate was evaporated in vacuo to afforded methyl 2-(4-methylpiperazin-1-yl)propanoate, (2.2 g, 99%) as an oil.

¹H NMR (400 MHz, CDCl₃) δ 1.23 (dd, 3H), 2.21 (d, 3H), 2.28-2.65 (m, 8H), 3.16-3.27 (m, 1H), 3.63 (s, 3H). m/z (ES+), [M+H]⁺=187.

The procedure described above was repeated using the indicated reactants to give Intermediates 30-44 described in Table 10:

TABLE 10

| Intermediate | 2-bromo-acetate | Amine | ¹H NMR δ (500 MHz, CDCl₃) | m/z (ES+) [M + H]⁺ | Yield % |
|---|---|---|---|---|---|
| 30ᵃ ethyl 2-(4-methylpiperazin-1-yl)butanoate | ethyl 2-bromo-butanoate | 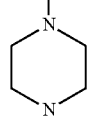 | (400 MHz) 0.91 (t, 3H), 1.28 (t, 3H), 1.58 - 1.83 (m, 2H), 2.28 (s, 3H), 2.32 - 2.75 (m, 8H), 3.05 (dd, 1H), 4.17 (q, 2H). | NV | 96 |
| 31ᵇ,ᶜ ethyl 2-((3S,5S)-3,4,5-trimethylpiperazin-1-yl)butanoate | ethyl 2-bromo-butanoate | 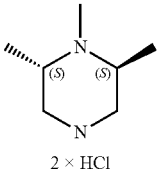 2 × HCl | 0.87 - 1.10 (m, 9H), 1.15 - 1.35 (m, 3H), 1.58 - 1.79 (m, 2H), 2.20 - 2.37 (m, 4H), 2.45 (dd, 1H), 2.55 - 2.66 (m, 1H), 2.69 - 2.89 (m, 3H), 2.90 - 3.15 (m, 1H), 3.50 (s, 2H), 4.07 - 4.24 (m, 2H). | 243 | 89 |
| 32ᵇ,ᵈ methyl 3-methoxy-2-((3S,5S)-3,4,5-trimethylpiperazin-1-yl)propanoate | methyl 2-bromo-3-methoxy-propanoate | 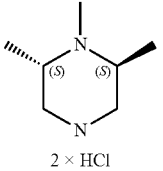 2 × HCl | 0.95 - 1.10 (m, 6H), 2.29 (s, 3H), 2.35 - 2.50 (m, 2H), 2.55 - 2.90 (m, 4H), 3.25 - 3.50 (m, 4H), 3.50 - 3.80 (m, 5H) | 245 | 88 |

TABLE 10-continued

| Intermediate | 2-bromo-acetate | Amine | ¹H NMR δ (500 MHz, CDCl₃) | m/z (ES+) [M + H]⁺ | Yield % |
|---|---|---|---|---|---|
| 33[e] (2S,6S)-tert-butyl 4-(1-methoxy-1-oxopropan-2-yl)-2,6-dimethylpiperazine-1-carboxylate | methyl 2-bromopropanoate | Boc-(2S,6S)-2,6-dimethylpiperazine | 1.23 - 1.31 (m, 9H), 1.42 - 1.51 (m, 9H), 2.33 - 2.47 (m, 2H), 2.65 (dd, 1H), 2.75 (dd, 1H), 3.27 - 3.36 (m, 1H), 3.69 (d, 3H), 3.82 - 3.92 (m, 2H). | NV | 91 |
| 34 (2R,6R)-tert-butyl 4-(1-ethoxy-1-oxobutan-2-yl)-2,6-dimethylpiperazine-1-carboxylate | ethyl 2-bromobutanoate | Boc-(2R,6R)-2,6-dimethylpiperazine | (400 MHz) 0.87 - 1.06 (m, 3H), 1.19 - 1.37 (m, 9H), 1.38 - 1.53 (m, 9H), 1.54 - 1.97 (m, 2H), 2.31 - 2.52 (m, 2H), 2.65 (dd, 1H), 2.82 (dd, 1H), 2.97 - 3.14 (m, 1H), 3.48 - 3.94 (m, 2H), 4.05 - 4.29 (m, 2H). Mixture of diastereoisomers | 329 | 91 |
| 35[a] (2R,6R)-tert-butyl 2,6-dimethylpiperazine-1-carboxylate | methyl 2-bromo-3-methoxypropanoate | Boc-(2R,6R)-2,6-dimethylpiperazine | NV | 331 | 98 |
| 36[e] methyl 2-((S)-2,4-dimethylpiperazin-1-yl)propanoate | methyl 2-bromopropanoate | (S)-2,4-dimethylpiperazine 2 × HCl | (DSMO-d₆) 0.92 - 0.99 (m, 6H), 1.06 (d, 3H), 1.17 (d, 3H), 1.64 (t, 1H), 1.78 - 1.85 (m, 1H), 1.85 - 1.92 (m, 1H), 1.99 - 2.07 (m, 1H), 2.08 - 2.12 (m, 6H), 2.26 - 2.33 (m, 1H), 2.38 - 2.44 (m, 1H), 2.44 - 2.54 (m, 3H), 2.55 - 2.65 (m, 4H), 2.73 - 2.77 (m, 1H), 3.61 (s, 6H), 3.65 - 3.77 (m, 2H). Mixture of diastereoisomers | 201 | 95 |
| 37[f] methyl 2-((S)-2,4-dimethylpiperazin-1-yl)butanoate | methyl 2-bromobutanoate | (S)-2,4-dimethylpiperazine 2 × HCl | (DMSO-d₆) 0.77 - 0.87 (m, 6H), 0.97 (t, 6H), 1.45 -1.72 (m, 5H), 1.82 - 1.97 (m, 2H), 2.09 (d, 6H), 2.22 - 2.3 (m, 1H), 2.3 - 2.38 (m, 1H), 2.38 - 2.44 (m, 1H), 2.44 - 2.66 (m, 6H), 2.66 - 2.77 (m, 3H), 3.47 (t, 1H), 3.61 (d, 6H). Mixture of diastereoisomers | 215 | 47 |

TABLE 10-continued

| Intermediate | 2-bromo-acetate | Amine | $^1$H NMR δ (500 MHz, CDCl$_3$) | m/z (ES+) [M + H]$^+$ | Yield % |
|---|---|---|---|---|---|
| 38 methyl 2-((S)-2,4-dimethylpiperazin-1-yl)-3-methoxypropanoate | methyl 2-bromo-3-methoxy-propanoate | 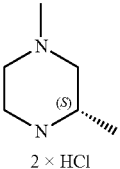 2 × HCl | NV | 231 | 30 |
| 39$^e$ methyl 2-((R)-2,4-dimethylpiperazin-1-yl)propanoate | methyl 2-bromopropanoate | 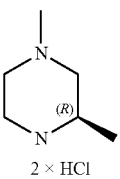 2 × HCl | (DSMO-d$_6$) 0.91 - 0.99 (m, 6H), 1.06 (d, 3H), 1.17 (d, 3H), 1.64 (t, 1H), 1.82 (t, 1H), 1.85 - 1.93 (m, 1H), 2.03 (t, 1H), 2.10 (d, 6H), 2.25 - 2.34 (m, 1H), 2.38 - 2.44 (m, 1H), 2.44 - 2.54 (m, 3H), 2.54 - 2.67 (m, 4H), 2.72 - 2.79 (m, 1H), 3.61 (s, 6H), 3.66 - 3.79 (m, 2H). Mixture of diastereoisomers | 201 | 47 |
| 40$^{e,f}$ methyl 2-((R)-2,4-dimethylpiperazin-1-yl)butanoate | methyl 2-bromo-butanoate | 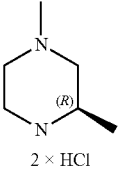 2 × HCl | (DMSO-d$_6$) 0.76 - 0.87 (m, 3H), 0.97 (t, 3H), 1.45 - 1.71 (m, 2H), 1.8 - 1.97 (m, 1H), 2.09 (d, 3H), 2.2 - 2.38 (m, 1H), 2.38 - 2.77 (m, 5H), 3.27 - 3.51 (m, 1H), 3.61 (d, 3H). Mixture of diastereoisomers | NV | 46 |
| 41$^{b,f}$ methyl 2-((R)-2,4-dimethylpiperazin-1-yl)-3-methoxypropanoate | methyl 2-bromo-3-methoxy-propanoate | 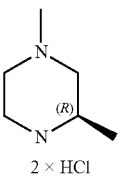 2 × HCl | (DMSO-d$_6$) 0.98 (dd, 3H), 1.61 - 1.69 (m, 1H), 1.85 - 1.93 (m, 1H), 2.09 (s, 3H), 2.31 - 2.39 (m, 1H), 2.39 - 2.68 (m, 3H), 2.71 - 2.79 (m, 1H), 3.21 - 3.24 (m, 3H), 3.43 (dd, 1H), 3.55 - 3.71 (m, 4H), 3.76 (dd, 1H). Mixture of diastereoisomers | NV | 58 |
| 42$^e$ methyl 2-(4-methyl-1,4-diazepan-1-yl)propanoate | methyl 2-bromopropanoate | 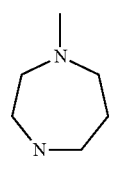 | 1.29 (d, 3H), 1.71 - 1.87 (m, 2H), 2.34 (s, 3H), 2.46 - 2.55 (m, 1H), 2.56 - 2.66 (m, 3H), 2.73 - 2.82 (m, 2H), 2.83 - 2.92 (m, 2H), 3.44 (q, 1H), 3.68 (s, 3H). | NV | 86 |
| 43$^a$ ethyl 2-(4-methyl-1,4-diazepan-1-yl)butanoate | ethyl 2-bromo-butanoate | 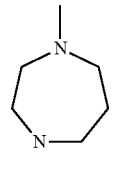 | (400 MHz) 0.95 (t, 3H), 1.27 (t, 3H), 1.55 - 1.93 (m, 4H), 2.38 (s, 3H), 2.47 - 3.00 (m, 8H), 3.13 (t, 1H), 4.15 (q, 2H). | NV | 88 |

TABLE 10-continued

| Intermediate | 2-bromo-acetate | Amine | ¹H NMR δ (500 MHz, CDCl₃) | m/z (ES+) [M + H]⁺ | Yield % |
|---|---|---|---|---|---|
| 44 methyl 3-methoxy-2-(4-methyl-1,4-diazepan-1-yl)propanoate | methyl 2-bromo-3-methoxy-propanoate | | (300 MHz) 1.76 - 1.86 (m, 2H), 2.37 (s, 3H), 2.53 - 2.57 (m, 1H), 2.62 - 2.67 (m, 3H), 2.83 - 2.99 (m, 4H), 3.37 (s, 3H), 3.53 - 3.56 (m, 1H), 3.63 - 3.70 (m, 1H), 3.71 - 3.76 (m, 4H). | 231 | 97 |

ᵃThe reaction mixture was diluted with ethyl acetate (50 mL). The reaction mixture was filtered through celite. The solvent was removed by distillation under vacuum. The reaction mixture was diluted with Et₂O (50 mL). The reaction mixture was filtered through celite. The solvent was removed by distillation under vacuum.
ᵇ3 eq. of potassium carbonate used.
ᶜThe reaction mixture was filtered. The solvent was removed under reduced pressure. The mixture was redissolved in EA and washed with HCl. The aqueous layers was combined and its pH was adjusted to 8 with Na₂CO₃. The aqueous was washed with EtOAc. The organic layers were combined and evaporated in vacuo.
ᵈThe reaction mixture was filtered and the solvent evaporated in vacuo. The residue was diluted with EtOAc (50 mL), filtered through celite and the filtrate evaporated in vacuo.
ᵉ2 eq. of potassium carbonate used.
ᶠAfter concentrating the filtrate. The residue was dissolved in DCM (150 mL), backextracted into 0.1M HCl (aq) (200 mL) and the phases separated. The aqueous phase was washed with DCM (150 mL) and then basified by addition of K₂CO₃ (s) to pH 10. The compound was then extracted with DCM (3 × 125 mL) and evaporated in vacuo.
Intermediate 45: 2-(4-methylpiperazin-1-yl)propanoic acid dihydrochloride Methyl 2-(4-methylpiperazin-1-yl)propanoate, Intermediate 29 (6.00 g, 32.21 mmol) was added dropwise to 6M HCl (70 mL, 420.00 mmol) at 0° C. The resulting mixture was stirred at 100° C. for 12 hours. The mixture was cooled to room temperature and washed with DCM (2 × 2000 mL). The aqueous phase was removed under reduced pressure to afford 2-(4-methylpiperazin-1-yl)propanoic acid dihydrochloride (6.00 g, 76%) as a white solid. ¹H NMR (400 MHz, DMSO-d₆) δ 1.54 (d, 3H), 2.83 (s, 3H), 3.47 - 3.90 (m, 8H), 4.25 - 4.45 (m, 1H), 12.21 (bs, 1H). m/z (ES+), [M + H]⁺ = 173.

The procedure described above was repeated using the indicated starting intermediate to give Intermediates 46-47 described in Table 11:

TABLE 11

| Intermediate | Starting intermediate | ¹H NMR δ (500 MHz, D₂O) | m/z (ES+) [M + H]⁺ | Yield % |
|---|---|---|---|---|
| 46ᵃ 2-((R)-2,4-dimethylpiperazin-1-yl)butanoic acid dihydrochloride | 40 | 0.80-1.01 (m, 3H), 1.17-1.48 (m, 3H), 1.6-2.03 (m, 2H), 2.87 (d, 3H), 3.05-4.15 (m, 8H). Exchangable protons not observed | NV | 87 |
| 47ᵃ 2-(4-methyl-1,4-diazepan-1-yl)propanoic acid dihydrochloride | 42 | 1.47 (d, 3H), 2.15-2.29 (m, 2H), 2.85 (s, 3H), 3.4-3.8 (m, 8H), 4.10 (q, 1H). Exchangable protons not observed | NV | 37 |

ᵃThe reaction mixture was cooled to room temperature and was then concentrated in vacuo. The residue was suspended in acetonitrile or diethyl ether and stirred at room temperature. The solid was filtered off and dried in vacuo.

Intermediate 48: Lithium 3-methoxy-2-(4-methylpiperazin-1-yl)propanoate

A solution of lithium hydroxide (0.321 g, 13.39 mmol) in water (5 mL) was added to a solution of methyl 3-methoxy-2-(4-methylpiperazin-1-yl)propanoate, Intermediate 28 (1.93 g, 8.92 mmol) in THF (5 mL). A few drops of MeOH was added until the reaction mixture became clear. The reaction was heated at 40° C. for 24 h. The organics were evaporated in vacuo. The residue diluted with water and lyophilized (x3) to yield lithium 3-methoxy-2-(4-methylpiperazin-1-yl)propanoate, (1.92 g, 103%) as a solid.

¹H NMR (500 MHz, D₂O) δ 2.06 (s, 3H), 2.48 (bs, 8H), 2.99 (t, 1H), 3.20 (s, 3H), 3.46-3.57 (m, 2H).

The procedure described above was repeated using the indicated starting intermediate to give Intermediate 49-59 described in Table 12:

TABLE 12

| Intermediate | Starting intermediate | ¹H NMR δ (500 MHz, D₂O) | m/z (ES+) [M + H]⁺ | Yield % |
|---|---|---|---|---|
| 49ᵃ,ᵇ lithium 2-((3S,5S)-3,4,5-trimethylpiperazin-1-yl)butanoate | 31 | 0.75-1.10 (m, 9H), 1.22-1.66 (m, 2H), 2.00-2.45 (m, 5H), 2.45-2.75 (m, 5H). | 215 | quant |
| 50ᵃ,ᵇ,ᶜ lithium 3-methoxy-2-((3S,5S)-3,4,5-trimethylpiperazin-1-yl)propanoate | 32 | 0.88 (dd, 6H), 2.11 (s, 3H), 2.18-2.37 (m, 2H), 2.43-2.90 (m, 4H, 3.18 (d, 3H), 3.30-3.59 (m, 3H). | NV | quant |

TABLE 12-continued

| Intermediate | Starting intermediate | $^1$H NMR δ (500 MHz, D$_2$O) | m/z (ES+) [M + H]$^+$ | Yield % |
|---|---|---|---|---|
| 51[d,e] lithium 2-((S)-2,4-dimethylpiperazin-1-yl)propanoate | 36 | (DMSO-d$_6$) 0.9-1.01 (m, 9H), 1.04 (d, 3H), 1.72 (t, 1H), 1.85-1.98 (m, 2H), 2.08 (d, 6H), 2.18-2.26 (m, 1H), 2.26-2.35 (m, 1H), 2.39-2.72 (m, 7H), 2.72-2.81 (m, 1H), 3.06-3.23 (m, 3H). mixture of diastereoisomers. | 187 | quant |
| 52[d,e] lithium 2-((S)-2,4-dimethylpiperazin-1-yl)butanoate | 37 | | 201 | quant |
| 53[a,f] lithium 2-((R)-2,4-dimethylpiperazin-1-yl)propanoate | 39 | (DMSO-d$_6$) 0.86-0.98 (m, 9H), 1.02 (d, 3H), 1.3-1.48 (m, 1H), 1.70 (t, 1H), 1.82-1.97 (m, 2H), 2.08 (d, 6H), 2.16-2.25 (m, 1H), 2.31 (t, 1H), 2.38-2.72 (m, 6H), 2.72-2.82 (m, 1H), 3.06-3.2 (m, 3H). mixture of diastereoisomers | NV | quant |
| 54[b,d,e,g] 2-((R)-2,4-dimethylpiperazin-1-yl)-3-methoxypropanoic acid dihydrochloride | 41 | | 217 | quant |
| 55 lithium 2-((3S,5S)-4-(tert-butoxycarbonyl)-3,5-dimethylpiperazin-1-yl)propanoate | 33 | 1.17 (dd, 3H), 1.2-1.31 (m, 6H), 1.36-1.47 (m, 9H), 2.40 (dd, 1H), 2.48 (dd, 1H), 2.58-2.71 (m, 2H), 2.85-3.01 (m, 1H), 3.82-3.94 (m, 2H). | NV | quant |
| 56 lithium 2-((3R,5R)-4-(tert-butoxycarbonyl)-3,5-dimethylpiperazin-1-yl)butanoate | 34 | (400 MHz) 0.67-0.89 (m, 3H), 1.05-1.22 (m, 6H), 1.26-1.38 (m, 9H), 1.38-1.76 (m, 2H), 2.31 (dd, 1H), 2.40 (dd, 1H), 2.50-2.63 (m, 1H), 2.63-2.75 (m, 1H), 3.72-3.84 (m, 2H). | 301 | 98 |
| 57[a,f,h] lithium 2-((3R,5R)-4-(tert-butoxycarbonyl)-3,5-dimethylpiperazin-1-yl)-3-methoxypropanoate | 35 | (DMSO-d$_6$) 1.11-1.23 (m, 6H), 1.37 (s, 9H), 2.33-2.49 (m, 2H), 2.60-2.75 (m, 2H), 2.82-3.10 (m, 1H), 3.25 (s, 3H), 3.32-3.62 (m, 2H), 3.63-3.75 (m, 2H). | 317 | 97 |
| 58[a,c] lithium 2-(4-methyl-1,4-diazepan-1-yl)butanoate | 43 | (400 MHz, DMSO-d$_6$) 0.87 (t, 3H), 1.35-1.53 (m, 1H), 1.57-1.80 (m, 3H), 2.25 (3 H, s), 2.40-2.65 (m, 4H), 2.70-2.93 (m, 5H). | NV | quant |
| 59[a,f] lithium 3-methoxy-2-(4-methyl-1,4-diazepan-1-yl)propanoate | 44 | (300 MHz) 1.63-1.74 (m, 2H), 2.18 (s, 3H), 2.50-2.65 (m, 4H), 2.74-2.86 (m, 4H), 3.17-3.31 (m, 4H), 3.50-3.60 (dd, 2H). | 217 | 95 |

[a] THF/MeOH 1:1 used as solvent.
[b] 3 eq. LiOH used.
[c] The reaction mixture was diluted with water (30 mL). The aqueous layer was washed with EtOAc or diethyl ether and lyophilized.
[d] MeOH used as solvent.
[e] Reaction temperature: 50° C.
[f] Reaction temperature: 60° C.
[g] 1M HCl (10 mL) was added to the reaction mixture which was then lyophilized.
[h] 2 eq. LiOH used.

Intermediate 60: (S)-methyl 3-ethoxy-2-hydroxypropanoate

Magnesium triflate (1.577 g, 4.90 mmol) was added to (S)-methyl oxirane-2-carboxylate (2.00 g, 19.59 mmol) dissolved in ethanol (10 mL) at 25° C. under nitrogen. The resulting mixture was stirred at 50° C. for 30 hours. The solvent was removed under reduced pressure. The reaction mixture was diluted with EtOAc (50 mL) and washed with brine (25 mL). The organic layer was dried over $Na_2SO_4$, filtered and evaporated in vacuo. The residue was purified by preparative TLC using EtOAc/petroleum ether 1:1, to afford (S)-methyl 3-ethoxy-2-hydroxypropanoate, (1.788 g, 61.6%) as a colourless oil.

$^1$H NMR (300 MHz, $CDCl_3$) δ 1.20 (t, 3H), 2.46 (bs, 1H), 3.45-3.67 (m, 2H), 3.74 (d, 2H), 3.83 (s, 3H), 4.19-4.41 (m, 1H). m/z (ES+), [M+H]$^+$=203.

Intermediate 61: (S)-methyl 3-ethoxy-2-(((trifluoromethyl)sulfonyl)oxy)propanoate 2,6-dimethylpyridine (1.643 mL, 14.11 mmol) was added to (S)-methyl 3-ethoxy-2-hydroxypropanoate, Intermediate 60 (1.9 g, 12.82 mmol) in DCM (30 mL) at −78° C. under nitrogen. After again sustaining full cooling, trifluoromethanesulfonic anhydride (2.341 mL, 14.11 mmol) was added dropwise via syringe pump over 1 hour. The resulting solution was stirred at −78° C. for 30 minutes followed by warming to room temperature and stirring for an additional 1 hour. The reaction mixture was diluted with DCM (100 mL), washed with 1 M HCL (75 mL) and the organic phase dried under vacuum to afford (S)-methyl 3-ethoxy-2-(((trifluoromethyl)sulfonyl)oxy)propanoate (3.30 g, 92%) as a light brown oil.

$^1$H NMR (300 MHz, $CDCl_3$) δ 1.23 (t, 3H), 3.48-3.75 (m, 2H), 3.82-4.01 (m, 3H), 4.23-4.46 (m, 2H), 5.22-5.36 (m, 1H).

Intermediate 62: (R)-methyl 3-ethoxy-2-(4-methylpiperazin-1-yl)propanoate

Potassium carbonate (3.26 g, 23.55 mmol) was dissolved in water (420 mL) and added dropwise to a solution of (S)-methyl 3-ethoxy-2-(((trifluoromethyl)sulfonyl)oxy)propanoate, Intermediate 61 (3.3 g, 11.78 mmol) and 1-methylpiperazine (1.769 g, 17.66 mmol) in DCM (15 mL) at 0° C. over a period of 5 minutes. The resulting mixture was stirred at room temperature for 15 hours. The reaction mixture was diluted with DCM (500 mL) and washed with water (100 mL) and brine (100 mL). The organic layer was dried over $Na_2SO_4$, filtered and evaporated in vacuo. The residue was purified by preparative TLC using petroleum ether/EtOAc 1:1, to afford (R)-methyl 3-ethoxy-2-(4-methylpiperazin-1-yl)propanoate (2.40 g, 88%) as a yellow oil.

$^1$H NMR (300 MHz, $CDCl_3$) δ 1.18 (t, 3H), 2.30 (s, 3H), 2.36-2.60 (m, 4H), 2.60-2.79 (m, 4H), 3.35-3.60 (m, 3H), 3.61-3.84 (m, 4H), 4.21 (q, 1H). m/z (ES+), [M+H]$^+$=231.

Intermediate 63: Lithium (R)-3-ethoxy-2-(4-methylpiperazin-1-yl)propanoate

Lithium hydroxide (204 mg, 8.51 mmol) in water (6 mL) was added to (R)-methyl 3-ethoxy-2-(4-methylpiperazin-1-yl)propanoate, Intermediate 62 (980 mg, 4.26 mmol) in THF/MeOH 1:1 (12 mL) at 25° C. The resulting solution was stirred at room temperature for 15 hours. The solvent was removed under reduced pressure. The residue was diluted with MeOH (50 mL), washed with petroleum ether (2×50 mL) and evaporated in vacuo to afford (R)-3-ethoxy-2-(4-methylpiperazin-1-yl)propanoic acid (421 mg, 45.7%).

$^1$H NMR (300 MHz, $CDCl_3$) δ 1.19 (t, 3H), 2.27 (s, 3H), 2.34-2.78 (m, 8H), 2.97-3.08 (m, 1H), 3.42-3.59 (m, 2H), 3.70 (dd, 1H), 3.76-3.87 (m, 1H). m/z (ES+), [M+H]$^+$=217.

Intermediate 64: Sodium 3-(benzyloxy)-2-(4-methylpiperazin-1-yl)propanoate

Step 1

In a round-bottomed flask equiped with a thermometer, (S)-2-amino-3-(benzyloxy)propanoic acid (3.00 g, 15.37 mmol) was dissolved in sulfuric acid (18.44 mL, 36.88 mmol) and cooled by an icebath to 0° C. A solution of sodium nitrite (1.696 g, 24.59 mmol) in water (10 mL) was added in small portions over 60 min, keeping the internal temperature below 3° C. The reaction mixture was stirred at 0° C. and slowly allowed to warm to room temperature overnight. NaOH (50%, aq, w/w, 2.8 mL) was added until pH 4. Ethyl acetate (25 mL) was then added and the reaction mixture stirred vigorously while pH was decreased to pH 3 by addition of 2 M $H_2SO_4$ (aq.). The phases were separated and the aqueous phase extracted with EtOAc (3×25 mL). The combined organic phases were dried with $MgSO_4$, filtered over a phase separator and concentrated in vacuo to afford (S)-3-(benzyloxy)-2-hydroxypropanoic acid (2.55 g, 85%, 98.0% ee).

$^1$H NMR (500 MHz, $CDCl_3$) δ 3.78 (dd, 1H), 3.83 (dd, 1H), 4.37 (t, 1H), 4.61 (d, 2H), 7.28-7.4 (m, 5H). Exchangeable protons not observed.

Step 2

Acetyl chloride (4.28 mL, 60.14 mmol) was added dropwise to icebath, 0° C., cold methanol (14 mL). The mixture was stirred at 0° C. for 5 minutes and then transferred to a solution of (S)-3-(benzyloxy)-2-hydroxypropanoic acid (2.36 g, 12.03 mmol) in methanol (14.00 mL) at 0° C. The resulting mixture was stirred at room temperature for 40 minutes. Trimethyl orthoformate (2.66 mL, 24.06 mmol) was added and the reaction mixture stirred at room temperature overnight. The reaction mixture was concentrated in vacuo. The residue was purified by automated flash chromatography on a Biotage® KP-SIL 50 g column using 50% EtOAc in heptane over 12 CV as mobile phase. The compound was detected using the wavelength of 257 nm. The product was collected and evaporated in vacuo to afford (S)-methyl 3-(benzyloxy)-2-hydroxypropanoate (1.94 g, 77%).

$^1$H NMR (500 MHz, $CDCl_3$) δ 3.04 (d, 1H), 3.76 (d, 2H), 3.79 (s, 3H), 4.31-4.36 (m, 1H), 4.54 (d, 1H), 4.61 (d, 1H), 7.27-7.37 (m, 5H).

Step 3

Triflic anhydride (1.543 mL, 9.13 mmol) was added dropwise to an icebath, 0° C., cooled solution of (S)-methyl 3-(benzyloxy)-2-hydroxypropanoate (1.92 g, 9.13 mmol) and DIPEA (1.595 mL, 9.13 mmol) in toluene (20 mL). The reaction was stirred at 25° C. for 30 minutes and then cooled to −78° C. A mixture of 1-methylpiperazine (1.013 mL, 9.13 mmol) and DIPEA (1.595 mL, 9.13 mmol) in toluene (20 mL) was added (keeping the temperature below −70° C.). The reaction mixture was stirred with cooling overnight during which time the cooling bath had reached −40° C. The reaction mixture was allowed to warm to room temperature, filtered and concentrated in vacuo. The residue was purified by automated flash chromatography on a Biotage® KP-SIL 50 g column using 66% EtOAc in heptane over 12 CV followed by 0.2 M NH₃ in MeOH over 10 CV as mobile phase. The product was detected using the wavelength 250 nm. The product fractions were collected and evaporated in vacuo to afford (R)-methyl 3-(benzyloxy)-2-(4-methylpiperazin-1-yl)propanoate (1.32 g, 66%, 96.0% ee).

$^1$H NMR (500 MHz, CDCl₃) δ 2.42 (s, 3H), 2.5-2.71 (m, 4H), 2.71-2.83 (m, 4H), 3.49 (t, 1H), 3.66-3.74 (m, 4H), 3.78 (dd, 1H), 4.53 (dd, 2H), 7.24-7.39 (m, 5H). m/z (ES+), [M+H]⁺=293.6.

Step 4

(R)-methyl 3-(benzyloxy)-2-(4-methylpiperazin-1-yl)propanoate (308 mg, 1.05 mmol) was dissolved in methanol (1.5 mL) and aq. 1M sodium hydroxide (1.05 mL) and stirred at room temperature for 16 h. Additional aq. 1M sodium hydroxide (0.2 mL) was added and the reaction mixture was stirred additional 2 h at room temperature and 3 h at 45° C. The reaction was then allowed to reach room temperature and diluted with water (5 mL) and lyophilized to give crude sodium-3-(benzyloxy)-2-(4-methylpiperazin-1-yl)propanoate (356 mg) as a solid.

$^1$H NMR (500 MHz, DMSO-d₆) δ 2.10 (s, 3H), 2.16-2.34 (m, 4H), 2.52-2.63 (m, 4H), 2.91 (dd, 1H), 3.58 (dd, 1H), 3.65 (dd, 1H), 4.39-4.48 (m, 2H), 7.23-7.28 (m, 1H), 7.28-7.36 (m, 4H). m/z (ES+), [M+H]⁺=279.2.

Intermediate 65: lithium 2-(4-methylpiperazin-1-yl)butanoate

Lithium hydroxide (0.335 g, 14.00 mmol) was added to ethyl 2-(4-methylpiperazin-1-yl)butanoate, Intermediate 30 (2.00 g, 9.33 mmol) in THF (6 mL), water (6 mL) and MeOH (1 mL) under nitrogen. The resulting suspension was stirred at 40° C. for 24 hours. The reaction mixture was concentrated in vacuo. The residue was diluted with water (10 mL), extracted with diethyl ether (2×10 mL) and the aqueous layer freeze-dried to afford lithium 2-(4-methylpiperazin-1-yl)butanoate (1.680 g, 97%) as a pale yellow solid.

$^1$H NMR (400 MHz, DMSO-d₆) δ 0.82 (t, 3H), 1.38-1.68 (m, 2H), 2.11 (s, 3H), 2.16-2.48 (m, 4H), 2.49-2.67 (m, 5H).

Intermediate 66: lithium 2-(4-(tert-butoxycarbonyl)piperazin-1-yl)propanoate

Step 1

Potassium carbonate (0.890 g, 6.44 mmol) was added to methyl 2-bromopropanoate (0.897 g, 5.37 mmol) and tert-butyl piperazine-1-carboxylate (1.00 g, 5.37 mmol) in acetonitrile (10 mL) at 20° C. under nitrogen. The resulting mixture was stirred at 60° C. for 18 hours. The reaction mixture was diluted with ethyl acetate (50 mL), filtered through celite and the filtrate evaporated in vacuo. The reaction mixture was diluted with diethyl ether (50 mL). The reaction mixture was filtered through celite and the filtrate evaporated in vacuo to afford tert-butyl 4-(1-methoxy-1-oxopropan-2-yl)piperazine-1-carboxylate (1.80 g, 123%) as a colorless oil, which was taken directly to the next step.

$^1$H NMR (300 MHz, CDCl₃) 1.33 (d, 3H), 1.46 (s, 9H), 2.45-2.75 (m, 4H), 3.25-3.60 (m, 5H), 3.72 (s, 3H). m/z (ES+), [M+H]⁺=273.

Step 2

A solution of lithium hydroxide (0.158 g, 6.61 mmol) in water (5 mL) was added to a stirred solution of tert-butyl 4-(1-methoxy-1-oxopropan-2-yl)piperazine-1-carboxylate (1.80 g, 6.61 mmol) in THF/MeOH 1:1 (10 mL). The resulting solution was stirred at 60° C. for 4 hours. The solvent was evaporated in vacuo. The residue was diluted with water (15 mL) and lyophilized to afford lithium 2-(4-(tert-butoxycarbonyl)piperazin-1-yl)propanoate, Intermediate 66(1.60 g, 91%) as white solid.

$^1$H NMR (300 MHz, D₂O) 1.13 (d, 3H), 1.35 (s, 9H), 2.40-2.55 (m, 4H), 2.89 (q, 1H), 3.26-3.47 (m, 4H). m/z (ES+), [M+H]⁺=259.

Example 1

(R)-N-(3-(2-((2-fluoro-3 -(methylsulfonyl)phenyl)amino)-5-methylpyrimidin-4-yl)-1H-indol-7-yl)-2-(4-(2-hydroxyethyl)piperazin-1-yl)propanamide Potassium carbonate (101 mg, 0.73 mmol) was added to (S)-2-bromo-N-(3-(2-((2-fluoro-3-(methylsulfonyl)phenyl)amino)-5-methylpyrimidin-4-yl)-1H-indol-7-yl)propanamide, Intermediate 21 (200 mg, 0.37 mmol) and 2-(piperazin-1-yl)ethanol in DMF (5 mL) at 0° C. under nitrogen. The resulting mixture was stirred at 0° C. for 18 hours and was then cooled to room temperature, filtered through celite and evaporated in vacuo. The product was purified by preparative achiral-HPLC on an XBridge C18 OBD column using a gradient of 41-58% acetonitrile in water (0.05% NH₃×H₂O) over 7 min with a flow of 30 mL/min. The product was collected and evaporated in vacuo to afford (R)-N-(3-(2-((2-fluoro-3-(methylsulfonyl)phenyl)amino)-5-methylpyrimidin-4-yl)-1H-indol-7-yl)-2-(4-(2-hydroxyethyl)piperazin-1-yl)propanamid (100 mg, 50%) as a white solid.

$^1$H NMR (300 MHz, CD₃OD) δ 1.47 (d, 3H), 2.47 (s, 3H), 2,85-3.43 (m, 13H), 3.45 -3.60 (m, 1H), 3.86 (t, 2H), 7.06 (t, 1H), 7.20 (d, 1H), 7.30-7.54 (m, 1H), 7.54-7.72 (m, 1H), 7.94 (s, 1H), 8.14 (d, 1H), 8.31 (s, 1H), 8.47 (bs, 1H), 8.58 (t, 1H). m/z (ES+), [M+H]⁺=596.

Example 2

(R)-N-(3-(2-((2-fluoro-3-(methylsulfonyl)phenyl)amino)-5-methylpyrimidin-4-yl)-1H-indol-7-yl)-2-(4-methylpiperazin-1-yl)propanamide DIPEA (13.9 mL, 78.08 mmol) was added in one portion to (R)-2-(4-methylpiperazin-1-yl)propanoic acid dihydrochloride, Intermediate 22 (3.34 g, 13.64 mmol) and 3-(2-((2-fluoro-3-(methylsulfonyl)phenyl)amino)-5-methylpyrimidin-4-yl)-1H-indol-7-amine, Intermediate 11 (4.00 g, 9.72 mmol) in DCM (70 mL) at 25° C. The resulting solution was stirred at 25° C. for 10 minutes. Then 1-propanephosphonic acid cyclic anhydride, T3P (50 wt %) (12.37 g, 19.44 mmol) was added dropwise at 0° C. The solution was stirred at 0° C. for 1 hour and was then concentrated in vacuo. The residue was purified by C18-flash chromatography using a gradient of 5-60% MeOH in water as mobile phase. Pure fractions were pooled and evaporated in vacuo. The residue was purified by preparative chiral-HPLC on a ChiralCel OD-H (20×250 mm) using 40% EtOH in CO₂ and a flow of 40 mL/min. The enantiomers were detected using the wavelength of 220 nm. The major isomer (isomer 1) was collected to afford (R)-N-(3-(2-((2-fluoro-3-(methylsulfonyl)phenyl)amino)-5-methylpyrimidin-4-yl)-1H-indol-7-yl)-2-(4-methylpiperazin-1-yl)propanamide (1.85 g, 30%) as a yellow solid.

$^1$H NMR (300 MHz, DMSO-$d_6$) δ 1.26 (d, 3H), 2.16 (s, 3H), 2.30-2.75 (m, 11H), 3.25 (s, 3H), 3.27-3.40 (m, 1H), 6.97 (t, 1H), 7.30-7.48 (m, 2H), 7.48-7.65 (m, 1H), 8.03 (d, 1H), 8.13 (d, 1H), 8.23-8.40 (m, 2H), 9.16 (s, 1H), 9.66 (s, 1H), 11.38 (s, 1H).
$^{19}$F NMR (282 MHz, DMSO-$d_6$) δ −121.22. m/z (ES+), [M+H]$^+$=566.

The procedure described for Example 2 was repeated using the indicated intermediates to give Examples 3-5 described in Table 17 below:

TABLE 17

| Example | Intermediates | $^1$H NMR δ (300 MHz, MeOD) | $^{19}$F NMR δ (282 MHz, MeOD) | m/z (ES+) [M + H]$^+$ | Yield % |
|---|---|---|---|---|---|
| 3$^{a,b,c}$ (R)-N-(3-(2-((3-(ethylsulfonyl)-2-fluorophenyl)amino)-5-methylpyrimidin-4-yl)-1H-indol-7-yl)-2-(4-methylpiperazin-1-yl)propanamide | 15, 22 | 1.22 (t, 3H), 1.42 (d, 3H), 2.33 (s, 3H), 2.44 (s, 3H), 2.51-2.90 (m, 8H), 3.24-3.46 (m, 3H), 7.05 (t, 1H), 7.15 (d, 1H), 7.34 (t, 1H), 7.48-7.60 (m, 1H), 7.91 (s, 1H), 8.13 (dd, 1H), 8.28 (d, 1H), 8.55-8.68 (m, 1H). Exchangeable protons not observed | −125.57 | 580 | 45 |
| 4$^{b,d,g,f}$ (R)-N-(3-(2-((3-(cyclopropylsulfonyl)-2-fluorophenyl)amino)-5-methylpyrimidin-4-yl)-1H-indol-7-yl)-2-(4-methylpiperazin-1-yl)propanamide | 16, 22 | (400 MHz) 0.99 (m, 2H), 1.16-1.27 (m, 2H), 1.40 (dd, 3H), 2.33 (m, 3H), 2.39-2.47 (m, 3H), 2.48-2.90 (m, 9H), 3.33-3.45 (m, 1H), 6.95-7.08 (m, 1H), 7.08-7.18 (m, 1H), 7.21-7.37 (m, 1H), 7.43-7.58 (m, 1H), 7.80-8.00 (m, 1H), 8.05-8.17 (m, 1H), 8.22-8.32 (m, 1H), 8.50-8.63 (m, 1H). Exchangeable protons not observed | (376 MHz) −124.95 | 592 | 25 |
| 5$^{b,d,e,f}$ (R)-N-(3-(5-chloro-2-((2-fluoro-3-(methylsulfonyl)phenyl)amino)pyrimidin-4-yl)-1H-indol-7-yl)-2-(4-methylpiperazin-1-yl)propanamide | 17, 22 | 1.40 (d, 3H), 2.36 (s, 3H), 2.50-2.90 (m, 8H), 3.12 (s, 3H), 3.40 (q, 1H), 7.01 (t, 1H), 7.14 (d, 1H), 7.40 (t, 1H), 7.63-7.72 (m, 1H), 8.12 (d, 1H), 8.34-8.44 (m, 2H), 8.51 (s, 1H). Exchangeable protons not observed | −123.46 | 586 | 18 |

$^a$T3P was added at room temperature.
$^b$The reaction mixture was evaporated to dryness and redissolved in EtOAc or DCM (50 mL), and washed with saturated NaHCO$_3$ (2 × 100 mL) and brine (2 × 100 mL). The organic layer was dried over Na$_2$SO$_4$, filtered and evaporated in vacuo. The residue was purified by preparative TLC using DCM/MeOH 10:1 or 20:1 as eluent.
$^c$The crude product was purified by preparative chiral-HPLC on a ChiralPak IA (21.2 × 150 mm, 5 μm) column using 50% hexane (0.1% DEA) in IPA and a flow of 20 mL/min. The compound was detected using a wavelength of 220 and 254 nm. The major isomer was collected and evaporated in vacuo.
$^d$Reaction time: 2 hours.
$^e$Achiral preparative HPLC purification on a XBridge C18 OBD Column using a increasing gradient of acetonitrile in water (0.05% NH$_3$xH$_2$O).
$^f$Chiral purification on a Phenomenex Lux 5u Cellulose-4, AXIA Packed, (250 × 21.2 mm, 5 μm) using 50% hexane (0.1% DEA) in EtOH/MeOH 35:15 and a flow of 20 mL/min over 30 min. The isomers were detected using a wavelength of 254 and 220 nm. The major isomer was collected and evaporated in vacuo.
$^g$Achiral preparative HPLC purification on a XBridge C18 OBD Prep Column (100 Å, 5 μm, 19 × 250 mm) using an increasing gradient of acetonitrile in water (0.1% FA) with a flow of 20 mL/min. The compounds were detected at a wavelength of 220 and 254 nm.

Example 6

(S)-N-(3-(2-((2-fluoro-3-(methylsulfonyl)phenyl)amino)-5-methylpyrimidin-4-yl)-1H-indol-7-yl)-2-(4-methylpiperazin-1-yl)propanamide Isomer 2 from the reaction of Example 2 collected and evaporated in vacuo. The residue was repurified by C18-flash chromatography using a gradient of 10-60% MeOH in water (0.1% FA). Pure fractions were evaporated in vacuo. The residue was repurified by preparative SFC on a ChiralCel OD-H (20×250 mm) using 40% EtOH in CO$_2$ and a flow of 40 mL/min. The isomers were detected using the wavelength of 220 nm. Isomer 2 was collected to afford (S)-N-(3-(2-((2-fluoro-3-(methylsulfonyl)phenyl)amino)-5-methylpyrimidin-4-yl)-1H-indol-7-yl)-2-(4-methylpiperazin-1-yl)propanamide (40 mg) as a white solid.

$^1$H NMR (400 MHz, CD$_3$OD) δ 1.41 (d, 3H), 2.33 (s, 3H), 2.43 (s, 3H), 2.49-2.87 (m, 8H), 3.15 (s, 3H), 3.39 (q, 1H), 7.02 (t, 1H), 7.14 (dd, 1H), 7.28-7.38 (m, 1H), 7.53-7.63 (m, 1H), 7.91 (s, 1H), 8.09 (dd, 1H), 8.27 (s, 1H), 8.51-8.61 (m, 1H).

$^{19}$F NMR (400 MHz, CD$_3$OD) δ −125.65. m/z (ES+), [M+H]$^+$=566.

Example 7

(R)-N-(3-(2-((2-fluoro-3-(methylsulfonyl)phenyl)amino)-5-methylpyrimidin-4-yl)-1H-indol-7-yl)-2-((3S,5S)-3,4,5-trimethylpiperazin-1-yl)propanamide

Step 1

(R)-2-((3S,5S)-3,4,5-trimethylpiperazin-1-yl)propanoic acid dihydrochloride, Intermediate 26 (113.0 mg, 0.42 mmol) and di(1H-imidazol-1-yl)methanone (127 mg, 0.78 mmol) were dissolved in DMF (3 mL) and stirred 1 h at room temperature. 3-(2-((2-fluoro-3-(methylsulfonyl)phenyl)amino)-5-methylpyrimidin-4-yl)-1-((2-(trimethylsilyl)ethoxy)methyl)-1H-indol-7-amine, Intermediate 20 (90.0 mg, 0.17 mmol) was added and the mixture was stirred at 50° C. for 16 hours. The reaction mixture was allowed to cool to room temperature, diluted with EtOAc (10.0 mL) and poured into sat. $Na_2CO_3$ (30 mL). The phases were shaken, separated and the aqueous phase extracted with EtOAc (3×15 mL). The combined organic extracts were filtered through a phase separator and evaporated in vacuo. The residue was purified by reversed phase preparative HPLC on a Waters Sunfire C18 ODB (5 μm, 19×150 mm) column using a gradient of 5-95% acetonitrile in 0.1 M $HCO_2H$ (aq), pH3. The product fractions were collected and lyophilized to afford (R)-N-(3-(2-((2-fluoro-3-(methylsulfonyl)phenyl)amino)-5-methylpyrimidin-4-yl)-1-((2-(trimethylsilyl)ethoxy)methyl)-1H-indol-7-yl)-2-((3S,5S)-3,4,5-trimethylpiperazin-1-yl)propanamide (125 mg, 104% (water present)) as a pale yellow solid.

$^1$H NMR (500 MHz, DMSO-$d_6$) δ −0.07 (s, 9H), 0.85-0.92 (m, 2H), 0.98 (d, 6H), 1.24 (d, 3H), 2.17 (s, 3H), 2.20-2.33 (m, 2H), 2.39 (s, 3H), 2.64 (d, 2H), 2.72-2.82 (m, 2H), 3.10 (q, 1H), 3.25 (s, 3H), 3.45-3.57 (m, 2H), 5.68 (d, 1H), 5.78 (d, 1H), 7.06 (t, 1H), 7.33 (d, 1H), 7.40 (t, 1H), 7.55 (t, 1H), 8.16-8.22 (m, 2H), 8.28 (t, 1H), 8.33 (s, 1H), 9.23 (s, 1H), 9.45 (s, 1H). m/z (ES+), [M+H]$^+$=724.

Step 2

(R)-N-(3-(2-((2-fluoro-3-(methylsulfonyl)phenyl)amino)-5-methylpyrimidin-4-yl)-1-((2-(trimethylsilyl)ethoxy)methyl)-1H-indol-7-yl)-2-((3S,5S)-3,4,5-trimethylpiperazin-1-yl)propanamide (97.0 mg, 0.13 mmol) was dissolved in DCM (1.3 mL) and TFA (0.25 mL, 3,37 mmol) was added. The reaction mixture was stirred at room temperature for 60 h. The reaction was diluted with DCM and poured into sat. $NaHCO_3$ (10 mL). The phases were shaken, separated and the aqueous phase extracted with DCM (3×5 mL). The organic extracts were combined, filtered through a phase separator and concentrated in vacuo. The residue was purified by chiral SFC on a Cellucoat (250×30 mm, 5 μm) column using 35% EtOH/DEA 100:0.5 in $CO_2$ at 120 bar and a flow of 140 mL/min. The product peak was detected at 270 nm. The product was collected and evaporated in vacuo. The residue was repurified by SFC on a Waters BEH (5 μm, 30×250 mm) column using a mobile phase of 20 mM MeOH/$NH_3$ in $CO_2$. The product fractions were collected and lyophilized to afford (R)-N-(3-(2-((2-fluoro-3-(methylsulfonyl)phenyl)amino)-5-methylpyrimidin-4-yl)-1H-indol-7-yl)-2-((3S,5S)-3,4,5-trimethylpiperazin-1-yl)propanamide, Example 7 (21 mg, 27%).

$^1$H NMR (600 MHz, DMSO-$d_6$) δ 0.98 (d, 6H), 1.28 (d, 3H), 2.17 (s, 3H), 2.21-2.35 (m, 2H), 2.40 (s, 3H), 2.62-2.69 (m, 2H), 2.71-2.81 (m, 2H), 3.19 (q, 1H), 3.25 (s, 3H), 6.98 (t, 1H), 7.35-7.44 (m, 2H), 7.51-7.58 (m, 1H), 8.03 (d, 1H), 8.13 (d, 1H), 8.25-8.35 (m, 2H), 9.17 (s, 1H), 9.57 (s, 1H), 11.39 (s, 1H). m/z (ES+), [M+H]$^+$=594.

Example 8

(R)-N-(3-(5-fluoro-2-((2-fluoro-3-(methylsulfonyl)phenyl)amino)pyrimidin-4-yl)-1H-indol-7-yl)-2-((3S,5S)-3,4,5-trimethylpiperazin-1-yl)propanamide (R)-2-((3S,5S)-3,4,5-trimethylpiperazin-1-yl)propanoic acid dihydrochloride, Intermediate 26 (199 mg, 0.73 mmol) and 1,1'-carbonyldiimidazole (91 mg, 0.56 mmol) were dissolved in DMF (2 mL) and stirred at room temperature for 1.5 hr. 3-(5-fluoro-2-((2-fluoro-3-(methylsulfonyl)phenyl)amino)pyrimidin-4-yl)-1H-indol-7-amine, Intermediate 18 (202 mg, 0.49 mmol) was added and the reaction heated to 60° C. for 3 h. The reaction was allowed to cool to room temperature. DCM (25 mL) was added and the organic phase washed with 8% $NaHCO_3$ (3×25 mL), dried with a phase separator and evaporated in vacuo. The residue was purified by preparative HPLC on a XBridge C18 column (10 μm, 250×50 mm) using a gradient of 25-65% acetonitrile in $H_2O$/ACN/$NH_3$ 95/5/0.2 buffer over 20 minutes with a flow of 100 mL/min. The compounds were detected by UV at 229 nm. The product was collected and lyophilized to yield (R)-N-(3-(5-fluoro-2-((2-fluoro-3-(methylsulfonyl)phenyl)amino)pyrimidin-4-yl)-1H-indol-7-yl)-2-((3S,5S)-3,4,5-trimethylpiperazin-1-yl)propanamide, Example 8 (188 mg, 65%, 99.4% de) as a white solid.

$^1$H NMR (500 MHz, DMSO-$d_6$) δ 0.98 (d, 6H), 1.28 (d, 3H), 2.17 (s, 3H), 2.2-2.34 (m, 2H), 2.65 (d, 2H), 2.7-2.81 (m, 2H), 3.19 (q, 1H), 3.27-3.34 (m, 3H), 7.03 (t, 1H), 7.38-7.5 (m, 2H), 7.58-7.66 (m, 1H), 8.14-8.25 (m, 2H), 8.28 (d, 1H), 8.43 (d, 1H), 9.45 (s, 1H), 9.62 (s, 1H), 11.60 (s, 1H). m/z (ES+), [M+H]$^+$=598.3.

Example 9

(R)-2-((3S,5S)-3,5-dimethylpiperazin-1-yl)-N-(3-(2-((2-fluoro-3-(methylsulfonyl)phenyl)amino)-5-methylpyrimidin-4-yl)-1H-indol-7-yl)propanamide, Isomer 1

Step 1

3-(2-((2-fluoro-3-(methylsulfonyl)phenyl)amino)-5-methylpyrimidin-4-yl)-1-((2-(trimethylsilyl)ethoxy)methyl)-1H-indol-7-amine, Intermediate 20 (225 mg, 0.42 mmol), lithium 2-((3S,5S)-4-(tert-butoxycarbonyl)-3,5-dimethylpiperazin-1-yl)propanoate, Intermediate 55 (143 mg, 0.50 mmol) and pyridine (0.088 mL, 1.04 mmol) were dissolved in DCM (5.0 mL) and the resulting reaction mixture was cooled to 0° C. To the cooled reaction mixture, 2,4,6-tripropyl-1,3,5,2,4,6-trioxatriphosphinane 2,4,6-trioxide, T3P (0.371 mL, 1.25 mmol) was added and the reaction mixture slowly allowed attain room temperature. The reaction was stirred for 16 h. The reaction was quenched with water, diluted with DCM (5 mL), poured into 10% $Na_2CO_3$ (30 mL), shaken, the phases separated and the aqueous phase extracted with DCM (3×10 mL). The combined organic extracts were filtered through a phase separator and evaporated in vacuo. The residue was purified by preparative HPLC on a XBridge C18 column (10 μm, 250×50 mm) using a gradient of 45-95% acetonitrile in $H_2O$/ACN/$NH_3$ 95/5/0.2 buffer over 20 minutes with a flow of 100 mL/min. The compounds were detected by UV at 270 nm. The product fractions were collected and lyophilized to afford (2S,6S)-tert-butyl 4-(1-((3-(2-((2-fluoro-3-(methylsulfonyl)phenyl)amino)-5-methylpyrimidin-4-yl)-1-((2-(trimethylsilyl)ethoxy)methyl)-1H-indol-7-yl)amino)-1-oxopropan-2-yl)-2,6-dimethylpiperazine -1-carboxylate (256 mg, 76%) as a solid.

¹H NMR (500 MHz, DMSO-d₆) δ −0.08 (d, 9H), 0.78-0.97 (m, 2H), 1.18-1.31 (m, 9H), 1.39 (s, 9H), 2.32-2.47 (m, 5H), 2.61-2.78 (m, 2H), 3.18-3.36 (m, 4H), 3.42-3.57 (m, 2H), 3.77-3.89 (m, 2H), 5.70 (d, 1H), 5.75-5.86 (m, 1H), 7.06 (t, 1H), 7.27-7.45 (m, 2H), 7.55 (t, 1H), 8.14-8.23 (m, 2H), 8.27 (t, 1H), 8.33 (s, 1H), 9.24 (s, 1H), 9.53 (d, 1H). m/z (ES+), [M+H]⁺=810.

Step 2

To (2S,6S)-tert-butyl 4-(1-((3-(2-((2-fluoro-3-(methylsulfonyl)phenyl)amino)-5-methylpyrimidin-4-yl)-1-((2-(trimethylsilyl)ethoxy)methyl)-1H-indol-7-yl)amino)-1-oxopropan -2-yl)-2,6-dimethylpiperazine-1-carboxylate (179.8 mg, 0.22 mmol) dissolved in DCM (2.0 mL) was added TFA (0.5 mL, 6.73 mmol) and the mixture stirred at room temperature for 96 h. The reaction was diluted with DCM, quenched by addition of water, poured into sat. NaHCO₃ (10 mL), shaken, the phases separated and the aqueous phase extracted with EtOAc (3×5 mL). The combined organic extracts were filtered through a phase separator and concentrated in vacuo. The isomers were separated by chiral SFC on a Chiralpak IB (250×30 mm, 5 μm) column using 30% EtOH/DEA 100:0.5 in CO₂ at 120 bar and a flow of 150 mL/min. Isomer 1 was collected and evaporated in vacuo to yield (R)-2-((3S,5S)-3,5-dimethylpiperazin-1-yl)-N-(3-(2-((2-fluoro -3-(methylsulfonyl)phenyl)amino)-5-methylpyrimidin-4-yl)-1H-indol-7-yl)propanamide Isomer 1, Example 9 (50 mg, 41%, 97% ee).

¹H NMR (500 MHz, CDCl₃) δ 1.22-1.33 (m, 6H), 1.39 (d, 3H), 2.19-2.36 (m, 2H), 2.43 (s, 3H), 2.69-2.8 (m, 2H), 3.14-3.28 (m, 4H), 3.29-3.41 (m, 2H), 6.77 (d, 1H), 7.12 (t, 1H), 7.20 -7.31 (m, 1H), 7.38 (s, 1H), 7.50 (t, 1H), 7.73 (d, 1H), 8.20 (d, 1H), 8.31 (s, 1H), 8.99 (t, 1H), 9.83 (s, 1H), 11.45 (s, 1H). One exchangeable proton not observed.

Example 10

(S)-2-((3S,5S)-3,5-dimethylpiperazin-1-yl)-N-(3-(2-((2-fluoro-3-(methylsulfonyl)phenyl)amino) -5-methylpyrimidin-4-yl)-1H-indol-7-yl)propanamide Isomer 2 from the synthesis of Example 9, step 2 was collected and evaporated in vacuo to yield (S)-2-((3S,5S)-3,5-dimethylpiperazin-1-yl)-N-(3-(2-((2-fluoro-3-(methylsulfonyl)phenyl)amino) -5-methylpyrimidin-4-yl)-1H-indol-7-yl)propanamide, Example 10 (48 mg, 36%, 90% ee).

¹H NMR (500 MHz, CDCl₃) δ 1.24-1.32 (m, 6H), 1.35 (d, 3H), 2.33-2.47 (m, 5H), 2.61-2.78 (m, 2H), 3.24 (s, 3H), 3.33-3.44 (m, 3H), 6.79 (d, 1H), 7.11 (t, 1H), 7.2-7.31 (m, 1H), 7.38 (d, 1H), 7.50 (t, 1H), 7.72 (d, 1H), 8.19 (d, 1H), 8.31 (s, 1H), 8.99 (t, 1H), 9.87 (s, 1H), 11.45 (s, 1H). One exchangeable proton not observed.

Example 11

(R)-2-((3S,5S)-3,5-dimethylpiperazin-1-yl)-N-(3-(5-fluoro-2-((2-fluoro-3-(methylsulfonyl)phenyl)amino)pyrimidin-4-yl)-1H-indol-7-yl)propanamide Isomer 1

Step 1

3-(5-fluoro-2-((2-fluoro-3-(methylsulfonyl)phenyl) amino)pyrimidin-4-yl)-1H-indol-7-amine, Intermediate 18 (318 mg, 0.77 mmol), lithium 243S,5S)-4-(tert-butoxycarbonyl)-3,5-dimethylpiperazin-1-yl)propanoate, Intermediate 55 (235 mg, 0.80 mmol) and DIPEA (0.535 mL, 3.06 mmol) were dissolved in DMF (2 mL) and 2-(3H-[1,2,3] triazolo[4,5-b]pyridin-3-yl) -1,1,3,3-tetramethylisouronium hexafluorophosphate(V) (306 mg, 0.80 mmol) added. The reaction heated to 50° C. for 1.5 hour and then cooled to ambient temperature. The reaction mixture was diluted with DCM (25 mL) and 5% Na₂CO₃ (aq) (25 mL), shaken and the phases separated. The aqueous phase was extracted with DCM (2×25 mL). The combined organic phases were dried with Na₂SO₄, filtered and evaporated in vacuo. The compound was purified by preparative HPLC on a XBridge C18 column (10 μm, 250×50 mm) using a gradient of 45-85% acetonitrile in H₂O/ACN/NH₃ 95/5/0.2 buffer over 20 minutes with a flow of 100 mL/min. The compounds were detected by UV at 230 nm. The product was collected and lyophilized. The diastereoisomers were separated using chiral SFC on a CelluCoat (250×20 mm, 5 μm) column using 35% EtOH/DEA 100:0.5 in CO₂ at 120 bar as eluent and a flow of 70 ml/min. The diastereoisomers were detected at 300 nm. The first eluting compound was collected and evaporated in vacuo as isomer 1. The residue was dissolved in acetonitrile/water and lyophilized to yield (2S,6S)-tert-butyl 4-(1-((3-(5-fluoro-2-((2-fluoro-3-(methylsulfonyl) phenyl)amino)pyrimidin-4-yl)-1H-indol-7-yl)amino)-1-oxopropan-2-yl)-2,6-dimethylpiperazine-1-carboxylate Isomer 1 (62.0 mg, 25.3%, 99.9% de) as a white solid.

¹H NMR (500 MHz, DMSO-d₆) δ 1.19-1.34 (m, 9H), 1.39 (s, 9H), 2.40 (dd, 2H), 2.75 (dd, 2H), 3.26-3.37 (m, 4H), 3.75-3.87 (m, 2H), 7.04 (t, 1H), 7.39-7.51 (m, 2H), 7.62 (t, 1H), 8.14-8.25 (m, 2H), 8.28 (d, 1H), 8.44 (d, 1H), 9.45 (s, 1H), 9.68 (s, 1H), 11.54 (s, 1H). m/z (ES+), [M+H]⁺=684.3.

Step 2

Tert-butyl (2S,6S)-4-(1-((3-(5-fluoro-2-((2-fluoro-3-(methylsulfonyl)phenyl)amino)pyrimidin-4-yl)-1H-indol-7-yl)amino)-1-oxopropan-2-yl)-2,6-dimethylpiperazine-1-carboxylate (62 mg, 0.09 mmol) was dissolved in DCM (4 mL) and TFA (1 mL, 12.98 mmol) added. The reaction stirred at room temperature for 1 h and was then evaporated in vacuo. The residue was dissolved in DCM (25 mL), 8% NaHCO₃ (aq) (25 mL), shaken and the phases separated. The aqueous phase was extracted with DCM (25 mL). The combined organic phases were dried with a phase separator and evaporated in vacuo. The residue was purified by SFC on a Waters BEH 2-EP (5 μm, 30×250 mm) column using MeOH/NH₃ 20 mM as eluent. The product was collected and evaporated in vacuo to yield (R)-2-((3S,5S)-3,5-dimethylpiperazin-1-yl)-N-(3-(5-fluoro-2-((2-fluoro-3-(methylsulfonyl)phenyl)amino)pyrimidin-4-yl)-1H-indol-7-yl)propanamide, Example 11 (32.7 mg, 61.8%).

¹H NMR (600 MHz, DMSO-d₆) δ 1.06 (d, 6H), 1.26 (d, 3H), 2.12-2.21 (m, 2H), 2.61 (dd, 2H), 3.06-3.14 (m, 2H), 3.20 (q, 1H), 3.30 (s, 3H), 7.03 (t, 1H), 7.41 (d, 1H), 7.46 (t, 1H), 7.59-7.65 (m, 1H), 8.16-8.24 (m, 2H), 8.27 (d, 1H), 8.43 (d, 1H), 9.45 (s, 1H), 9.65 (s, 1H), 11.63 (bs, 1H). m/z (ES+), [M+H]⁺=584.2.

Example 12

(S)-2-((3S,5S)-3,5-dimethylpiperazin-1-yl)-N-(3-(5-fluoro-2-((2-fluoro-3-(methylsulfonyl)phenyl)amino)pyrimidin-4-yl)-1H-indol-7-yl)propanamide Isomer 2

Step 1

The second eluting compound from the reaction of Example 11, step 1 was collected and evaporated in vacuo.

The residue was dissolved in acetonitrile/water—a white solid crashed out. The solid was filtrated, washed with acetonitrile/water and dried in vacuo to yield (2S,6S)-tert-butyl 4-(1-((3-(5-fluoro-2-((2-fluoro-3-(methylsulfonyl)phenyl)amino)pyrimidin-4-yl)-1H-indol-7-yl)amino)-1-oxopropan-2-yl)-2,6-dimethylpiperazine-1-carboxylate Isomer 2 (89 mg, 36.3%, 99.3% de) as a white solid.

$^1$H NMR (500 MHz, DMSO-$d_6$) δ 1.18-1.31 (m, 9H), 1.39 (s, 9H), 2.44 (dd, 2H), 2.69 (dd, 2H), 3.26-3.36 (m, 3H), 3.49 (q, 1H), 3.78-3.89 (m, 2H), 7.03 (t, 1H), 7.38-7.51 (m, 2H), 7.62 (t, 1H), 8.15-8.24 (m, 2H), 8.27 (d, 1H), 8.44 (d, 1H), 9.45 (s, 1H), 9.73 (s, 1H), 11.60 (s, 1H). m/z (ES+), [M+H]$^+$=684.2.

Step 2

Tert-butyl (2S,6S)-4-(1-((3-(5-fluoro-2-((2-fluoro-3-(methylsulfonyl)phenyl)amino)pyrimidin-4-yl)-1H-indol-7-yl)amino)-1-oxopropan-2-yl)-2,6-dimethylpiperazine-1-carboxylate Isomer 2 (89 mg, 0.13 mmol) was dissolved in DCM (4 mL) and TFA (1 mL, 12.98 mmol) added. The reaction was stirred at room temperature for 1 h and was then evaporated in vacuo. The residue was dissolved in DCM (25 mL), 8% NaHCO$_3$ (aq) (25 mL), shaken and the phases separated. The aqueous phase was extracted with DCM (25 mL). The combined organic phases were dried with a phase separator and evaporated in vacuo. The residue was dissolved in DMSO and purified by SFC on a Waters BEH 2-EP (5 μm, 30×250 mm) column using MeOH/NH$_3$ 20 mM as eluent. The product was collected and evaporated in vacuo to afford (S)-2-((3S,5S)-3,5-dimethylpiperazin-1-yl)-N-(3-(5-fluoro-2-((2-fluoro-3-(methylsulfonyl)phenyl)amino)pyrimidin-4-yl)-1H-indol-7-yl)propanamide, Example 12 (32.4 mg, 42.6%).

$^1$H NMR (600 MHz, DMSO-$d_6$) δ 1.06 (d, 6H), 1.19 (d, 3H), 2.21 (dd, 2H), 2.52-2.59 (m, 2H), 3.08-3.17 (m, 2H), 3.30 (s, 3H), 3.37-3.5 (m, 1H), 7.03 (t, 1H), 7.40 (d, 1H), 7.46 (t, 1H), 7.58-7.67 (m, 1H), 8.13-8.23 (m, 2H), 8.26 (d, 1H), 8.43 (d, 1H), 9.45 (s, 1H), 9.72 (s, 1H), 11.67 (bs, 1H). m/z (ES+), [M+H]$^+$=584.2.

Example 13

(S)-N-(3-(2-((2-fluoro-3-(methylsulfonyl)phenyl)amino)-5-methylpyrimidin-4-yl)-1H-indol-7-yl)-2-(4-methylpiperazin-1-yl)butanamide, DIPEA (2.54 mL, 14.58 mmol) was added to lithium 2-(4-methylpiperazin-1-yl)butanoate, Intermediate 65 (1.81 g, 9.72 mmol) and 3-(2-((2-fluoro-3-(methylsulfonyl)phenyl)amino)-5-methylpyrimidin-4-yl)-1H-indol-7-amine, Intermediate 11 (2.00 g, 4.86 mmol) in DCM (50 mL) at 15° C. under nitrogen. The mixture was stirred for 10 mins, T3P (50% in EtOAc) (6.18 g, 9.72 mmol) was added dropwise at 0° C. and the reaction stirred at 0° C. for 1 hours. The solvent was then concentrated in vacuo. The residue was purified by flash C18-flash chromatography using a gradient of 5-80% MeOH in water (NH$_4$HCO$_3$). Pure fractions were evaporated to dryness. The residue was repurified by preparative HPLC on a SunFire Prep C18 OBD column (5 μm, 30×100 mm), using decreasingly polar mixtures of water (containing % NH$_4$HCO$_3$) in acetonitrile as eluents. Fractions containing the desired compound were evaporated in vacuo. The enantiomers were separated by preparative chiral SFC on a ChiralPak AD-H (50×250 mm, 5 μm) column using 50% IPA (0.1% DEA) in CO$_2$ and a flow of 150 mL/min. The enantiomers were detected using UV at 254 nm. The first eluting isomer was collected and evaporated in vacuo to afford (S)-N-(3-(2-((2-fluoro-3-(methylsulfonyl)phenyl)amino)-5-methylpyrimidin-4-yl)-1H-indol-7-yl)-2-(4-methylpiperazin-1-yl)butanamide, Example 13 (200 mg, 7%, 96.4% ee) as a white solid.

$^1$H NMR (400 MHz, CD$_3$OD) δ 1.05 (t, 3H), 1.77-1.99 (m, 2H), 2.30 (s, 3H), 2.43 (s, 3H), 2.45-2.90 (m, 8H), 3.11-3.23 (m, 4H), 7.02 (t, 1H), 7.18 (d, 1H), 7.32 (t, 1H), 7.52-7.62 (m, 1H), 7.91 (s, 1H), 8.06-8.15 (m, 1H), 8.27 (s, 1H), 8.51-8.61 (m, 1H). exchangeable proton not observed. $^{19}$F NMR (400 MHz, CD$_3$OD) δ −125.77. m/z (ES+), [M+H]$^+$=580.

Example 14

(R)-N-(3-(2-((2-fluoro-3-(methylsulfonyl)phenyl)amino)-5-methylpyrimidin-4-yl)-1H-indol-7-yl)-2-(4-methylpiperazin-1-yl)butanamide The second eluting isomer from the synthesis of Example 13 was collected and evaporated in vacuo to afford (R)-N-(3-(2-((2-fluoro-3-(methylsulfonyl)phenyl)amino)-5-methylpyrimidin-4-yl)-1H-indol-7-yl)-2-(4-methylpiperazin-1-yl)butanamide Isomer 2, Example 14 (200 mg, 7%, 92.8% ee) as a white solid.

$^1$H NMR (400 MHz, CD$_3$OD) δ 1.05 (t, 3H), 1.77-1.99 (m, 2H), 2.30 (s, 3H), 2.43 (s, 3H), 2.45-2.95 (m, 8H), 3.11-3.23 (m, 4H), 7.02 (t, 1H), 7.18 (d, 1H), 7.33 (t, 1H), 7.52-7.62 (m, 1H), 7.91 (s, 1H), 8.06-8.15 (m, 1H), 8.27 (s, 1H), 8.51-8.61 (m, 1H). Exchangeable protons not observed. $^{19}$F NMR (400 MHz, CD$_3$OD) δ −125.72. m/z (ES+), [M+H]$^+$=580.

The procedure described above for Example 13 and 14 were repeated using the indicated intermediates to give Example 15-18 described in Table 18 below:

TABLE 18

| Example | Intermediates | $^1$H NMR δ (300 MHz, CD$_3$OD) | $^{19}$F NMR δ (400 MHz, CD$_3$OD) | m/z (ES+) [M + H]$^+$ | Yield % (% ee) |
|---|---|---|---|---|---|
| 15$^{a,b}$ (S)-N-(3-(2-((2-fluoro-3-(methylsulfonyl)phenyl)amino)-5-methylpyrimidin-4-yl)-1H-indol-7-yl)-3-methoxy-2-(4-methylpiperazin- | 11, 48 | 2.31 (s, 3H), 2.42 (s, 3H), 2.52-2.71 (m, 4H), 2.72-2.95 (m, 4H), 3.15 (s, 3H), 3.41 (s, 3H), 3.49 (t, 1H), 3.75-3.95 (m, 2H), 7.03 (t, 1H), 7.13 (d, 1H), 7.32 (t, 1H), 7.57 (t, | −125.78 | 596 | 11 (99.9) |

TABLE 18-continued

| Example | Intermediates | $^1$H NMR δ (300 MHz, CD$_3$OD) | $^{19}$F NMR δ (400 MHz, CD$_3$OD) | m/z (ES+) [M + H]$^+$ | Yield % (% ee) |
|---|---|---|---|---|---|
| 1-yl)propanamide Isomer 1 | | 1H), 7.90 (d, 1H), 8.07 (d, 1H), 8.26 (s, 1H), 8.55 (t, 1H). exchangeable protons not observed | | | |
| 16[a,b] (R)-N-(3-(2-((2-fluoro-3-(methylsulfonyl)phenyl)amino)-5-methylpyrimidin-4-yl)-1H-indol-7-yl)-3-methoxy-2-(4-methylpiperazin-1-yl)propanamide Isomer 2 | 11, 48 | 2.31 (d, 3H), 2.44 (d, 3H), 2.49-2.72 (m, 4H), 2.73-2.98 (m, 4H), 3.15 (s, 3H), 3.41 (s, 3H), 3.49 (t, 1H), 3.77-3.97 (m, 2H), 6.97-7.07 (m, 1H), 7.14 (d, 1H), 7.28-7.38 (m, 1H), 7.52-7.65 (m, 1H), 7.92 (d, 1H), 8.10 (d, 1H), 8.28 (s, 1H), 8.56 (t, 1H). exchangeable protons not observed | −125.63 | 596 | 11 (93.6) |
| 17[c,d] (R)-N-(3-(5-fluoro-2-((2-fluoro-3-(methylsulfonyl)phenyl)amino)pyrimidin-4-yl)-1H-indol-7-yl)-2-(4-methyl-1,4-diazepan-1-yl)butanamide Isomer 1 | 18, 58 | 1.08 (t, 3H), 1.74-2.05 (m, 4H), 2.47 (s, 3H), 2.75-2.90 (m, 4H), 2.92-3.12 (m, 4H), 3.22 (s, 3H), 3.26-3.42 (m, 1H), 7.07 (t, 1H), 7.26 (d, 1H), 7.36-7.48 (m, 1H), 7.60-7.71 (m, 1H), 8.18 (d, 1H), 8.25-8.36 (m, 2H), 8.37-8.49 (m, 1H). exchangeable protons not observed | (376 MHz, DMSO-d$_6$) −120.50, −147.72 | 598 | 2 (99.9) |
| 18[c,d] (S)-N-(3-(5-fluoro-2-((2-fluoro-3-(methylsulfonyl)phenyl)amino)pyrimidin-4-yl)-1H-indol-7-yl)-2-(4-methyl-1,4-diazepan-1-yl)butanamide Isomer 2 | 18, 58 | 1.08 (t, 3H), 1.74-2.05 (m, 4H), 2.51 (s, 3H), 2.75-2.90 (m, 4H), 2.92-3.14 (m, 4H), 3.22 (s, 3H), 3.26-3.42 (m, 1H), 7.08 (t, 1H), 7.26 (d, 1H), 7.42 (t, 1H), 7.60-7.73 (m, 1H), 8.18 (d, 1H), 8.25-8.36 (m, 2H), 8.37-8.49 (m, 1H). exchangeable protons not observed | (376 MHz, DMSO-d$_6$) −120.49, −147.72 | 598 | 2 (98.5) |

[a]Reversed phase HPLC purification not used.
[b]The isomers were separated by chiral SFC on a Chiralpak AS-H (50 × 250 mm, 5 μm) column using 50% MeOH (0.1% DEA) in CO$_2$ as mobile phase and a flow of 150 mL/min. The desired isomer was collected and evaporated in vacuo.
[c]DMF used as solvent.
[d]The compound was purified by preparative HPLC on a XBridge Prep C18 OBD column (5 μm, 19 × 150 mm), using decreasingly polar mixtures of water (containing 0.1% formic acid) in acetonitrile as eluents. Fractions containing the desired compound were evaporated in vacuo.
[e]The isomers were separated by preparative chiral SFC on a ChiralPak AD-H (20 × 250 mm, 5 μm) column using 4% IPA (0.1% DEA) in CO$_2$ and a flow of 40 mL/min. The isomers were detected using UV at 220 nm. The desired isomer was collected and evaporated in vacuo.

Example 19

(S)-N-(3-(2-((2-fluoro-3-(methylsulfonyl)phenyl)amino)-5-methylpyrimidin-4-yl)-1H-indol-7-yl)-2-((3S,5S)-3,4,5-trimethylpiperazin-1-yl)butanamide 3-(2-((2-fluoro-3-(methylsulfonyl)phenyl)amino)-5-methylpyrimidin-4-yl)-1H-indol-7-amine, Intermediate 11 (300 mg, 0.73 mmol) was added to lithium 2-((3S,5S)-3,4,5-trimethylpiperazin -1-yl)butanoate, Intermediate 49 (313 mg, 1.46 mmol), 1-propanephosphonic acid cyclic anhydride, T3P (50% in EtOAc) (928 mg, 1.46 mmol) and DIPEA (1.019 mL, 5.83 mmol) in DCM (1 mL) under nitrogen. The resulting solution was stirred at 25° C. for 1 hour. The reaction mixture was diluted with DCM (50 mL), washed with sat. NaHCO₃ (2×100 mL), brine (2×100 mL), dried over Na₂SO₄, filtered and evaporated in vacuo. The residue was purified by preparative TLC using DCM/MeOH 10:1. The product fractions were evaporated in vacuo. The diastereoisomers were separated by preparative chiral-HPLC on a ChiralPak-AD-H-SL001 (20×250 mm) column using 50% IPA in hexane (0.1% DEA) as mobile phase and a flow of 15 mL/min. The diastereoisomers were detected using UV at 254 and 220 nm. The first eluting isomer was collected and evaporated in vacuo to afford (S)-N-(3-(2-((2-fluoro-3-(methylsulfonyl)phenyl)amino)-5-methylpyrimidin-4-yl)-1H-indol-7-yl)-2-((3S,5S)-3,4,5-trimethylpiperazin-1-yl)butanamide, Example 19 (30 mg, 24%, 99.9% ee) as a white solid.

$^1$H NMR (300 MHz, CD$_3$OD) δ 1.07 (t, 3H), 1.17 (d, 6H), 1.75-1.98 (m, 2H), 2.39 (s, 3H), 2.45 (s, 3H), 2.52-2.70 (m, 2H), 2.89 (dd, 2H), 2.93-3.10 (m, 2H), 3.11-3.25 (m, 4H), 7.03 (t, 1H), 7.17 (dd, 1H), 7.35 (dd, 1H), 7.54-7.64 (m, 1H), 7.93 (s, 1H), 8.10 (dd, 1H), 8.29 (s, 1H), 8.52-8.62 (m, 1H). Exchangeable protons not observed.

$^{19}$F NMR (282 MHz, DMSO-d$_6$) δ −121.25. m/z (ES+), [M+H]$^+$=608.

Example 20

(R)-N-(3-(2-((2-fluoro-3-(methylsulfonyl)phenyl)amino)-5-methylpyrimidin-4-yl)-1H-indol-7-yl)-2-((3S,5S)-3,4,5-trimethylpiperazin-1-yl)butanamide The second eluting isomer from the synthesis of Example 19 was collected and evaporated in vacuo to afford (R)-N-(3-(2-((2-fluoro-3-(methylsulfonyl)phenyl)amino)-5-methylpyrimidin-4-yl)-1H-indol-7-yl)-2-((3S,5S)-3,4,5-trimethylpiperazin-1-yl)butanamide Isomer 2, Example 20 (5 mg, 4%, 90% ee) as a white solid.

$^1$H NMR (300 MHz, CD$_3$OD) δ 1.09 (t, 3H), 1.25-1.45 (m, 6H), 1.70-1.98 (m, 2H), 2.45 (s, 3H), 2.74 (s, 3H), 2.98-3.13 (m, 2H), 3.16 (s, 3H), 3.15-3.60 (m, 5H), 7.03 (t, 1H), 7.21 (d, 1H), 7.35 (t, 1H), 7.53-7.65 (m, 1H), 7.93 (s, 1H), 8.10 (d, 1H), 8.30 (s, 1H), 8.50-8.65 (m, 1H). Exchangeable protons not observed.

$^{19}$F NMR (282 MHz, DMSO-d$_6$) δ −121.11. m/z (ES+), [M+H]$^+$=608.

The procedure described above for Example 19 and Example 20 were repeated using the indicated intermediates to give Examples 21-23 described in Table 19 below:

TABLE 19

| Example | Intermediates | $^1$H NMR δ (400 MHz, DMSO-d$_6$) | $^{19}$F NMR δ (376 MHz, DMSO-d$_6$) | m/z (ES+) [M + H]$^+$ | Yield % (% ee) |
|---|---|---|---|---|---|
| 21$^{a,b}$ (S)-N-(3-(2-((2-fluoro-3-(methylsulfonyl)phenyl)amino)-5-methylpyrimidin-4-yl)-1H-indol-7-yl)-3-methoxy-2-((3S,5S)-3,4,5-trimethylpiperazin-1-yl)propanamide Isomer 1 | 11, 50 | 0.96 (d, 6H), 2.16 (s, 3H), 2.40 (s, 3H), 2.45-2.60 (m, 2H), 2.61-2.85 (m, 4H), 3.20-3.38 (m, 6H), 3.52 (t, 1H), 3.69 (dd, 1H), 3.80 (dd, 1H), 6.98 (t, 1H), 7.35-7.50 (m, 2H), 7.55 (t, 1H), 8.06 (d, 1H), 8.13 (d, 1H), 8.24-8.38 (m, 2H), 9.17 (s, 1H), 9.75 (s, 1H), 11.33 (d, 1H). | −121.20 | 624 | 12 (99.9) |
| 22$^{a,b}$ (R)-N-(3-(2-((2-fluoro-3-(methylsulfonyl)phenyl)amino)-5-methylpyrimidin-4-yl)-1H-indol-7-yl)-3-methoxy-2-((3S,5S)-3,4,5-trimethylpiperazin-1-yl)propanamide Isomer 2 | 11, 50 | 0.96 (d, 6H), 2.16 (s, 3H), 2.28-2.43 (m, 5H), 2.65-2.83 (m, 4H), 3.23-3.37 (m, 6H), 3.44 (t, 1H), 3.64 (dd, 1H), 3.79 (dd, 1H), 6.98 (t, 1H), 7.40 (t, 1H), 7.47 (d, 1H), 7.51-7.58 (m, 1H), 8.06 (d, 1H), 8.13 (d, 1H), 8.25-8.35 (m, 2H), 9.18 (s, 1H), 9.73 (s, 1H), 11.29 (s, 1H). | −121.20 | 624 | 6 (96.6) |

TABLE 19-continued

| Example | Intermediates | $^1$H NMR δ (400 MHz, DMSO-d$_6$) | $^{19}$F NMR δ (376 MHz, DMSO-d$_6$) | m/z (ES+) [M + H]$^+$ | Yield % (% ee) |
|---|---|---|---|---|---|
| 23$^c$ (S)-N-(3-(5-fluoro-2-((2-fluoro-3-(methylsulfonyl)phenyl)amino)pyrimidin-4-yl)-1H-indol-7-yl)-2-((3S,5S)-3,4,5-trimethylpiperazin-1-yl)butanamide | 18, 49 | (300 MHz) 0.84-1.05 (m, 9H), 1.57-1.85 (m, 2H), 2.15 (s, 3H), 2.29-2.47 (m, 2H), 2.57-2.80 (m, 4H), 3.14 (t, 1H), 3.25-3.40 (m, 3H), 7.03 (t, 1H), 7.40-7.68 (m, 3H), 8.10-8.35 (m, 3H), 8.44 (d, 1H), 9.46 (s, 1H), 9.73 (s, 1H), 11.52 (s, 1H). | (282 MHz) −147.70, −120.51 | 612 | 27 |

$^a$The residue was repurified by preparative HPLC on a XBridge Prep C18 OBD column (5 μm, 19 × 150 mm) eluting with a gradient of 30-55% acetonitrile in water (0.05% NH$_3$H$_2$O) and a flow of 30 mL/min. The compound was detected at a wavelength of 220 and 254 nm. Fractions containing the desired compound were collected and evaporated in vacuo.
$^b$The isomers were separated by preparative chiral-HPLC on a Phenomenex Lux 5u Cellulose-4, AXIA Packed (250 × 21.2 mm, 5 μm) column using hexane(0.1% DEA)/EtOH/MeOH 50:35:15 and a flow of 20 mL/min. The desired isomer was collected and evaporated in vacuo.
$^c$Purified by preparative HPLC on a XBridge Prep C18 OBD column (5 μm, 19 × 150 mm), using decreasingly polar mixtures of water (containing 0.1% NH$_4$HCO$_3$) in acetonitrile as eluents. Fractions containing the desired compound were evaporated in vacuo.

Example 24

(R)-N-(3-(2-((2-fluoro-3-(methylsulfonyl)phenyl)amino)-5-methylpyrimidin-4-yl)-1H-indol-7-yl)-2-(piperazin-1-yl)propanamide Step 1

DIPEA (0.637 mL, 3.65 mmol) was added to 3-(2-((2-fluoro-3-(methylsulfonyl)phenyl)amino) -5-methylpyrimidin-4-yl)-1H-indol-7-amine, Intermediate 11 (500 mg, 1.22 mmol), lithium 2-(4-(tert-butoxycarbonyl)piperazin-1-yl)propanoate, Intermediate 66 (628 mg, 2.43 mmol). EDC (349 mg, 1.82 mmol) and HOBT (279 mg, 1.82 mmol) in DMF (10 mL) under nitrogen. The resulting solution was stirred at 25° C. for 15 hours. The reaction mixture was poured into water (75 mL), extracted with EtOAc (2×75 mL). The combined organic layers were washed with brine (3×100 mL), dried over Na$_2$SO$_4$, filtered and evaporated in vacuo. The residue was purified by preparative TLC using DCM/MeOH 8:1 to afford tert-butyl 4-(1-((3-(2-((2-fluoro-3-(methylsulfonyl)phenyl)amino)-5-methylpyrimidin-4-yl)-1H-indol-7-yl)amino)-1-oxopropan-2-yl)piperazine-1-carboxylate (440 mg, 55.6%) as a pale yellow solid. m/z (ES+), [M+H]$^+$=652.

Step 2

TFA (0.050 mL, 0.64 mmol) was added dropwise to tert-butyl 4-(1-((3-(2-((2-fluoro-3-(methylsulfonyl)phenyl)amino)-5-methylpyrimidin-4-yl)-1H-indol-7-yl)amino)-1-oxopropan-2-yl)piperazine-1-carboxylate (420 mg, 0.64 mmol) in DCM (20 mL) at 20° C. . The resulting solution was stirred at 20° C. for 2 hours. The solvent was evaporated in vacuo. The residue was diluted with DCM (50 mL), washed with NaHCO$_3$ (2×50 mL) and the organics evaporated in vacuo. The enantiomers were separated by preparative chiral-HPLC on a Phenomenex Lux 5u Cellulose-4, AXIA Packed (250×21.2 mm, 5 μm) using 100% MeOH (0.1% DEA) as eluent and a flow of 20 mL/min. The isomers were detected at a wavelength of 254 and 220 nm. The first eluting isomer was collected and evaporated in vacuo to afford (R)-N-(3-(2-((2-fluoro-3-(methylsulfonyl)phenyl)amino)-5-methylpyrimidin-4-yl)-1H-indol-7-yl)-2-(piperazin-1-yl)propanamide Isomer 1, Example 24 (53 mg, 27%, 99.9% ee) as a white solid.

$^1$H NMR (400 MHz, DMSO-d$_6$) δ 1.26 (d, 3H), 2.41 (s, 3H), 2.45-2.65 (m, 4H), 2.73-2.85 (m, 4H), 3.22-3.40 (m, 4H), 6.98 (t, 1H), 7.35-7.50 (m, 2H), 7.50-7.62 (m, 1H), 8.03 (s, 1H), 8.14 (d, 1H), 8.25-8.37 (m, 2H), 9.18 (s, 1H), 9.73 (s, 1H), 11.48 (bs, 1H). One exchangeable proton not observed.

$^{19}$F NMR (376 MHz, DMSO-d$_6$) −121.21. m/z (ES+), [M+H]$^+$=552.

Example 25

(S)-N-(3-(2-((2-fluoro-3-(methylsulfonyl)phenyl)amino)-5-methylpyrimidin-4-yl)-1H-indol-7-yl)-2-(piperazin-1-yl)propanamide The second eluting isomer from the reaction of Example 24, step 2, was collected and evaporated in vacuo to afford (S)-N-(3-(2-((2-fluoro-3-(methylsulfonyl)phenyl)amino)-5-methylpyrimidin-4-yl)-1H-indol-7-yl)-2-(piperazin-1-yl)propanamide, Example 25 (47 mg, 24%, 92.6% ee) as a white solid.

$^1$H NMR (300 MHz, DMSO-d$_6$) δ 1.25 (d, 3H), 2.39 (s, 3H), 2.43-2.65 (m, 4H), 2.68-2.85 (m, 4H), 3.22-3.40 (m, 4H), 6.97 (t, 1H), 7.35-7.50 (m, 2H), 7.50-7.62 (m, 1H), 8.02 (s, 1H), 8.12 (d, 1H), 8.25-8.37 (m, 2H), 9.17 (s, 1H), 9.69 (s, 1H), 11.43 (bs, 1H). One exchangeable proton not observed.

$^{19}$F NMR (282 MHz, DMSO-d$_6$) −121.20. m/z (ES+), [M+H]$^+$=552.

Example 26

(R)-2-((3R,5R)-3,5-dimethylpiperazin-1-yl)-N-(3-(2-((2-fluoro-3-(methylsulfonyl)phenyl)amino)-5-methylpyrimidin-4-yl)-1H-indol-7-yl)butanamide Step 1

DIPEA (1.02 mL, 5.83 mmol) was added in one portion to lithium 24(3R,5R)-4-(tert -butoxycarbonyl)-3,5-dimethylpiperazin-1-yl)butanoate, Intermediate 56 (438 mg, 1.46 mmol) and 3-(2-((2-fluoro-3-(methylsulfonyl)phenyl)amino)-5-methylpyrimidin-4-yl)-1H-indol-7-amine, Intermediate 11 (300 mg, 0.73 mmol) in DCM (5 mL) at 25° C. The resulting solution was stirred at 25° C. for 10 mins. 1-propanephosphonic acid cyclic anhydride, T3P (928 mg, 1.46 mmol) was added dropwise at 0° C. and the reaction stirred for 1 hour. The reaction mixture was concentrated in vacuo. The residue was purified by preparative TLC using MeOH/DCM 1:10 to afford (2R,6R)-tert-butyl 4-(1-((3-(2-((2-fluoro-3-(methylsulfonyl)phenyl)amino)-5-methylpyrimidin-4-yl)-1H-indol-7-yl)amino)-1-oxobutan-2-yl)-2,6-dimethylpiperazine-1-carboxylate (200 mg, 39.5%) as a yellow solid.

$^1$H NMR (400 MHz, CD$_3$OD) δ 1.03-1.11 (m, 3H), 1.18-1.52 (m, 15H), 1.81-1.92 (m, 2H), 2.35-2.80 (m, 5H), 2.82-2.93 (m, 2H), 3.15 (s, 3H), 3.75-3.99 (m, 2H), 4.08-4.21 (m, 1H), 7.02 (t, 1H), 7.18 (dd, 1H), 7.32 (t, 1H), 7.52-7.61 (m, 1H), 7.91 (d, 1H), 8.09 (d, 1H), 8.26 (s, 1H), 8.51-8.61 (m, 1H). Exchangeable protons not observed. Mixture of diastereoisomers. m/z (ES+), [M+H]$^+$=694.

Step 2

TFA (5 mL, 64.90 mmol) was added to (2R,6R)-tert-butyl 4-(1-((3-(2-((2-fluoro-3-(methylsulfonyl)phenyl)amino)-5-methylpyrimidin-4-yl)-1H-indol-7-yl)amino)-1-oxobutan-2-yl)-2,6-dimethylpiperazine-1-carboxylate (370 mg, 0.53 mmol) in DCM (20 mL) at 25° C. The resulting mixture was stirred at room temperature for 2 hours. The solvent was concentrated in vacuo. The residue was purified by reversed phase preparative chromatography on a XBridge Prep C18 OBD column (5 μm, 19×150 mm) using a gradient of 30-50% acetonitrile in water (0.03% NH$_3$H$_2$O) over 7 min with a flow of 30 mL/min. The compounds were detected using a wavelength of 220 and 254 nm. The diastereoisomers were separated by preparative chiral -HPLC on a ChiralPak-AD-H-SL001 (20×250 mm) using 50% EtOH in hexane (0.1% DEA) over 85 min and a flow of 15 mL/min. The compounds were detected using a wavelength of 220 and 254 nm. The first eluting compound was collected and evaporated in vacuo to afford R-2-((3R,5R)-3,5-dimethylpiperazin-1-yl)-N-(3-(2-((2-fluoro-3-(methylsulfonyl)phenyl)amino)-5-methylpyrimidin-4-yl)-1H-indol-7-yl)butanamide, Example 26 (78 mg, 28%, 99.0% ee).

$^1$H NMR (400 MHz, CD$_3$OD) δ 1.09 (t, 3H), 1.41 (d, 6H), 1.80-2.00 (m, 2H), 2.44 (s, 3H), 2.77 (dd, 2H), 3.07 (dd, 2H), 3.15 (s, 3H), 3.28-3.40 (m, 1H), 3.55-3.72 (m, 2H), 7.02 (t, 1H), 7.23 (d, 1H), 7.33 (t, 1H), 7.53-7.62 (m, 1H), 7.92 (d, 1H), 8.05-8.13 (m, 1H), 8.28 (s, 1H), 8.40-8.49 (m, 2H), 8.50-8.60 (m, 1H).

$^{19}$F NMR (376 MHz, CD$_3$OD) δ -125.59. m/z (ES+), [M+H]$^+$=594.

Example 27

(S)-2-((3R,5R)-3,5-dimethylpiperazin-1-yl)-N-(3-(2-((2-fluoro-3-(methylsulfonyl)phenyl)amino)-5-methylpyrimidin-4-yl)-1H-indol-7-yl)butanamide The second eluting compound from the reaction of Example 26, Step 2 was collected and evaporated in vacuo to afford (S)-2-((3R,5R)-3,5-dimethylpiperazin-1-yl)-N-(3-(2-((2-fluoro-3-(methylsulfonyl)phenyl)amino)-5-methylpyrimidin-4-yl)-1H-indol-7-yl)butanamide Example 27 (30.0 mg, 13%, 99.9% ee) as a white solid.

$^1$H NMR (400 MHz, CD$_3$OD) δ 1.07 (t, 3H), 1.22 (d, 6H), 1.80-1.93 (m, 2H), 2.40-2.58 (m, 5H), 2.81 (dd, 2H), 3.07-3.18 (m, 4H), 3.19-3.29 (m, 2H), 7.03 (t, 1H), 7.19 (d, 1H), 7.35 (t, 1H), 7.53-7.63 (m, 1H), 7.94 (s, 1H), 8.05-8.15 (m, 1H), 8.29 (s, 1H), 8.52-8.62 (m, 1H). Exchangeable protons not observed. m/z (ES+), [M+H]$^+$=594.

The procedure described above for Example 26 and 27 were repeated using the indicated intermediates to give Examples 28-33 described in Table 20 below:

TABLE 20

| Example | Intermediates | $^1$H NMR δ (400 MHz, DMSO-d$_6$) | $^{19}$F NMR δ (282 MHz, DMSO-d$_6$) | m/z (ES+) [M + H]$^+$ | Yield % (% ee) |
|---|---|---|---|---|---|
| 28$^{a,b}$ (S)-2-((3R,5R)-3,5-dimethylpiperazin-1-yl)-N-(3-(2-((2-fluoro-3-(methylsulfonyl)phenyl)amino)-5-methylpyrimidin-4-yl)-1H-indol-7-yl)-3-methoxypropanamide Isomer 1 | 11, 57 | 1.05 (d, 6H), 2.20-2.33 (m, 2H), 2.49 (s, 3H), 2.65-2.78 (m, 2H), 3.00-3.20 (m, 2H), 3.21-3.50 (m, 7H), 3.57-3.70 (m, 1H), 3.72-3.86 (m, 1H), 6.98 (t, 1H), 7.33-7.60 (m, 3H), 8.07 (d, 1H), 8.14 (d, 1H), 8.22-8.37 (m, 2H), 9.19 (s, 1H), 9.72 (s, 1H), 11.31 (s, 1H). one exchangeable proton not observed. | -121.19 | 610 | 6 (99.9) |
| 29$^{a,b}$ (R)-2-((3R,5R)-3,5-dimethylpiperazin-1-yl)-N-(3-(2-((2-fluoro-3-(methylsulfonyl) | 11, 57 | 1.04 (d, 6H), 2.32-2.45 (m, 5H), 2.58-2.71 (m, 2H), 3.00-3.20 (m, 2H), 3.21-3.45 (m, 6H), 3.52 (t, 1H), | -121.19 | 610 | 6 (99.9) |

TABLE 20-continued

| Example | Intermediates | $^1$H NMR δ (400 MHz, DMSO-$d_6$) | $^{19}$F NMR δ (282 MHz, DMSO-$d_6$) | m/z (ES+) [M + H]$^+$ | Yield % (% ee) |
|---|---|---|---|---|---|
| phenyl)amino)-5-methylpyrimidin-4-yl)-1H-indol-7-yl)-3-methoxypropanamide Isomer 2 | | 3.62-3.74 (m, 1H), 3.75-3.88 (m, 1H), 6.98 (t, 1H), 7.33-7.49 (m, 2H), 7.50-7.51 (m, 1H), 8.06 (d, 1H), 8.14 (d, 1H), 8.22-8.38 (m, 2H), 9.18 (s, 1H), 9.76 (s, 1H), 11.35 (s, 1H). one exchangeable proton not observed. | | | |
| 30$^{a,c,d}$ (S)-2-((3R,5R)-3,5-dimethylpiperazin-1-yl)-N-(3-(5-fluoro-2-((2-fluoro-3-(methylsulfonyl)phenyl)amino)pyrimidin-4-yl)-1H-indol-7-yl)butanamide Isomer 1 | 18, 56 | (300 MHz, CD$_3$OD) 1.06 (t, 3H), 1.20 (d, 6H), 1.76-1.95 (m, 2H), 2.33-2.55 (m, 2H), 2.79 (dd, 2H), 3.05-3.45 (m, 6H), 7.07 (t, 1H), 7.19 (d, 1H), 7.42 (t, 1H), 7.63-7.75 (m, 1H), 8.18 (d, 1H), 8.25-8.38 (m, 2H), 8.39-8.50 (m, 1H). Exchangeable protons not observed. | (CD$_3$OD) −148.96, −124.64 | 598 | 6 (99.9) |
| 31$^{a,c,d}$ (R)-2-((3R,5R)-3,5-dimethylpiperazin-1-yl)-N-(3-(5-fluoro-2-((2-fluoro-3-(methylsulfonyl)phenyl)amino)pyrimidin-4-yl)-1H-indol-7-yl)butanamide Isomer 2 | 18, 56 | (300 MHz, CD$_3$OD) 1.07 (t, 3H), 1.21 (d, 6H), 1.73-1.98 (m, 2H), 2.45 (dd, 2H), 2.79 (dd, 2H), 3.13-3.40 (m, 6H), 7.07 (t, 1H), 7.18 (dd, 1H), 7.35-7.48 (m, 1H), 7.58-7.72 (m, 1H), 8.17 (d, 1H), 8.23-8.37 (m, 2H), 8.38-8.50 (m, 1H). Exchangeable protons not observed. | −147.73, −120.51 | 598 | 24 (99.8) |
| 32$^{a,b,e}$ (S)-2-((3R,5R)-3,5-dimethylpiperazin-1-yl)-N-(3-(5-fluoro-2-((2-fluoro-3-(methylsulfonyl)phenyl)amino)pyrimidin-4-yl)-1H-indol-7-yl)-3-methoxypropanamide Isomer 1 | 18, 57 | (300 MHz, CD$_3$OD) 1.29 (d, 6H), 2.53 (dd, 2H), 2.96 (dd, 2H), 3.21 (s, 3H), 3.28-3.55 (m, 6H), 3.81 (dd, 1H), 3.91 (dd, 1H), 7.07 (t, 1H), 7.14 (d, 2H), 7.40 (t, 1H), 7.58-7.75 (m, 1H), 8.16 (d, 1H), 8.14-8.50 (m, 2H). Exchangeable protons not observed. | (376 MHz) −147.73, −120.49 | 614 | 12 (99.9) |
| 33$^{a,b,e}$ (R)-2-((3R,5R)-3,5-dimethylpiperazin- | 18, 57 | (300 MHz, CD$_3$OD) 1.39 (d, 6H), 2.86 (dd, 2H), 3.04 (dd, | (376 MHz) −147.74, −120.53 | 614 | 13 (99.9) |

TABLE 20-continued

| Example | Intermediates | ¹H NMR δ (400 MHz, DMSO-$d_6$) | ¹⁹F NMR δ (282 MHz, DMSO-$d_6$) | m/z (ES+) [M + H]⁺ | Yield % (% ee) |
|---|---|---|---|---|---|
| 1-yl)-N-(3-(5-fluoro-2-((2-fluoro-3-(methylsulfonyl)phenyl)amino)pyrimidin-4-yl)-1H-indol-7-yl)-3-methoxypropanamide Isomer 2 | | 2H), 3.22 (s, 3H), 3.43 (s, 3H), 3.55-3.78 (m, 3H), 3.80-4.05 (m, 2H), 7.07 (t, 1H), 7.15 (dd, 1H), 7.41 (t, 1H), 7.60-7.75 (m, 1H), 8.16 (d, 1H), 8.25-8.52 (m, 3H). Exchangeable protons not observed. | | | |

<sup>a</sup>The reaction mixture from step 1 was diluted with EtOAc or DCM (300 mL), washed with water (150 mL) and brine (125 mL). The organic layer was dried over $Na_2SO_4$, filtered and evaporated in vacuo. The residue was purified by preparative TLC using DCM/MeOH 20:1 or 30:1.
<sup>b</sup>The isomers were separated by preparative chiral-HPLC on a Phenomenex Lux 5u Cellulose-4, AXIA Packed (250 × 21.2 mm, 5 μm) column using hexane:EtOH:MeOH 50:35:15 as mobile phase and a flow of 20 mL/min. The compounds were detected using a wavelength of 254 and 220 nm. The desired isomer was collected and evaporated in vacuo.
<sup>c</sup>Step 2: Purified by preparative HPLC on a XBridge Shield RP18 OBD Column (5 μm, 19 × 150 mm) using 15-45% acetonitrile in water (10 mmol/L $NH_4HCO_3$) as mobile phase and a flow of 25 mL/min. The compounds were detected using a wavelength of 254 and 220 nm. Fractions containing the desired compound were evaporated in vacuo.
<sup>d</sup>The isomers were separated by preparative chiral-HPLC on a (R,R)-WHELK-O1-Kromasil (50 × 250 mm, 5 μm) using 100% MeOH (0.1% DEA) as mobile phase and a flow of 20 mL/min over 21 min. The isomers were detected using a wavelength of 254 and 220 nm. The desired isomer was collected and evaporated in vacuo.
<sup>e</sup>Step 2: Purification by preparative HPLC on a XBridge Prep C18 OBD column (5 μm, 19 × 150 mm) using decreasingly polar mixtures of water (containing 0.05% Formic acid) in acetonitrile as eluents. Fractions containing the desired compound were evaporated in vacuo.

Example 34

(S)-N-(3-(5-fluoro-2-((2-fluoro-3-(methylsulfonyl)phenyl)amino)pyrimidin-4-yl)-1H-indol-7-yl)-3-methoxy-2-(4-methylpiperazin-1-yl)propanamide Lithium 3-methoxy-2-(4-methylpiperazin-1-yl)propanoate, Intermediate 48 (430 mg, 2.06 mmol), 2-(3H-[1,2,3]triazolo[4,5-b]pyridin-3-yl)-1,1,3,3-tetramethylisouronium hexafluorophosphate(V) (785 mg, 2.06 mmol) and DIPEA (1.068 mL, 6.11 mmol) and were dissolved in DMF (10 mL) stirred at room temperature for 5 min and 3-(5-fluoro-2-((2-fluoro-3-(methylsulfonyl)phenyl)amino)pyrimidin-4-yl)-1H-indol-7-amine, Intermediate 18 (635 mg, 1.53 mmol) was then added. The reaction was stirred at room temperature for 2 h then diluted with DCM (75 mL) and 5% $Na_2CO_3$ (aq) (50 mL), shaken and the phases separated. The aqueous phase was extracted with DCM (2×50 mL). The combined organic phases were dried with a phase separator, filtered and evaporated in vacuo. The compound was purified by preparative HPLC on a XBridge C18 column (10 μm, 250×50 mm) using a gradient of 15-65% acetonitrile in $H_2O/ACN/NH_3$ 95/5/0.2 buffer over 20 minutes with a flow of 100 mL/min. The compounds were detected by UV at 220 nm. The product peaks were collected and lyophilized. Then crystallized from acetonitrile and the solid was collected by filtration, washed with minimal amount of acetonitrile and dried in vacuo. The enantiomers were separated by chiral—SFC on a CelluCoat (250×30 mm, 5μm) column using 25% IPA/DEA 100:0.5 in $CO_2$ at 150 bar with a flow of 140 mL/min. The enantiomers were detected by UV at 270 nm. The first eluting enantiomer was collected and lyophilized to afford N-(3-(5-fluoro-2-((2-fluoro-3-(methylsulfonyl)phenyl)amino)pyrimidin-4-yl)-1H-indol-7-yl)-3-methoxy-2-(4-methylpiperazin -1-yl)propanamide, Example 34 (213 mg, 23%, 99.9% ee) as a white solid.

¹H NMR (500 MHz, DMSO-$d_6$) δ 2.14 (s, 3H), 2.24-2.44 (m, 4H), 2.56-2.67 (m, 2H), 2.68-2.8 (m, 2H), 3.24-3.35 (m, 6H), 3.50 (t, 1H), 3.67 (dd, 1H), 3.79 (dd, 1H), 7.04 (t, 1H), 7.41-7.55 (m, 2H), 7.62 (t, 1H), 8.19 (t, 1H), 8.22-8.32 (m, 2H), 8.44 (d, 1H), 9.46 (s, 1H), 9.84 (s, 1H), 11.47 (s, 1H). m/z (ES+), [M+H]⁺=600.2.

Example 35

(R)-N-(3-(5-fluoro-2-(2-fluoro-3-(methylsulfonyl)phenylamino)pyrimidin-4-yl)-1H-indol-7-yl) -3-methoxy-2-(4-methylpiperazin-1-yl)propanamide The second eluting enantiomer from Example 34 was collected and lyophilized. The residue was recrystallized by stirring a suspension in EtOH/water (3:1) (5 mL), heated to 70° C. using an oilbath and a seed added. The oil bath temperature was then set to 23° C. and the suspension slowly allowed to attain room temperature. Stirring was continued for 5 days to give a milky like slurry containing short needle shaped crystals with a mix in of longer needle shaped crystals. The suspension was heated to 70° C. with stirring, the heating and stirring was then turned off and the mixture allowed to slowly reach room temperature (2x). Only nice long needle shaped crystals. The suspension was left standing for one more week without stirring. The solid was filtrated off and dried in vacuo at 40° C. to afford (R)-N-(3-(5-fluoro-2-(2-fluoro-3-(methylsulfonyl)phenylamino)pyrimidin-4-yl)-1H-indol-7-yl)-3-methoxy-2-(4-methylpiperazin -1-yl)propanamide, Example 35 (186 mg, 20%, 99.4% ee) as white needle shaped crystals.

¹H NMR (500 MHz, DMSO-$d_6$) δ 2.14 (s, 3H), 2.23-2.45 (m, 4H), 2.57-2.67 (m, 2H), 2.69-2.78 (m, 2H), 3.26-3.34 (m, 6H), 3.50 (t, 1H), 3.67 (dd, 1H), 3.79 (dd, 1H), 7.03 (t, 1H), 7.4-7.55 (m, 2H), 7.62 (t, 1H), 8.13-8.33 (m, 3H), 8.44 (d, 1H), 9.46 (s, 1H), 9.84 (s, 1H), 11.48 (s, 1H). ¹⁹F NMR (470 MHz, DMSO-$d_6$) δ −120.52, −147.75. m/z (ES+), [M+H]⁺=600.5.

A sample of Example 35 was mounted on single silicon crystal (SSC) wafer mount and powder X-ray diffraction was recorded with a Theta-Theta PANalytical X'Pert PRO (wavelength of X-rays 1.5418 Å nickel-filtered Cu radiation, Voltage 45 kV, filament emission 40 mA). Automatic variable divergence and anitscatter slits were used and the samples were rotated during measurement. Samples were scanned from 2-50° 2Theta using a 0.013° step width and a 233 seconds step measurement time using a PIXCEL detector (active length 3.35° 2Theta). Characteristic peak positions of the crystals are listed in Table 21 below (determined by)(RFD) and shown in FIG. 1:

TABLE 21

| Five most characteristic peaks of Example 35: °2-theta |
|---|
| 7.6 |
| 12.7 |
| 14.8 |
| 19.3 |
| 25.5 |

A person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996).

Example 36

(S)-N-(3-(24(2-fluoro-3-(methylsulfonyl)phenyl)amino)-5-methylpyrimidin-4-yl)-1H-indol-7-yl)-2-(4-methyl-1,4-diazepan-1-yl)butanamide HATU((1-[Bis(dimethylamino)methylene]-1H-1,2,3-triazolo[4,5-b]pyridinium 3-oxid hexafluorophosphate) (832 mg, 2.19 mmol) was added to 3-(2-((2-fluoro-3-(methylsulfonyl)phenyl)amino)-5-methylpyrimidin-4-yl)-1H-indol-7-amine, Intermediate 11 (300 mg, 0.73 mmol), lithium 2-(4-methyl-1,4-diazepan-1-yl)butanoate, Intermediate 58 (511 mg, 2.55 mmol) and DIPEA (1.273 mL, 7.29 mmol) in DMF (1 mL). The resulting solution was stirred at 25° C. for 16 hours. The crude product was purified by reversed phase preparative chromatography on a XBridge Prep C18 OBD column (5 μm, 19×150 mm) using a gradient of 30-55% acetonitrile in water (0.03% $NH_3H_2O$) as eluent and a flow of 30 mL/min. The compound was detected using a wavelength of 220 and 254 nm. The enantiomers were separated by chiral SFC on a (R,R)WHELK-01 5/100 Kromasil (250× 21.1 mm) column using 50% MeOH/acetonitrile 1:1 (0.1% DEA) in $CO_2$ and a flow of 50 mL/min;. The compounds were detected using a wavelength of 220 nm. The first eluting isomer was collected and evaporated in vacuo to afford (S)-N-(3-(2-((2-fluoro-3-(methylsulfonyl)phenyl)amino)-5-methylpyrimidin-4-yl)-1H-indol-7-yl)-2-(4-methyl-1,4-diazepan-1-yl)butanamide, Example 36 (40 mg, 6%, 99.9% ee).

$^1$H NMR (400 MHz, $CD_3OD$) δ 1.08 (t, 3H), 1.72-2.02 (m, 4H), 2.38-2.50 (m, 6H), 2.70-2.85 (m, 4H), 2.88-3.10 (m, 4H), 3.15 (s, 3H), 3.27-3.40 (m, 1H), 7.02 (t, 1H), 7.26 (d, 1H), 7.34 (t, 1H), 7.52-7.65 (m, 1H), 7.92 (s, 1H), 8.08, (d, 1H), 8.28 (s, 1H), 8.52-8.63 (m, 1H). Exchangeable protons not observed.

$^{19}$F NMR (376 MHz, $CD_3OD$) δ −125.64. m/z (ES+), $[M+H]^+$=594.

Example 37

(R)-N-(3-(2-((2-fluoro-3-(methylsulfonyl)phenyl)amino)-5-methylpyrimidin-4-yl)-1H-indol-7-yl)-2-(4-methyl-1,4-diazepan-1-yl)butanamide The second eluting isomer from the synthesis of Example 36 was collected and evaporated in vacuo to afford (R)-N-(3-(2-((2-fluoro-3-(methylsulfonyl)phenyl)amino)-5-methylpyrimidin-4-yl)-1H-indol-7-yl)-2-(4-methyl-1,4-diazepan-1-yl)butanamide, (40 mg, 6%, 99.9% ee).

$^1$H NMR (400 MHz, $CD_3OD$) δ 1.07 (t, 3H), 1.73-2.03 (m, 4H), 2.39-2.49 (m, 6H), 2.68-2.83 (m, 4H), 2.88-3.09 (m, 4H), 3.15 (s, 3H), 3.27-3.40 (m, 1H), 7.02 (t, 1H), 7.25 (d, 1H), 7.34 (t, 1H), 7.52-7.62 (m, 1H), 7.92 (s, 1H), 8.08, (d, 1H), 8.28 (s, 1H), 8.50-8.63 (m, 1H). Exchangeable protons not observed. $^{19}$F NMR (376 MHz, $CD_3OD$) δ −125.70. m/z (ES+), $[M+H]^+$=594.

The procedure described above for Examples 36 and 37 were repeated using the indicated intermediates to give Example 38-45 described in Table 22 below:

TABLE 22

| Example | Intermediates | $^1$H NMR δ (400 MHz, $CD_3OD$) | $^{19}$F NMR δ (376 MHz, $CD_3OD$) | m/z (ES+) $[M + H]^+$ | Yield % (% ee) |
|---|---|---|---|---|---|
| 38[a,c,d] (R)-N-(3-(5-fluoro-2-((2-fluoro-3-(methylsulfonyl)phenyl)amino)pyrimidin-4-yl)-1H-indol-7-yl)-2-(4-methylpiperazin-1-yl)butanamide Isomer 1 | 18, 65 | (300 MHz, DMSO-$d_6$) 0.94 (t, 3H), 1.60-1.85 (m, 2H), 2.14 (s, 3H), 2.22-2.45 (m, 4H), 2.47-2.75 (m, 4H), 3.10-3.50 (m, 4H), 7.02 (t, 1H), 7.46 (t, 1H), 7.53-7.68 (m, 2H), 8.12-8.35 (m, 3H), 8.43 (d, 1H), 9.45 (s, 1H), 9.86 (s, 1H), 11.65 (bs, 1H). | (282 MHz, DMSO-$d_6$) −147.72, −120.51 | 584 | 27 (99.9) |

TABLE 22-continued

| Example | Intermediates | ¹H NMR δ (400 MHz, CD₃OD) | ¹⁹F NMR δ (376 MHz, CD₃OD) | m/z (ES+) [M + H]⁺ | Yield % (% ee) |
|---|---|---|---|---|---|
| 39[a,c,d] (S)-N-(3-(5-fluoro-2-((2-fluoro-3-(methylsulfonyl)phenyl)amino)pyrimidin-4-yl)-1H-indol-7-yl)-2-(4-methylpiperazin-1-yl)butanamide Isomer 2 | 18, 65 | (300 MHz, DMSO-d₆) 0.94 (t, 3H), 1.60-1.87 (m, 2H), 2.13 (s, 3H), 2.22-2.45 (m, 4H), 2.47-2.75 (m, 4H), 3.16 (dd, 1H), 3.32(s, 3H), 7.03 (t, 1H), 7.46 (t, 1H), 7.51-7.68 (m, 2H), 8.10-8.35 (m, 3H), 8.43 (d, 1H), 9.46 (s, 1H), 9.78 (s, 1H), 11.48 (bs, 1H). | (282 MHz, DMSO-d₆) −147.72, −120.54 | 584 | 16 (99.8) |
| 40[a,e,c,d] (S)-N-(3-(5-fluoro-2-((2-fluoro-3-(methylsulfonyl)phenyl)amino)pyrimidin-4-yl)-1H-indol-7-yl)-3-methoxy-2-((3S,5S)-3,4,5-trimethylpiperazin-1-yl)propanamide Isomer 1 | 18, 50 | (300 MHz) 1.15 (d, 6H), 2.35 (s, 3H), 2.63-2.79 (m, 2H), 2.80-3.07 (m, 4H), 3.22 (s, 3H), 3.41 (s, 3H), 3.55 (t, 1H), 3.83 (dd, 1H), 3.94 (dd, 1H), 7.00-7.17 (m, 2H), 7.42 (t, 1H), 7.60-7.73 (m, 1H), 8.17 (d, 1H), 8.23-8.38 (m, 2H), 8.39-8.48 (m, 1H). Exchangeable protons not observed | (282 MHz, DMSO-d₆) −147.70, −120.51 | 628 | 16 (99.9) |
| 41[a,e,c,d] (R)-N-(3-(5-fluoro-2-((2-fluoro-3-(methylsulfonyl)phenyl)amino)pyrimidin-4-yl)-1H-indol-7-yl)-3-methoxy-2-((3S,5S)-3,4,5-trimethylpiperazin-1-yl)propanamide Isomer 2 | 18, 50 | (300 MHz, DMSO-d₆) 0.96 (d, 6H), 2.05-2.47 (m, 5H), 2.62-2.90 (m, 4H), 3.23-3.50 (m, 7H), 3.63 (dd, 1H), 3.77 (dd, 1H), 7.04 (t, 1H), 7.40-7.55 (m, 2H), 7.56-7.70 (m, 1H), 8.12-8.34 (m, 3H), 8.44 (d, 1H), 9.47 (s, 1H), 9.78 (s, 1H), 11.49 (s, 1H) | (282 MHz, DMSO-d₆) −147.70, −120.50 | 628 | 17 (99.7) |
| 42[b,f] (R)-N-(3-(2-((2-fluoro-3-(methylsulfonyl)phenyl)amino)-5-methylpyrimidin-4-yl)-1H-indol-7-yl)-3-methoxy-2-(4-methyl-1,4-diazepan-1-yl)propanamide Isomer 1 | 11, 59 | 1.82-1.95 (m, 2H), 2.39-2.49 (m, 6H), 2.65-2.85 (m, 4H), 2.95-3.01 (m, 1H), 3.02-3.22 (m, 6H), 3.41 (s, 3H), 3.68-3.77 (m, 1H), 3.78-3.89 (m, 1H), 3.90-4.00 (m, 1H), 7.03 (t, 1H), 7.24 (d, 1H), 7.34 (t, 1H), 7.50-7.65 (m, 1H), 7.92 (s, 1H), 8.09 (d, 1H), 8.28 (s, 1H), 8.51-8.60 (m, 1H). | −125.61 | 610 | 5 |

TABLE 22-continued

| Example | Intermediates | ¹H NMR δ (400 MHz, CD₃OD) | ¹⁹F NMR δ (376 MHz, CD₃OD) | m/z (ES+) [M + H]⁺ | Yield % (% ee) |
|---|---|---|---|---|---|
| | | Exchangeable protons not observed | | | |
| 43[b,f] (S)-N-(3-(2-((2-fluoro-3-(methylsulfonyl)phenyl)amino)-5-methylpyrimidin-4-yl)-1H-indol-7-yl)-3-methoxy-2-(4-methyl-1,4-diazepan-1-yl)propanamide Isomer 2 | 11, 59 | 1.82-1.95 (m, 2H), 2.38-2.48 (m, 6H), 2.65-2.85 (m, 4H), 2.90-3.00 (m, 1H), 3.00-3.20 (m, 6H), 3.41 (s, 3H), 3.72 (t, 1H), 3.78-3.89 (m, 1H), 3.90-4.00 (m, 1H), 7.02 (t, 1H), 7.24 (d, 1H), 7.33 (t, 1H), 7.50-7.63 (m, 1H), 7.91 (s, 1H), 8.09 (d, 1H), 8.28 (s, 1H), 8.50-8.63 (m, 1H). Exchangeable protons not observed | −125.67 | 610 | 5 |
| 44[a,e,g] (S)-N-(3-(5-fluoro-2-((2-fluoro-3-(methylsulfonyl)phenyl)amino)pyrimidin-4-yl)-1H-indol-7-yl)-3-methoxy-2-(4-methyl-1,4-diazepan-1-yl)propanamide Isomer 1 | 18, 59 | 1.80-1.97 (m, 2H), 2.44 (s, 3H), 2.65-2.87 (m, 4H), 2.88-3.18 (m, 4H), 3.22 (s, 3H), 3.41 (s, 3H), 3.72 (t, 1H), 3.78-3.89 (m, 1H), 3.90-4.00 (m, 1H), 7.08 (t, 1H), 7.25 (d, 1H), 7.42 (t, 1H), 7.57-7.72 (m, 1H), 8.16 (d, 1H), 8.23-8.37 (m, 2H), 8.38-8.50 (m, 1H). Exchangeable protons not observed | −149.00, −124.62 | 614 | 14 (99.7) |
| 45[a,e,g] (R)-N-(3-(5-fluoro-2-((2-fluoro-3-(methylsulfonyl)phenyl)amino)pyrimidin-4-yl)-1H-indol-7-yl)-3-methoxy-2-(4- | 18, 59 | 1.80-1.97 (m, 2H), 2.43 (s, 3H), 2.65-2.85 (m, 4H), 2.88-3.18 (m, 4H), 3.22 (s, 3H), 3.41 (s, 3H), 3.72 (dd, 1H), 3.84 (dd, 1H), | −148.97, −124.66 | 614 | 14 (99.1) |

TABLE 22-continued

| Example | Intermediates | ¹H NMR δ (400 MHz, CD₃OD) | ¹⁹F NMR δ (376 MHz, CD₃OD) | m/z (ES+) [M + H]⁺ | Yield % (% ee) |
|---|---|---|---|---|---|
| methyl-1,4-diazepan-1-yl)propanamide Isomer 2 | | 3.95 (dd, 1H), 7.08 (t, 1H), 7.25 (dd, 1H), 7.36-7.50 (m, 1H), 7.59-7.71 (m, 1H), 8.16 (d, 1H), 8.23-8.37 (m, 2H), 8.38-8.50 (m, 1H). Exchangeable protons not observed | | | |

ᵃThe reaction mixture was poured into water (50 mL) and extracted with EtOAc (2 × 75 mL). The combined organic layers were dried over Na₂SO₄, filtered and evaporated in vacuo. The residue was purified by preparative TLC using petroleum ether/EtOAc 10:1.
ᵇThe crude was purified by reversed phase preparative chromatography on a Sunfire Prep C18 OBD column (19 × 150 mm, 5 μm) using a gradient of 35-50% acetonitrile in water (0.03% NH₃H₂O) and a flow of 20 mL/min.
ᶜPurified by preparative HPLC on a XBridge Prep C18 OBD column, (5 μm, 19 × 150 mm), using decreasingly polar mixtures of water (containing 0.5% formic acid) in acetonitrile as eluents. Fractions containing the desired compound were evaporated in vacuo.
ᵈThe isomers were separated by preparative chiral-HPLC on a Phenomenex Lux 5u Cellulose-4, AXIA Packed (250 × 21.2 mm, 5 μm) column using 50% hexane (0.1% DEA) in EtOH/MeOH 35:15 as mobile phase and a flow of 20 mL/min. The isomers were detected using a wavelenght of 254 and 220 nm. The desired isomer was collected and evaporated in vacuo.
ᵉThe residue was purified by preparative TLC using DCM/MeOH 10:1, 8:1 or 7:1.
ᶠThe isomers were separated by preparative chiral-HPLC on a Chiralpak IC (20 × 250 mm, 5 μm) using 100% MeOH and a flow of 18 mL/min. The compounds were detected using a wavelenght of 254 and 220 nm. The desired isomer was collected and evaporated in vacuo.
ᵍThe isomers were separated by preparative chiral-HPLC on a ChiralPak IA (21.2 × 150 mm, 5 μm) using 100% MeOH (modified with DEA) as mobile phase. The desired isomer was collected and evaporated in vacuo.

Example 46

(R)-N-(3-(5-fluoro-24(2-fluoro-3-(methylsulfonyl)phenyl)amino)pyrimidin-4-yl)-1H-indol-7-yl)-2-(4-methyl-1,4-diazepan-1-yl)propanamide 2-(4-methyl-1,4-diazepan-1-yl)propanoic acid dihydrochloride, Intermediate 47 (175 mg, 0.68 mmol) and CDI (84 mg, 0.52 mmol) were dissolved in DMF (2 mL) and stirred at room temperature for 1.5 h. 3-(5-fluoro-2-((2-fluoro-3-(methylsulfonyl)phenyl)amino)pyrimidin-4-yl) -1H-indol-7-amine, Intermediate 18 (187 mg, 0.45 mmol) was added and the reaction heated to 60° C. for 4 h. The reaction was allowed to cool to room temperature. DCM (25 mL) was added and the organic phase washed with 8% NaHCO₃ (3×25 mL), dried with a phase separator and evaporated in vacuo. The compound was purified by preparative HPLC on a XBridge C18 column (10 μm, 250×50 mm) using a gradient of 25-70% acetonitrile in H₂O/ACN/NH₃ 95/5/0.2 buffer over 20 minutes with a flow of 100 mL/min. The compounds were detected by UV at 228 nm. The product was collected and lyophilized. The enantiomers were separated using chiral SFC on a CelluCoat (250×20 mm, 5 μm) column using 40% IPA/DEA 100:0.5 in CO₂ at 120 bar as eluent and a flow of 140 ml/min. The compounds were detected by UV at 270 nm. The first eluting compound was collected and evaporated in vacuo. The residue was repurified by preparative HPLC on a XBridge C18 column (10 μm, 250×19 mm) using a gradient of 25-70% acetonitrile in H₂O/ACN/NH₃ 95/5/0.2 buffer over 20 minutes with a flow of 19 mL/min. The compound was detected by UV at 228 nm. The product fractions were collected and lyophilized to yield (R)-N-(3-(5-fluoro-2-((2-fluoro-3-(methylsulfonyl)phenyl)amino)pyrimidin -4-yl)-1H-indol-7-yl)-2-(4-methyl-1,4-diazepan-1-yl)propanamide, Example 46 (40 mg, 30%, 99.9% ee) as a white solid.

¹H NMR (500 MHz, DMSO-d₆) δ 1.25 (d, 3H), 1.71-1.82 (m, 2H), 2.26 (s, 3H), 2.52-2.67 (m, 4H), 2.77-2.89 (m, 4H), 3.23-3.39 (m, 3H), 3.57 (q, 1H), 7.03 (t, 1H), 7.37-7.51 (m, 2H), 7.62 (t, 1H), 8.13-8.24 (m, 2H), 8.27 (d, 1H), 8.44 (d, 1H), 9.45 (s, 1H), 9.77 (s, 1H), 11.61 (bs, 1H). ¹⁹F NMR (470 MHz, DMSO-d₆) δ −120.55, −147.73. m/z (ES+), [M+H]⁺=584.4.

Example 47

(S)-2-((R)-2,4-dimethylpiperazin-1-yl)-N-(3-(2-((2-fluoro-3-(methylsulfonyl)phenyl)amino)-5 -methylpyrimidin-4-yl)-1H-indol-7-yl)propanamide

Step 1

3-(2-((2-fluoro-3-(methylsulfonyl)phenyl)amino)-5-methylpyrimidin-4-yl)-1-((2-(trimethylsilyl)ethoxy)methyl)-1H-indol-7-amine, Intermediate 20 (300 mg, 0.55 mmol) and lithium 2-((R)-2,4-dimethylpiperazin-1-yl)propanoate, Intermediate 69 (103 mg, 0.55 mmol) were suspensioned in DCM (5 mL) and pyridine (0.134 mL, 1.66 mmol) was added. The mixture was cooled to 0° C. and 2,4,6-tripropyl-1,3,5,2,4,6-trioxatriphosphinane 2,4,6-trioxide, T3P (0.989 mL, 1.66 mmol) was added dropwise. The reaction mixture was stirred at 22° C. for 1 h.

Another portion of lithium 2-((R)-2,4-dimethylpiperazin-1-yl)propanoate, Intermediate 53 (20 mg, 0.11 mmol) and T3P (200 μL, 0.34 mmol) were added. The mixture was stirred for 30 min. The reaction mixture was diluted with DCM (15 mL) and quenched with sat. NaHCO₃ (5 mL) and stirred at room temperature for 5 min. The organic layer was separated and the aqueous layer was extracted with DCM (2×5 mL). The combined organic phase was dried with MgSO₄, filtered and concentrated under reduced pressure to afford 2-((R)-2,4-dimethylpiperazin-1-yl)-N-(3-(2-((2-fluoro-3-(methylsulfonyl)phenyl)amino)-5-methylpyrimidin-4-yl)-1-((2-(trimethylsilyl)ethoxy)methyl)-1H-indol-7-yl)propanamide (377 mg, 96%). m/z (ES+), [M+H]⁺=710.5.

Step 2

2-((R)-2,4-dimethylpiperazin-1-yl)-N-(3-(2-((2-fluoro-3-(methylsulfonyl)phenyl)amino)-5-methylpyrimidin-4-yl)-1-((2-(trimethylsilyl)ethoxy)methyl)-1H-indol-7-yl)propanamide (335 mg, 0.47 mmol) was dissolved in DCM (3.5 mL), cooled with an icebath and TFA (1.083 mL, 14.16 mmol) added. The reaction mixture was stirred at room temperature overnight. DCM (5 mL) was added followed by TFA (1 mL) and stirring continued for 5 h. The reaction mixture was then heated at 40° C. overnight. DCM (25 mL) was added followed by NaHCO$_3$ (10 mL) and MeOH (1 mL). The organic layer was separated and the aqueous layer was extracted with DCM (2×20 mL). The combined organic phase was dried with MgSO$_4$, filtered and evaporated in vacuo. The residue was redissolved in DCM (25 mL), sat. NaHCO$_3$ (10 mL) and MeOH (1 mL), shaken and the organic layer separated. The aqueous layer was extracted with DCM (2×20 mL).

The combined organic phase was dried with MgSO$_4$, filtered and evaporated in vacuo. The residue was purified by preparative HPLC on a XBridge C18 column (10 μm, 250×19 mm) using a gradient of 20-80% acetonitrile in H$_2$O/ACN/NH$_3$ 95/5/0.2 buffer over 20 minutes with a flow of 19 mL/min. The compounds were collected by UV at 269 nm and evaporated in vacuo. The diastereoisomers were separated by chiral-SFC on a Chiralpak IB (30×250 mm, 5 μm) column using 35% EtOH/TEA 100:0.5 in CO$_2$ at 120 bar as mobile phase and a flow of 80 mL/min. The compounds were detected by UV at 260 nm. The first eluting isomer was collected and evaporated in vacuo to afford (S)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)propanamide, Example 47 (20 mg, 8%, 99.9% de).

$^1$H NMR (500 MHz, DMSO-d$_6$) δ 1.03 (d, 3H), 1.30 (d, 3H), 1.86 (t, 1H), 2.07-2.23 (m, 4H), 2.40 (s, 3H), 2.54-2.63 (m, 2H), 2.68-2.78 (m, 1H), 2.79-2.91 (m, 2H), 3.25 (s, 3H), 3.69 (q, 1H), 6.97 (t, 1H), 7.32-7.47 (m, 2H), 7.49-7.61 (m, 1H), 8.03 (d, 1H), 8.13 (d, 1H), 8.22-8.35 (m, 2H), 9.17 (s, 1H), 9.65 (s, 1H), 11.38 (s, 1H). m/z (ES+), [M+H]$^+$=580.4.

Example 48

(R)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)propanamide The second eluting isomer from the reaction of Example 47, step 2 was collected and evaporated in vacuo to afford (R)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)propanamide (22 mg, 9% 99.2% de).

$^1$H NMR (500 MHz, DMSO-d$_6$) δ 1.11 (d, 3H), 1.16 (d, 3H), 2.02 (t, 1H), 2.11-2.23 (m, 4H), 2.40 (s, 3H), 2.44-2.49 (m, 1H), 2.54-2.66 (m, 3H), 2.66-2.78 (m, 1H), 3.25 (s, 3H), 3.763.89 (m, 1H), 6.97 (t, 1H), 7.27 (d, 1H), 7.40 (t, 1H), 7.51-7.59 (m, 1H), 8.00 (s, 1H), 8.14 (d, 1H), 8.23-8.36 (m, 2H), 9.16 (s, 1H), 9.58 (s, 1H), 11.37 (s, 1H). m/z (ES+), [M+H]$^+$=580.4.

Example 49

(R)-2-((R)-2,4-dimethylpiperazin-1-yl)-N-(3-(5-fluoro-2-((2-fluoro-3-(methylsulfonyl)phenyl)amino)pyrimidin-4-yl)-1H-indol-7-yl)propanamide (R)-2-((R)-2,4-dimethylpiperazin-1-yl)propanoic acid dihydrochloride, Intermediate 27 (573 mg, 2.21 mmol) and CDI (275 mg, 1.70 mmol) were stirred in DMF (2 mL) at room temperature for 1 h (gas evolution). 3-(5-fluoro-2-((2-fluoro-3-(methylsulfonyl)phenyl)amino)pyrimidin-4-yl)-1H-indol-7-amine, Intermediate 18 (816 mg, 1.47 mmol) dissolved in DMF (2 mL) was added and the reaction stirred at 50° C. for 5 h. The reaction was diluted with DCM (25 mL) and 5% Na$_2$CO$_3$ (aq) (25 mL), shaken and the phases separated. The aqueous phase was extracted with DCM (2×25 mL). The combined organic phases dried with a phase separator and concentrated in vacuo. The residue purified twice by preparative HPLC on a XBridge C18 column (10 μm, 250×50 mm) using a gradient of 15-65% acetonitrile in H$_2$O/ACN/NH$_3$ 95/5/0.2 buffer over 20 minutes with a flow of 100 mL/min. The compounds were detected by UV at 235 nm. The product was lyophilized to afford (R)-2-((R)-2,4-dimethylpiperazin-1-yl)-N -(3-(5-fluoro-2-((2-fluoro-3-(methylsulfonyl)phenyl)amino)pyrimidin-4-yl)-1H-indol-7-yl)propanamide, Example 49 (234 mg, 32%) as a white solid.

$^1$H NMR (500 MHz, DMSO-d$_6$) δ 1.11 (d, 3H), 1.16 (d, 3H), 2.02 (t, 1H), 2.1-2.23 (m, 4H), 2.42-2.54 (m, 1H), 2.54-2.67 (m, 3H), 2.67-2.78 (m, 1H), 3.25-3.36 (m, 3H), 3.77-3.88 (m, 1H), 7.03 (t, 1H), 7.28 (d, 1H), 7.46 (t, 1H), 7.57-7.68 (m, 1H), 8.15-8.24 (m, 2H), 8.29 (d, 1H), 8.43 (d, 1H), 9.45 (s, 1H), 9.63 (s, 1H), 11.55 (s, 1H). m/z (ES+), [M+H]$^+$=584.3.

Example 50

(S)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide 3-(2-((2-fluoro-3-(methylsulfonyl)phenyl)amino)-5-methylpyrimidin-4-yl)-1H-indol-7-amine, Intermediate 11 (387 mg, 0.94 mmol) and 2-((R)-2,4-dimethylpiperazin-1-yl)butanoic acid dihydrochloride, Intermediate 46 (300 mg, 1.10 mmol) were suspensioned in anhydrous DCM (25 mL) and pyridine (0.3 mL, 3.71 mmol) added. The mixture was cooled to 0° C. in an icebath and T3P (1.5 mL, 2.52 mmol) added drop wise. The icebath was removed and the reaction mixture was stirred at 23° C. for 20 min. The reaction mixture was quenched with sat. NaHCO$_3$ (20 mL) and stirred at 23° C. for 30 min. The organic layer was separated and the aqueous phase was extracted with DCM (2×20 mL). The combined organic phase was filtered through a phase separator and evaporated in vacuo. The residue was purified by preparative HPLC in two injections on a XBridge C18 column (10 μm, 250×50 mm) using a gradient of 20-70% acetonitrile in H$_2$O/ACN/NH$_3$ 95/5/0.2 buffer over 25 minutes with a flow of 100 mL/min. The compounds were detected by UV at 269 nm. The first eluting isomer was collected and lyophilized to afford (S)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide, Example 50 (205 mg, 37%).

$^1$H NMR (500 MHz, DMSO-d$_6$) δ 0.97 (t, 3H), 1.10 (d, 3H), 1.65-1.77 (m, 2H), 1.77-1.87 (m, 1H), 1.91-2.01 (m, 1H), 2.11 (s, 3H), 2.40 (s, 3H), 2.55-2.67 (m, 2H), 2.67-2.77 (m, 2H), 2.81-2.94 (m, 2H), 3.25 (s, 3H), 3.55 (t, 1H), 6.97 (t, 1H), 7.40 (t, 1H), 7.47 (d, 1H), 7.5-7.58 (m, 1H), 8.05 (d, 1H), 8.12 (d, 1H), 8.24-8.34 (m, 2H), 9.17 (s, 1H), 9.62 (s, 1H), 11.20 (s, 1H). m/z (ES+), [M+H]$^+$=594.4.

Example 51

(R)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide The second eluting isomer from the reaction of Example 50 was collected and lyophilized to afford (R)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide, Example 51 (210 mg, 38%).

$^1$H NMR (500 MHz, DMSO-$d_6$) δ 0.95 (t, 3H), 1.13 (d, 3H), 1.57-1.69 (m, 1H), 1.72-1.86 (m, 1H), 2.00-2.09 (m, 1H), 2.09-2.23 (m, 4H), 2.38-2.58 (m, 6H), 2.72-2.81 (m, 1H), 2.81-2.91 (m, 1H), 3.25 (s, 3H), 3.44-3.53 (m, 1H), 6.98 (t, 1H), 7.35-7.45 (m, 2H), 7.51-7.6 (m, 1H), 8.03 (d, 1H), 8.13 (d, 1H), 8.24-8.36 (m, 2H), 9.16 (s, 1H), 9.61 (s, 1H), 11.32 (s, 1H). m/z (ES+), [M+H]$^+$=594.4.

The procedure described above for Examples 50-51 were repeated using the indicated intermediates to give Example 52-57 described in Table 23 below

TABLE 23

| Example | Intermediates | $^1$H NMR δ (500 MHz, DMSO-$d_6$) | $^{19}$F NMR δ (471 MHz, DMSO-$d_6$) | m/z (ES+) [M + H]$^+$ | Yield % |
|---|---|---|---|---|---|
| 52$^a$ (S)-2-((R)-2,4-dimethylpiperazin-1-yl)-N-(3-(5-fluoro-2-((2-fluoro-3-(methylsulfonyl)phenyl)amino)pyrimidin-4-yl)-1H-indol-7-yl)butanamide Isomer 1 | 18, 46 | 0.96 (t, 3H), 1.10 (d, 3H), 1.65-1.77 (m, 2H), 1.78-1.87 (m, 1H), 1.9-2.01 (m, 1H), 2.11 (s, 3H), 2.55-2.66 (m, 2H), 2.66-2.77 (m, 1H), 2.82-2.95 (m, 2H), 3.30 (s, 3H), 3.55 (t, 1H), 7.03 (t, 1H), 7.42-7.53 (m, 2H), 7.58-7.67 (m, 1H), 8.14-8.22 (m, 1H), 8.22-8.31 (m, 2H), 8.43 (d, 1H), 9.45 (s, 1H), 9.67 (s, 1H), 11.40 (s, 1H). | | 598.4 | 19 |
| 53$^a$ (R)-2-((R)-2,4-dimethylpiperazin-1-yl)-N-(3-(5-fluoro-2-((2-fluoro-3-(methylsulfonyl)phenyl)amino)pyrimidin-4-yl)-1H-indol-7-yl)butanamide Isomer 2 | 18, 46 | 0.95 (t, 3H), 1.13 (d, 3H), 1.57-1.69 (m, 1H), 1.72-1.85 (m, 1H), 2.00-2.09 (m, 1H), 2.09-2.24 (m, 4H), 2.39-2.58 (m, 3H), 2.72-2.81 (m, 1H), 2.81-2.91 (m, 1H), 3.30 (s, 3H), 3.45-3.54 (m, 1H), 7.03 (t, 1H), 7.41 (d, 1H), 7.46 (t, 1H), 7.57-7.68 (m, 1H), 8.13-8.25 (m, 2H), 8.27 (d, 1H), 8.43 (d, 1H), 9.45 (s, 1H), 9.67 (s, 1H), 11.50 (s, 1H). | | 598.3 | 34 |
| 54$^b$ (S)-2-((R)-2,4-dimethylpiperazin-1-yl)-N-(3-(2-((2-fluoro-3-(methylsulfonyl)phenyl)amino)-5-methylpyrimidin-4-yl)-1H-indol-7-yl)-3-methoxypropanamide Isomer 1 | 11, 54 | 1.10 (d, 3H), 1.77-1.86 (m, 1H), 1.99-2.09 (m, 1H), 2.11 (s, 3H), 2.40 (s, 3H), 2.43-2.6 (m, 2H), 2.71-2.88 (m, 2H), 2.97 (t, 1H), 3.21-3.44 (m, 6H), 3.61-3.7 (m, 1H), 3.79-3.89 (m, 2H), 6.98 (t, 1H), 7.40 (t, 1H), 7.48 (d, 1H), 7.55 (t, 1H), 8.06 (d, 1H), 8.13 (d, 1H), 8.25-8.35 (m, 2H), 9.17 (s, 1H), 9.71 (s, 1H), 11.23 (s, 1H). | | 610.4 | 5 |
| 55$^b$ (R)-2-((R)-2,4-dimethylpiperazin-1-yl)-N-(3-(2-((2-fluoro-3-(methylsulfonyl)phenyl)amino)-5-methylpyrimidin- | 11, 54 | 1.14 (d, 3H), 1.95 (t, 1H), 2.09-2.22 (m, 4H), 2.40 (s, 3H), 2.55-2.66 (m, 3H), 2.8-2.88 (m, 1H), 2.92-3.03 (m, 1H), 3.25 (s, 3H), 3.30 (s, 3H), 3.77 | | 610.4 | 22 |

TABLE 23-continued

| Example | Intermediates | ¹H NMR δ (500 MHz, DMSO-d₆) | ¹⁹F NMR δ (471 MHz, DMSO-d₆) | m/z (ES+) [M + H]⁺ | Yield % |
|---|---|---|---|---|---|
| 4-yl)-1H-indol-7-yl)-3-methoxypropanamide Isomer 2 | | (dd, 1H), 3.84 (dd, 1H), 3.95 (t, 1H), 6.98 (t, 1H), 7.27 (d, 1H), 7.40 (t, 1H), 7.50-7.60 (m, 1H), 8.01 (d, 1H), 8.15 (d, 1H), 8.25-8.35 (m, 2H), 9.16 (s, 1H), 9.71 (s, 1H), 11.27 (s, 1H). | | | |
| 56[a] (S)-2-((R)-2,4-dimethylpiperazin-1-yl)-N-(3-(5-fluoro-2-((2-fluoro-3-(methylsulfonyl)phenyl)amino)pyrimidin-4-yl)-1H-indol-7-yl)-3-methoxypropanamide Isomer 1 | 18, 54 | 1.10 (d, 3H), 1.81 (t, 1H), 2.04 (t, 1H), 2.11 (s, 3H), 2.48-2.6 (m, 2H), 2.72-2.86 (m, 2H), 2.93-3.02 (m, 1H), 3.28-3.32 (m, 6H), 3.61-3.69 (m, 1H), 3.8-3.88 (m, 2H), 7.03 (t, 1H), 7.40-7.55 (m, 2H), 7.58-7.67 (m, 1H), 8.14-8.23 (m, 1H), 8.23-8.32 (m, 2H), 8.44 (d, 1H), 9.45 (s, 1H), 9.76 (s, 1H), 11.44 (s, 1H). | | 614.3 | 38 |
| 57[a] (R)-2-((R)-2,4-dimethylpiperazin-1-yl)-N-(3-(5-fluoro-2-((2-fluoro-3-(methylsulfonyl)phenyl)amino)pyrimidin-4-yl)-1H-indol-7-yl)-3-methoxypropanamide Isomer 2 | 18, 54 | 1.14 (d, 3H), 1.95 (t, 1H), 2.09-2.21 (m, 4H), 2.53-2.66 (m, 3H), 2.79-2.88 (m, 1H), 2.92-3.02 (m, 1H), 3.24-3.43 (m, 6H), 3.77 (dd, 1H), 3.84 (dd, 1H), 3.95 (t, 1H), 7.04 (t, 1H), 7.29 (d, 1H), 7.46 (t, 1H), 7.59-7.67 (m, 1H), 8.14-8.24 (m, 2H), 8.29 (d, 1H), 8.43 (d, 1H), 9.45 (s, 1H), 9.76 (s, 1H), 11.47 (s, 1H). | −120.54, −147.72 | 614.3 | 24 |

[a]More T3P was added in portions.
[b]After 1 h at 0° C., DIPEA (0.9 mL, 5.15 mmol) and additional T3P (3.0 mL, 5.04 mmol) were added to the reaction mixture in small portions at room temperature over 3 h.

Example 58

(R)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)propanamide

Step 1

3-(2-((2-fluoro-3-(methylsulfonyl)phenyl)amino)-5-methylpyrimidin-4-yl)-1-((2-(trimethylsilyl)ethoxy)methyl)-1H-indol-7-amine, Intermediate 20 (210 mg, 0.39 mmol) and lithium 2-((S)-2,4-dimethylpiperazin-1-yl)propanoate, Intermediate 51 (97 mg, 0.44 mmol, ~84% wt) were suspensioned in DCM (10 mL) and pyridine (0.10 mL, 1.24 mmol) added. The mixture was cooled to 0° C. and T3P (0.9 mL, 1.51 mmol, 50% wt in EtOAc) was added drop wise. The reaction mixture was stirred at 22° C. for 1 hour. Lithium 2-((S)-2,4-dimethylpiperazin-1-yl)propanoate, Intermediate 51 (24 mg, 0.11 mmol) was added followed by T3P (0.2 mL, 0.34 mmol) and the reaction mixture was stirred at 22° C. for 30 min. The reaction mixture was quenched with sat. NaHCO₃ (20 mL) and stirred at 22° C. for 15 min. The organic layer was separated and the aqueous layer was extracted with DCM (2×10 mL). The combined organic phase was filtered through a phase separator and concentrated in vacuo. The diastereoisomers were separated by chiral SFC on a CelluCoat (5 µm, 250×30 mm) column using 32% EtOH/DEA 100:0.5 in CO₂ at 120 bar and a flow of 140 mL/min. The compounds were detected by UV at 220 nm. The first eluting isomer was collected and evaporated in vacuo to afford 2-((S)-2,4-dimethylpiperazin-1-yl)-N-(3-(2-((2-fluoro-3-(methylsulfonyl)phenyl)amino) -5-methylpyrimidin-4-yl)-1-((2-(trimethylsilyl)ethoxy)methyl)-1H-indol-7-yl)propanamide Isomer 1 (125 mg, 45%, 99.9% de).

¹H NMR (500 MHz, DMSO-d₆) δ −0.09 (s, 9H), 0.77-0.89 (m, 1H), 0.92-1.17 (m, 4H), 1.25 (d, 3H), 1.81-1.95 (m, 1H), 2.13 (s, 3H), 2.22-2.34 (m, 1H), 2.39 (s, 3H), 2.43-2.62 (m, 3H), 2.67-2.86 (m, 2H), 3.07-3.65 (m, 6H), 5.72 (d, 1H), 5.87 (d, 1H), 7.05 (t, 1H), 7.35-7.48 (m, 2H), 7.51-7.6 (m, 1H), 8.15 (d, 1H), 8.19 (s, 1H), 8.23-8.31 (m, 1H), 8.31-8.41 (m, 1H), 9.23 (s, 1H), 9.86 (s, 1H).

Step 2

2-((S)-2,4-dimethylpiperazin-1-yl)-N-(3-(2-((2-fluoro-3-(methylsulfonyl)phenyl)amino)-5-methylpyrimidin-4-yl)-1-

((2-(trimethylsilyl)ethoxy)methyl)-1H-indol-7-yl)propanamide Isomer 1 (123 mg, 0.17 mmol) was dissolved in anhydrous DCM (2 mL) and TFA (3 mL) added. The reaction mixture was stirred at ambient temperature for 19 h. DCM (10 mL) was added followed by NaHCO$_3$ (10 mL) and MeOH (1 mL). The organic layer was separated and the aqueous layer was extracted with a mixture of DCM/MeOH 5:1 (2×6 mL). The combined organic phase was filtered through a phase separator and concentrated in vacuo. The residue was purified by preparative HPLC on a XBridge C18 column (10 μm, 250×19 mm) using a gradient of 20-80% acetonitrile in H$_2$O/ACN/NH$_3$ 95/5/0.2 buffer over 20 minutes with a flow of 19 mL/min. The compounds were detected by UV at 269 nm. The product was collected and lyophilized to afford (R)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)propanamide, Example 58 (63 mg, 63%) as a white solid.

$^1$H NMR (500 MHz, DMSO-d$_6$) δ 1.03 (d, 3H), 1.30 (d, 3H), 1.86 (t, 1H), 2.08-2.22 (m, 4H), 2.40 (s, 3H), 2.46-2.62 (m, 2H), 2.68-2.78 (m, 1H), 2.79-2.91 (m, 2H), 3.25 (s, 3H), 3.69 (q, 1H), 6.97 (t, 1H), 7.33-7.45 (m, 2H), 7.5-7.59 (m, 1H), 8.03 (s, 1H), 8.12 (d, 1H), 8.25-8.36 (m, 2H), 9.16 (s, 1H), 9.64 (s, 1H), 11.36 (s, 1H). m/z (ES+), [M+H]$^+$=580.3.

Example 59

(S)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)propanamide Isomer 2

Step 1

The second eluting isomer from the reaction of Example 58, step 1, was collected and evaporated in vacuo to afford 2-((S)-2,4-dimethylpiperazin-1-yl)-N-(3-(2-((2-fluoro-3-(methylsulfonyl)phenyl)amino)-5-methylpyrimidin-4-yl)-1-((2-(trimethylsilyl)ethoxy)methyl) -1H-indol-7-yl)propanamide Isomer 2 (120 mg, 43%, 99.7% de).

$^1$H NMR (500 MHz, DMSO-d$_6$) δ −0.09 (s, 9H), 0.81-0.91 (m, 1H), 0.95-1.16 (m, 7H), 1.95 (t, 1H), 2.03-2.18 (m, 4H), 2.33-2.43 (m, 4H), 2.43-2.57 (m, 1H), 2.58-2.72 (m, 3H), 3.25 (s, 3H), 3.4-3.56 (m, 2H), 3.84 (s, 1H), 5.73 (d, 1H), 5.87 (d, 1H), 7.04 (t, 1H), 7.40 (t, 1H), 7.48 (d, 1H), 7.55 (t, 1H), 8.11-8.22 (m, 2H), 8.27 (t, 1H), 8.33 (s, 1H), 9.23 (s, 1H), 9.84 (s, 1H).

Step 2

2-((S)-2,4-dimethylpiperazin-1-yl)-N-(3-(2-((2-fluoro-3-(methylsulfonyl)phenyl)amino)-5-methylpyrimidin-4-yl)-1-((2-(trimethylsilyl)ethoxy)methyl)-1H-indol-7-yl)propanamide Isomer 2 (118 mg, 0.17 mmol) was dissolved in anhydrous DCM (2 mL) and TFA (3 mL) was added. The reaction mixture was stirred at ambient temperature for 19 hours. DCM (10 mL) was added followed by NaHCO$_3$ (10 mL) and MeOH (1 mL). The organic layer was separated and the aqueous layer was extracted with a mixture of DCM/MeOH 5:1 (2×6 mL). The combined organic phase was filtered through a phase separator and concentrated in vacuo. The residue was purified by preparative HPLC on a XBridge C18 column (10 μm, 250×19 mm) using a gradient of 20-80% acetonitrile in H$_2$O/ACN/NH$_3$ 95/5/0.2 buffer over 20 minutes with a flow of 19 mL/min. The compounds were detected by UV at 269 nm. The product fractions were lyophilized to afford (S)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)propanamide, Example 59 (74 mg, 77%) as a white solid.

$^1$H NMR (500 MHz, DMSO-d$_6$) δ 1.12 (d, 3H), 1.16 (d, 3H), 2.02 (t, 1H), 2.15 (s, 3H), 2.16-2.22 (m, 1H), 2.40 (s, 3H), 2.43-2.48 (m, 1H), 2.54-2.66 (m, 3H), 2.67-2.77 (m, 1H), 3.25 (s, 3H), 3.76-3.88 (m, 1H), 6.97 (t, 1H), 7.27 (d, 1H), 7.40 (t, 1H), 7.51-7.59 (m, 1H), 8.00 (s, 1H), 8.14 (d, 1H), 8.26-8.34 (m, 2H), 9.16 (s, 1H), 9.58 (s, 1H), 11.36 (s, 1H). m/z (ES+), [M+H]$^+$=580.5.

Example 60

(R)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide Step 1

Lithium 2-((S)-2,4-dimethylpiperazin-1-yl)butanoate, Intermediate 52 (104 mg, 0.52 mmol) and 3-(2-((2-fluoro-3-(methylsulfonyl)phenyl)amino)-5-methylpyrimidin-4-yl)-1-((2-(trimethylsilyl)ethoxy)methyl)-1H-indol-7-amine, Intermediate 20 (210 mg, 0.39 mmol) were dissolved in DCM (10 mL) and pyridine (0.1 mL, 1.24 mmol) added followed by T3P (1.0 mL, 1.68 mmol). The reaction mixture was stirred at 22° C. overnight. The reaction mixture was quenched with NaHCO$_3$ (15 mL) stirred for another 10 min and extracted with DCM (3×7 mL). The combined organic phase was filtered through a phase separator and concentrated in vacuo. The residue was purified by preparative HPLC on a XBridge C18 column (10 μm, 250×50 mm) using a gradient of 20-80% acetonitrile in H$_2$O/ACN/NH$_3$ 95/5/0.2 buffer over 20 minutes with a flow of 100 mL/min. The compounds were detected by UV at 269 nm. Pure fractions were pooled and lyophilized. The diastereoisomers were separated by chiral SFC on a ChiralPak IB column (5 μm, 250×30 mm) using 23% EtOH/DEA 100:0.5 in CO$_2$ at 120 bar and a flow of 150 mL/min. The compounds were detected using UV at 270 nm. The first eluting isomer was collected and evaporated in vacuo to afford 2-((S)-2,4-dimethylpiperazin-1-yl)-N-(3-(2-((2-fluoro-3-(methylsulfonyl)phenyl)amino)-5-methylpyrimidin-4-yl)-1-((2-(trimethylsilyl)ethoxy)methyl)-1H-indol-7-yl)butanamide Isomer 1 (69 mg, 24%, 99.3% de).

$^1$H NMR (500 MHz, DMSO-d$_6$) δ −0.08 (s, 9H), 0.80-0.96 (m, 2H), 0.99 (t, 3H), 1.06 (d, 3H), 1.63-1.87 (m, 3H), 2.06-2.16 (m, 4H), 2.39 (s, 3H), 2.56 (d, 2H), 2.73-2.86 (m, 3H), 3.25 (s, 3H), 3.31 (s, 1H), 3.47-3.56 (m, 2H), 5.78 (dd, 2H), 7.05 (t, 1H), 7.37-7.44 (m, 2H), 7.52-7.59 (m, 1H), 8.13-8.21 (m, 2H), 8.28 (t, 1H), 8.33 (s, 1H), 9.23 (s, 1H), 9.61 (s, 1H).

Step 2

2-((S)-2,4-dimethylpiperazin-1-yl)-N-(3-(2-((2-fluoro-3-(methylsulfonyl)phenyl)amino)-5-methylpyrimidin-4-yl)-1-((2-(trimethylsilyl)ethoxy)methyl)-1H-indol-7-yl)butanamide Isomer 1 (67 mg, 0.09 mmol) was dissolved in DCM (2 mL) and TFA (3 mL) was added. The reaction mixture was stirred at 22° C. for 17 h. DCM (10 mL) and NaHCO$_3$ (15 mL) were added, shaken, the phases separated and the aqueous layer extracted with DCM (2×5 mL). The combined organic phases was filtered through a phase separator and concentrated in vacuo. The residue was purified by preparative HPLC on a XBridge C18 column (10 μm, 250×19 mm) using a gradient of 20-80% acetonitrile in H$_2$O/ACN/NH$_3$ 95/5/0.2 buffer over 20 minutes with a flow of 19 mL/min. The compounds were detected by UV at 269 nm. The product peaks were collected and lyophilized to afford (R)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide, Example 60 (31 mg, 56%) as a white solid.

$^1$H NMR (500 MHz, DMSO-d$_6$) δ 0.97 (t, 3H), 1.10 (d, 3H), 1.62-1.88 (m, 3H), 1.97 (t, 1H), 2.11 (s, 3H), 2.39 (s, 3H), 2.55-2.67 (m, 2H), 2.67-2.77 (m, 1H), 2.82-2.95 (m, 2H), 3.25 (s, 3H), 3.56 (t, 1H), 6.97 (t, 1H), 7.40 (t, 1H), 7.48 (d, 1H), 7.55 (t, 1H), 8.05 (d, 1H), 8.12 (d, 1H), 8.24-8.37 (m, 2H), 9.16 (s, 1H), 9.63 (s, 1H), 11.22 (s, 1H). m/z (ES+), [M+H]$^+$=594.4.

Example 61

(S)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide Step 1

The second eluting isomer from Example 60, step 1, was collected and evaporated in vacuo to afford 2-((S)-2,4-dimethylpiperazin-1-yl)-N-(3-(2-((2-fluoro-3-(methylsulfonyl)phenyl)amino)-5-methylpyrimidin-4-yl)-1-((2-(trimethylsilyl)ethoxy)methyl)-1H-indol-7-yl)butanamide (133 mg, 47%, 95.9% de).

$^1$H NMR (500 MHz, DMSO-d$_6$) δ −0.09 (s, 9H), 0.82-0.91 (m, 1H), 0.92-1.02 (m, 4H), 1.12 (d, 3H), 1.53-1.66 (m, 1H), 1.69-1.84 (m, 1H), 1.91-2.02 (m, 1H), 2.02-2.1 (m, 1H), 2.12 (s, 3H), 2.39 (s, 3H), 2.43-2.66 (m, 4H), 2.74-2.84 (m, 1H), 3.25 (s, 3H), 3.48-3.56 (m, 3H), 5.77 (d, 1H), 5.84 (d, 1H), 7.05 (t, 1H), 7.40 (t, 1H), 7.49 (d, 1H), 7.52-7.59 (m, 1H), 8.15 (d, 1H), 8.18 (s, 1H), 8.24-8.31 (m, 1H), 8.33 (s, 1H), 9.23 (s, 1H), 9.73 (s, 1H).

Step 2

2-((S)-2,4-dimethylpiperazin-1-yl)-N-(3-(2-((2-fluoro-3-(methylsulfonyl)phenyl)amino)-5-methylpyrimidin-4-yl)-1-((2-(trimethylsilyl)ethoxy)methyl)-1H-indol-7-yl)butanamide Isomer 2 (131 mg, 0.18 mmol) was dissolved in DCM (2 mL) and TFA (3 mL) added. The reaction mixture was stirred at 22° C. for 17 h. DCM (10 mL) and NaHCO$_3$ (15 mL) were added, shaken, the phases separated and the aqueous layer extracted with DCM (2×5 mL). The combined organic phases were filtered through a phase separator and concentrated in vacuo. The residue was purified by preparative HPLC on a XBridge C18 column (10 µm, 250×19 mm) using a gradient of 20-80% acetonitrile in H$_2$O/ACN/NH$_3$ 95/5/0.2 buffer over 20 minutes with a flow of 19 mL/min. The compounds were detected by UV at 269 nm. The product was collected and lyophilized to afford (S)-2-((S)-2,4-dimethylpiperazin-1-yl)-N-(3-(2-((2-fluoro-3-(methylsulfonyl)phenyl)amino)-5-methylpyrimidin-4-yl)-1H-indol-7-yl)butanamide Isomer 2, Example 61 (65 mg, 60%) as a white solid.

$^1$H NMR (500 MHz, DMSO-d$_6$) δ 0.95 (t, 3H), 1.13 (d, 3H), 1.56-1.70 (m, 1H), 1.72-1.85 (m, 1H), 2.01-2.09 (m, 1H), 2.09-2.23 (m, 4H), 2.34-2.58 (m, 6H), 2.73-2.81 (m, 1H), 2.81-2.91 (m, 1H), 3.25 (s, 3H), 3.45-3.54 (m, 1H), 6.98 (t, 1H), 7.36-7.46 (m, 2H), 7.50-7.59 (m, 1H), 8.03 (d, 1H), 8.13 (d, 1H), 8.25-8.37 (m, 2H), 9.16 (s, 1H), 9.62 (s, 1H), 11.33 (s, 1H). m/z (ES+), [M+H]$^+$=594.5.

Example 62

(R)-3-ethoxy-N-(3-(2-((2-fluoro-3-(methylsulfonyl)phenyl)amino)-5-methylpyrimidin-4-yl)-1H-indol-7-yl)-2-(4-methylpiperazin-1-yl)propanamide DIPEA (688 µl, 3.94 mmol) was added in one portion to lithium (R)-3-ethoxy-2-(4-methylpiperazin-1-yl)propanoate, Intermediate 63 (237 mg, 1.09 mmol) and 3-(2-((2-fluoro-3-(methylsulfonyl)phenyl)amino)-5-methylpyrimidin-4-yl)-1H-indol-7-amine, Intermediate 11 (180 mg, 0.44 mmol) in DCM (1 mL) at 0° C. The resulting solution was stirred at 0° C. for 10 min. Then 1-Propanephosphonic acid cyclic anhydride, T3P (835 mg, 1.31 mmol) was added dropwise at 0° C. The solution was stirred at room temperature for 1 hour. The reaction mixture was diluted with DCM (50 mL), washed with saturated NaHCO$_3$ (2×50 mL) and brine (2×50 mL). The organic layer was dried over Na$_2$SO$_4$, filtered and evaporated in vacuo. The residue was purified by preparative TLC using DCM/MeOH 20:1 as eluent. The product (50% ee) was purified by preparative chiral-HPLC on a Chiralpak IA (20×250 mm, 5 µm) using 20% IPA in MTBE (0.1% DEA) as eluent with a flow of 20 mL/min over 19 min. The product was detected using the wavelength of 254 and 220 nm. The major isomer was collected to afford (R)-3-ethoxy-N-(3-(2-((2-fluoro-3-(methylsulfonyl)phenyl)amino)-5-methylpyrimidin-4-yl)-1H-indol-7-yl)-2-(4-methylpiperazin-1-yl)propanamide, Example 62 (40 mg, 15%, 99.7% ee) as a white solid.

$^1$H NMR (300 MHz, CD$_3$OD) δ 1.21 (t, 3H), 2.33 (s, 3H), 2.42 (s, 6H), 2.50-2.73 (m, 4H), 2.74-3.02 (m, 2H), 3.15 (s, 3H), 3.45-3.65 (m, 3H), 3.86 (dd, 1H), 3.97 (dd, 1H), 7.02 (t, 1H), 7.13 (d, 2H), 7.31 (t, 1H), 7.49-7.63 (m, 1H), 7.90 (s, 1H), 8.10 (d, 1H), 8.25 (s, 1H), 8.47-8.52 (m, 1H). $^{19}$F NMR (282 MHz, CD$_3$OD) δ −125.71. m/z (ES+), [M+H]$^+$=610.

Example 63

(R)-3-ethoxy-N-(3-(5-fluoro-2-((2-fluoro-3-(methylsulfonyl)phenyl)amino)pyrimidin-4-yl)-1H-indol-7-yl)-2-(4-methylpiperazin-1-yl)propanamide The procedure described above for Example 62 was repeated using intermediates 18 and 63 to give Example 63 (80 mg, 24%, 97.9% ee) as a white solid. Purified by preparative chiral-HPLC on a ChiralPak-AD-H-SL002, (20×250 mm) using 50% IPA in hexane (0.1% DEA) and a flow of 14 mL/min over 56 min. The compound was detected using 254 and 220 nm. The major isomer were evaporated in vacuo.

$^1$H NMR (300 MHz, CD$_3$OD) δ 1.21 (t, 3H), 2.32 (s, 3H), 2.45-2.72 (m, 4H), 2.73-3.02 (m, 4H), 3.21 (s, 3H), 3.44-3.66 (m, 3H), 3.78-4.04 (m, 2H), 7.00-7.21 (m, 2H), 7.42 (t, 1H), 7.58-7.73 (t, 1H), 8.16 (s, 1H), 8.23-8.37 (m, 2H), 8.42 (t, 1H).

Exchangeable protons not observed $^{19}$F NMR (282 MHz, CD$_3$OD) δ −149.01, −124.61 m/z (ES+), [M+H]$^+$=614.

Example 64

(R)-3-(benzyloxy)-N-(3-(2-((2-fluoro-3-(methylsulfonyl)phenyl)amino)-5-methylpyrimidin-4-yl)-1H-indol-7-yl)-2-(4-methylpiperazin-1-yl)propanamide Step 1

Sodium 3-(benzyloxy)-2-(4-methylpiperazin-1-yl)propanoate, Intermediate 64 (317 mg, 0.93 mmol) and 3-(2-((2-fluoro-3-(methylsulfonyl)phenyl)amino)-5-methylpyrimidin-4-yl)-1-((2-(trimethylsilyl)ethoxy)methyl)-1H-indol-7-amine, Intermediate 20 (448 mg, 0.83 mmol) were suspended in ethyl acetate (20 mL) and pyridine (0.25 mL, 3.09 mmol) was added. The reaction mixture was cooled to 0° C. and T3P (1.0 mL, 1.68 mmol, 50% wt in ethyl acetate) was added drop wise. The reaction mixture was stirred at 0° C. for 10 min and then at 22° C. for 14 h. The reaction mixture was cooled to 0° C., T3P (1.0 mL, 1.68 mmol) added drop wise and stirring continued at 22° C. for 3 h. The reaction mixture was cooled again to 0° C., T3P (0.5 mL, 0.84 mmol) added drop wise and stirring at 22° C. for 2 h. The reaction mixture was cooled again to 0° C., T3P (0.5 mL, 0.84 mmol) added drop wise and stirring continued at 22° C. for 16 h. Water (5 mL) was added and the mixture was stirred at 22° C. for 30 min. NaHSO$_4$ (20 mL) was added followed by DCM (10 mL) and the phases separated. The aqueous phase was extracted with DCM (2×10 mL). The combined organic phase was dried over Na$_2$SO$_4$, filtered and concentrated in vacuo to afford 3-(benzyloxy)-N-(3-(2-((2-fluoro-3-(methylsulfonyl)phenyl)amino)-5-methylpyrimidin-4-yl)-1-((2-(trimethylsilyl)ethoxy)methyl)-1H-indol-7-yl)-2-(4-methylpiperazin-1-yl)propanamide (690 mg, quant) which was taken directly to the next step. m/z (ES+), [M+H]$^+$=802.3.

Step 2

3-(benzyloxy)-N-(3-(2-((2-fluoro-3-(methylsulfonyl)phenyl)amino)-5-methylpyrimidin-4-yl)-1-((2-(trimethylsilyl)ethoxy)methyl)-1H-indol-7-yl)-2-(4-methylpiperazin-1-yl) propanamide Isomer 2 (600 mg, 0.75 mmol) was dissolved in anhydrous DCM (3 mL) and TFA (3 mL, 26 mmol) added to the stirred solution at ambient temperature. The reaction mixture was stirred at 22° C. for 4 h. TFA (2 mL) was added and the reaction mixture was stirred at 22° C. for 3 days. TFA (2 mL) was added and stirring continued for 4 days. TFA (2 mL) was added and the mixture was stirred at 22° C. overnight. DCM (20 mL) was added and the mixture was neutralized with sat. NaHCO$_3$ (50 mL) and MeOH (3 mL) was added. The organic layer was separated and the aqueous phase was extracted with 10% MeOH in DCM (2×11 mL). The combined organic phase was filtered through a phase separator followed by a small plug of silica, which was washed with a mixture of DCM and MeOH. The combined filtrate was concentrated in vacuo. The residue was purified by preparative HPLC on a XBridge C18 column (10 μm 250×50 mm) using a gradient of 20-80% acetonitrile in H$_2$O/ACN/NH$_3$ 95/5/0.2 buffer over 30 minutes with a flow of 100 mL/min. The compounds were detected by UV at 269 nm. The product peaks were collected and lyophilized. The enantiomers were separated by preprative chiral HPLC on a Lux C4 column (30×250 mm, 5 μm) using 100% MeOH/NH$_3$ 100:0.1 as eluent and a flow of 40 mL/min. The compounds were detected by UV at 260 nm. The second eluting isomer was collected and evaporated in vacuo. The residue was repurifed by preparative HPLC on a XBridge C18 column (10 μm, 250×50 ID mm) using a gradient of 25-75% acetonitrile in H$_2$O/ACN/NH$_3$ 95/5/0.2 buffer over 25 minutes with a flow of 100 mL/min. The compounds were detected by UV at 270 nm. Pure fractions were lyophilized to afford (R)-3-(benzyloxy)-N-(3-(2-((2-fluoro-3-(methylsulfonyl)phenyl)amino)-5-methylpyrimidin-4-yl)-1H -indol-7-yl)-2-(4-methylpiperazin-1-yl)propanamide, Example 64 (161 mg, 32%) as a solid.

$^1$H NMR (500 MHz, DMSO-d$_6$) δ 2.15 (s, 3H), 2.26-2.44 (m, 7H), 2.59-2.69 (m, 2H), 2.71-2.82 (m, 2H), 3.25 (s, 3H), 3.58 (t, 1H), 3.79 (dd, 1H), 3.91 (dd, 1H), 4.54 (s, 2H), 6.98 (t, 1H), 7.24-7.36 (m, 5H), 7.40 (t, 1H), 7.44 (d, 1H), 7.52-7.58 (m, 1H), 8.01 (d, 1H), 8.14 (d, 1H), 8.26-8.33 (m, 2H), 9.17 (s, 1H), 9.83 (s, 1H), 11.21 (s, 1H). m/z (ES+), [M+H]$^+$=672.5.

Example 65

(S)-3-(benzyloxy)-N-(3-(2-((2-fluoro-3-(methylsulfonyl)phenyl)amino)-5-methylpyrimidin-4-yl)-1H-indol-7-yl)-2-(4-methylpiperazin-1-yl)propanamide The first eluting isomer from the reaction of Example 64, step 2 was collected and evaporated in vacuo. The residue was dissolved in acetonitrile/water and lyophilized to afford (S)-3-(benzyloxy)-N-(3-(2-((2-fluoro-3-(methylsulfonyl)phenyl)amino)-5-methylpyrimidin-4-yl)-1H -indol-7-yl)-2-(4-methylpiperazin-1-yl)propanamide Example 65 (63 mg, 12%) as a solid.

$^1$H NMR (500 MHz, DMSO-d$_6$) δ 2.15 (s, 3H), 2.27-2.44 (m, 7H), 2.59-2.69 (m, 2H), 2.72-2.82 (m, 2H), 3.25 (s, 3H), 3.58 (t, 1H), 3.79 (dd, 1H), 3.91 (dd, 1H), 4.54 (s, 2H), 6.98 (t, 1H), 7.24-7.37 (m, 5H), 7.40 (t, 1H), 7.44 (d, 1H), 7.51-7.58 (m, 1H), 8.01 (d, 1H), 8.14 (d, 1H), 8.26-8.33 (m, 2H), 9.17 (s, 1H), 9.83 (s, 1H), 11.21 (s, 1H). m/z (ES+), [M+H]$^+$=672.4.

Example 66

(R)-N-(3-(5-fluoro-2-(2-fluoro-3-(methylsulfonyl)phenylamino)pyrimidin-4-yl)-1H-indol-7-yl) -3-methoxy-2-(piperazin-1-yl)propanamide Step 1

Potassium carbonate (4.21 g, 30.45 mmol) was added to methyl 2-bromo-3-methoxypropanoate (3 g, 15.23 mmol) and tert-butyl piperazine-1-carboxylate (3.12 g, 16.75 mmol) in acetonitrile (60 mL) at 25° C. under air. The resulting mixture was stirred at room temperature for 15 hours. The reaction mixture was filtered through celite and the filter cake was washed with additional acetonitrile. The filtrate was combined and the solvent was removed under reduced pressure.The crude product was purified by flash alumina chromatography, elution gradient 0 to 100% EtOAc in petroleum ether. Pure fractions were evaporated to dryness to afford tert-butyl 4-(1,3-dimethoxy-1-oxopropan-2-yl)piperazine-1-carboxylate (2.300 g, 50.0%) as a colourless oil. m/z (ES+), [M+H]$^+$=303.

Step 2

Lithium hydroxide (0.238 g, 9.92 mmol) was added to a slurry of tert-butyl 4-(1,3-dimethoxy-1-oxopropan-2-yl)piperazine-1-carboxylate (1.0 g, 3.31 mmol) in a solvent mixture of MeOH (5 mL), THF (5.00 mL) and water (25 mL), then stirred at room temperature for 1 hour.The solvent was concentrated in vacuo to afford crude lithium 2-(4-(tert-butoxycarbonyl)piperazin-1-yl)-3-methoxypropanoate (1.200 g) as a yellow solid. m/z (ES+), [M+H]$^+$=289.

Step 3

2,4,6-tripropyl-1,3,5,2,4,6-trioxatriphosphinane (5398 mg, 9.99 mmol) was added to a solution of Intermediate 33 (415 mg, 1.00 mmol), lithium 2-(4-(tert-butoxycarbonyl)piperazin-1-yl)-3-methoxypropanoate (588 mg, 2.00 mmol) and DIPEA (1.745 mL, 9.99 mmol) in DCM (30 mL) at rt, then stirred at rt overnight. The reaction was diluted with water (100 mL), extracted with DCM (3×20 mL). The conmbined organic phases were washed with water (10 mL) and brine (10 mL), then dried with Na$_2$SO$_4$, filtered and concentrated in vacuo. The crude product was purified by preparative HPLC (XBridge Prep C18 OBD column, 5 μ silica, 19 mm diameter, 150 mm length), using decreasingly polar mixtures of water (containing 0.05% $NH_3$) and MeCN as eluents. Fractions containing the desired compound were evaporated to dryness to afford tert-butyl 4-(1-((3-(5-fluoro-2-((2-fluoro-3-(methylsulfonyl)phenyl)amino)pyrimidin-4-yl)-1H-indol -7-yl)amino)-3-methoxy-1-oxopropan-2-yl) piperazine-1-carboxylate (305 mg, 44.5%) as a yellow solid. m/z (ES+), $[M+H]^+$=686.

Step 4 tert-butyl 4-(1-((3-(5-fluoro-2-((2-fluoro-3-(methylsulfonyl)phenyl)amino)pyrimidin-4-yl)-1H indol-7-yl)amino)-3-methoxy-1-oxopropan-2-yl)piperazine-1-carboxylate (300 mg, 0.44 mmol) was added to a solution of 1:3 TFA-DCM (10 mL), then stirred at rt for 1h. The solvent was then concentrated in vacuo and the crude product was purified by preparative HPLC (XBridge Prep C18 OBD column, 5 μ silica, 19 mm diameter, 150 mm length), using decreasingly polar mixtures of water (containing 0.1% formic acid) and MeCN as eluents. Appropriate fractions were concentrated to dryness to afford N-(3-(5-fluoro-2-((2-fluoro-3-(methylsulfonyl)phenyl) amino)pyrimidin-4-yl)-1H-indol-7-yl)-3-methoxy-2-(piperazin-1-yl)propanamide (200 mg, 78%) as a yellow solid. The compounds were further purified by preparative chiral-HPLC on a chiralpak ID-3 column, eluting isocratically with 10% MeOH in MTBE (modified with 0.1% DEA) as eluent. The fractions containing the first eluting compound were concentrated to dryness to afford example 66, (R)-N-(3-(5-fluoro-2-(2-fluoro-3-(methylsulfonyl)phenylamino)pyrimidin-4-yl)-1H-indol-7-yl)-3-methoxy-2-(piperazin-1-yl)propanamide (39.0 mg, 19.43%) as a white solid.

$^1$H NMR (300 MHz, DMSO-$d_6$) δ 2.50 (s, 3H), 2.68-2.71 (m, 2H), 2.80-2.90 (m, 6H), 3.30 (s, 3H), 3.62-3.69 (m, 2H), 3.76-3.83 (m, 1H), 7.00-7.06 (t, 1H), 7.44-7.49 (t, 1H), 7.60-7.65 (m, 2H), 8.16-8.27 (m, 3H), 8.40-8.44 (m, 2H), 9.47 (s, 1H), 10.25 (s, 1H), 12.20 (s, 1H). m/z (ES+), $[M+H]^+$=586.

Example 67

The fractions of the second eluting isomer of Example 66 were concentrated to dryness to afford Example 67, (S)-N-(3-(5-fluoro-2-(2-fluoro-3-(methylsulfonyl)phenylamino) pyrimidin-4-yl) -1H-indol-7-yl)-3-methoxy-2-(piperazin-1-yl)propanamide (35.0 mg, 17.50%) as a white solid.

$^1$H NMR (300 MHz, DMSO-$d_6$) δ 2.50 (s, 3H), 2.73 (m, 2H), 2.83-2.92 (m, 6H), 3.30 (s, 3H), 3.64-3.69 (m, 2H), 3.76-3.82 (m, 1H), 7.00-7.06 (t, 1H), 7.44-7.49 (t, 1H), 7.60-7.65 (m, 2H), 8.16-8.27 (m, 3H), 8.41-8.44 (m, 2H), 9.47 (s, 1H), 10.30 (s, 1H), 12.29 (s, 1H). m/z (ES+), $[M+H]^+$=586.

Example 68: Enzyme Inhibition Studies

Enzyme inhibition studies were performed using recombinant JAK1 (amino acids 866-1154, Life Technologies, #PV4774, Carlsbad, CA), JAK2 (amino acids 831-1132, AstraZeneca R&D Boston), or JAK3 (amino acids 781-1124, AstraZeneca R&D Boston) under buffer conditions of 50 mM HEPES pH 7.3, 1 mM DTT, 0.01% Tween-20, 50 μg/ml BSA, and 10 mM $MgCl_2$. JAK enzyme was expressed as N-terminal GST fusion in insect cells and purified by glutathione-affinity and size-exclusion chromatographies. Enzymes were assayed at their approximated high end of physiological ATP concentration of 5 mM, in the presence of inhibitor dosed at 30, 3, 0.3, 0.03, 0.003 and 0 μM final test concentrations.

For JAK1, 4 nM of enzyme was incubated with 1.5 μM peptide substrate (FITC-C6-KKHTDDGYMPMSPGVA-NH2 (SEQ ID NO:1), Intonation, Boston, MA). For JAK2, 0.3 nM enzyme was incubated with 1.5 μM peptide substrate (5FAM-GEEPLYWSFPAKKK-NH2 (SEQ ID NO:2), Intonation, Boston, MA). For JAK3, 0.1 nM enzyme was incubated with 1.5 μM peptide substrate (5FAM-GEEPLYWSFPAKKK-NH2 (SEQ ID NO:2), Intonation, Boston, MA). Phosphorylated and unphosphorylated peptides were separated and quantified by a Caliper LC3000 system (Caliper Life Sciences, MA) for calculating percent inhibition. The results of this assay are shown in Table 24.

Example 69: Cellular interleukin induced JAK-STAT6-luciferase assay (pSTAT6)

A stable cell line based on U937 monocytes was generated that have a genomically incorporated luciferase reporter gene under control of the STATE promotor (U937-STAT6-Luc). The cells were grown in suspension in Growth medium (RPMI 1640 with GlutaMAX and 25 mM Hepes, 10% FCS, 1% Sodium, 1% Non-Essential amino acids and 0.5 mg/ml geneticin (for selection)) at 37° C. and 5% $CO_2$.

Cells were harvested by centrifugation at 250 g for 5 min and resuspended in Assay buffer (20 mM HEPES, 1×HBSS and 0.1% BSA) to 1000 cells pr μl. For stimulation of cells was used interleukin (IL-13) also dissolved in Assay buffer to 300 pM or 7 nM, respectively. This gives 150 pM and 3.5 nM, respectively in the final assay, inducing the signal to 80% of $E_{max}$. Test and control compounds were applied to assay plates (low vol white 384-well plates) in serial dilutions from 10 mM to 0.5 nM at 5 nl pr well in DMSO.

To each well was added 4 μl cells and 4 μl interleukin (IL-13) and the plates were sealed and incubated at 37° C. for 4½ h and then at room temperature for 30 min. The assay was developed by addition of 4 μl pr well of SteadyGlo (Promega) and after 20 min the plates were read at an Envision plate reader with luminescence filter.

In the assay the compounds were thus diluted 1600 fold and dose-response curves for inhibition of the interleukin induced signal determine the $IC_{50}$ for the compounds. The assay determined compounds in the $IC_{50}$ range from 2 nM to 2 relevant for the control and test compounds.

TABLE 24

| Example | pSTAT6 ($IC_{50}$, μM) | JAK1 ($IC_{50}$, μM) | JAK2 ($IC_{50}$, μM) | JAK3 ($IC_{50}$, μM) |
|---|---|---|---|---|
| Tofacitinib | 0.118 | 0.030 | 0.130 | 0.074 |
| Filgotinib | NA | 0.814 | 6.77 | >30 |
| ABT-494 (base) | NA | 0.005 | 0.064 | 0.864 |
| 1 | 0.041 | <0.003 | 1.58 | >30 |
| 2 | 0.032 | ≤0.003 | 7.35 | >30 |
| 3 | 0.039 | <0.003 | 4.12 | >30 |
| 4 | 0.027 | <0.003 | 1.60 | >30 |
| 5 | 0.029 | 0.0051 | 5.02 | >30 |
| 6 | 0.172 | 0.0574 | >30 | >30 |
| 7 | 0.057 | 0.0066 | 14.5 | >30 |
| 8 | 0.078 | 0.0245 | >30 | >30 |
| 9 | 0.055 | 0.0034 | 5.73 | >30 |
| 10 | 0.352 | 0.0398 | 21 | >30 |
| 11 | 0.085 | 0.0131 | 11.1 | >30 |
| 12 | >4.95 | 1.13 | >30 | >30 |
| 13 | 0.097 | 0.0224 | 26.1 | >30 |
| 14 | 0.021 | <0.003 | 2.43 | >30 |

TABLE 24-continued

| Example | pSTAT6 (IC$_{50}$, μM) | JAK1 (IC$_{50}$, μM) | JAK2 (IC$_{50}$, μM) | JAK3 (IC$_{50}$, μM) |
|---|---|---|---|---|
| 15 | 0.465 | 0.213 | >30 | >30 |
| 16 | 0.018 | <0.003 | 0.725 | >30 |
| 17 | 0.090 | 0.0036 | 4.86 | >30 |
| 18 | 1.280 | 0.403 | >30 | >30 |
| 19 | 0.423 | 0.143 | >30 | >30 |
| 20 | 0.051 | N/A | N/A | N/A |
| 21 | 2.23 | 0.986 | >30 | >30 |
| 22 | 0.029 | <0.003 | 2.56 | >30 |
| 23 | 0.866 | 0.183 | >30 | >30 |
| 24 | 0.042 | 0.0042 | 3.46 | >30 |
| 25 | 0.063 | 0.0228 | 6.59 | >30 |
| 26 | 0.038 | <0.003 | 0.456 | >30 |
| 27 | 0.041 | <0.003 | 0.162 | >30 |
| 28 | 0.147 | 0.0452 | 7.41 | >30 |
| 29 | 0.0399 | <0.003 | 1.20 | >30 |
| 30 | 0.072 | 0.0142 | 1.16 | >30 |
| 31 | 0.074 | 0.0064 | 1.79 | >30 |
| 32 | 0.933 | 0.482 | >30 | >30 |
| 33 | 0.055 | <0.003 | 1.93 | >30 |
| 34 | >4.20 | 1.84 | >30 | >30 |
| 35 | 0.034 | <0.003 | 1.22 | >30 |
| 36 | 0.167 | 0.0703 | >30 | >30 |
| 37 | 0.0269 | <0.003 | 0.968 | >30 |
| 38 | 0.0426 | 0.0033 | 6.87 | >30 |
| 39 | 0.446 | 0.256 | >30 | >30 |
| 40 | >6.25 | 3.28 | >30 | >30 |
| 41 | 0.058 | 0.00395 | 4.82 | >30 |
| 42 | 0.036 | <0.003 | 0.604 | >30 |
| 43 | 0.477 | 0.095 | >30 | >30 |
| 44 | 3.05 | 0.953 | >30 | >30 |
| 45 | 0.036 | <0.003 | 0.718 | >30 |
| 46 | 0.083 | 0.0198 | 17.8 | >30 |
| 47 | 0.619 | 0.180 | >30 | >30 |
| 48 | 0.082 | 0.003 | 8.230 | >30 |
| 49 | 0.093 | 0.013 | 12.3 | >30 |
| 50 | 0.362 | 0.0485 | >30 | >30 |
| 51 | 0.024 | <0.003 | 0.612 | >30 |
| 52 | 1.07 | 0.348 | >30 | >30 |
| 53 | 0.048 | <0.003 | 2.08 | >30 |
| 54 | 0.258 | 0.014 | 6.72 | >30 |
| 55 | 0.026 | <0.003 | 0.293 | >30 |
| 56 | 0.745 | 0.123 | >30 | >30 |
| 57 | 0.021 | <0.003 | 0.709 | >30 |
| 58 | 0.130 | 0.0486 | 25.3 | >30 |
| 59 | >6.25 | 0.145 | >30 | >30 |
| 60 | 0.0642 | 0.0074 | 11.9 | >30 |
| 61 | 0.163 | 0.0428 | >30 | >30 |
| 62 | 0.054 | <0.003 | 4.14 | >30 |
| 63 | 0.099 | NA | NA | NA |
| 64 | 0.026 | <0.03 | 0.910 | >30 |
| 65 | 0.508 | 0.073 | >30 | >30 |
| 66 | 0.051 | NA | NA | NA |
| 67 | 1.39 | NA | NA | NA |

Example 70-Alopecia Areata in vivo Dose Titration Study

A compound within the scope of the present disclosure was given orally to C3H/HeJ mice with established alopecia areata (AA) at increasing doses until clear hair growth was observed. Hair growth is expressed as Hair Index Score (HIS) evaluated on a weekly basis and compared to healthy mice (full fur=HIS of 300) and mice with complete AA (no fur=HIS of 0).

A. Animal Groups

Group 1-(n=6) alopecia areata mice treatment group
Group 2-(n=6) untreated alopecia areata mice (control group)
Group 3-(n=6) healthy controls B. Treatment All three groups were kept 6 by 6 in macrolon cages in a facility with 12 h/12 h light/dark cycle at 21±2° C. and with 55±15% relative humidity. Rodent chow and water was served ad libitum. Photographs were taken before initiation of the study and just before termination. Body weight (BW) and HIS were monitored once weekly. Once a day, Group 1 mice were served 5 g of grounded rodent chow soaked with the compound of example 35 in 10 mL of tap water at stepwise increased doses (BW and HIS was monitored once weekly):

1. 2 weeks at 0.5 mg/kg bodyweight (BW),
2. 2 weeks at 2.5 mg/kg BW, and
3. 2 weeks at 12.5 mg/kg BW.

C. Termination

At 1-2 h after the last dose at the highest concentration of the compound of Example 35, by which a clear hair growth had been observed and the hair growth score had been recorded, Group 1 mice were sacrificed. Blood was sampled from behind the eye in EDTA-coated test tubes (Multivette 300, Sarstedt) and kept on ice. Plasma was obtained by centrifugation (4° C., 4000G, 5 min) and 50 μL transferred to a 96-well NUNC plate and stored at −20° C. until analyzed with regards to drug concentration by LC-MSMS.

D. Results

Figure 2:
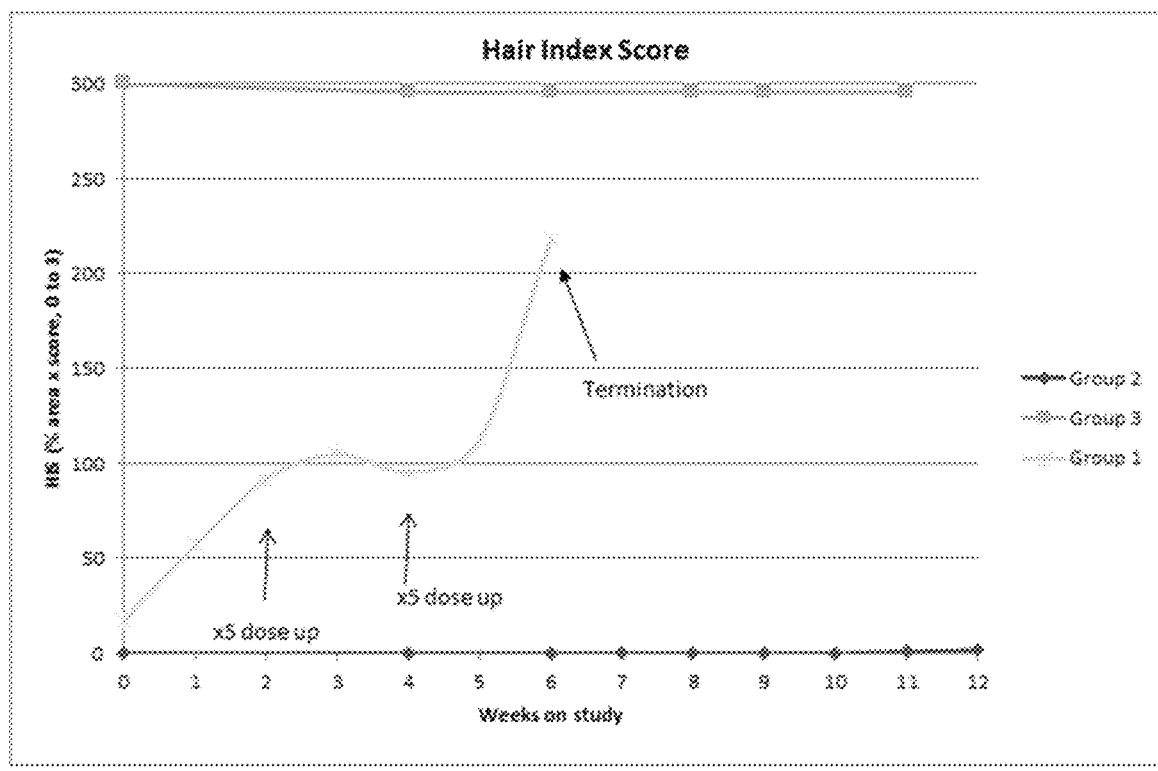
FIG. 2 illustrates the Hair Index Score (HIS) after treating C3H/HeJ mice with established alopecia areata with 0.5 mg/kg of the compound of Example 35 compared with untreated mice.

Results for all three groups are presented as a graph in FIG. 2, with HIS on the Y-axis and time (weeks) on the X-axis.

E. Results

The mean plasma exposure (total concentration) of compound of Example 35 at the time of termination was 338 nM, and the HIS=218.
The results indicate that:
1. The compound of Example 35 produced a desired response at the highest dose, although longer treatment is necessary to achieve HIS=300.
2. 12.5 mg/kg BW will be the preferred dose for a full experiment (12 weeks) demonstrating full effect (HIS=300).

Example 71-OVA Lung Inflammation Model in vivo Pharmacodynamic Properties Study

Brown Norway rats were sensitised and challenged with chicken ovary albumin (OVA). (Clinical and Experimental Allergy, 37 (2007) 973-988). After inhaling an amount of micronized compound within the scope of the present disclosure, the reduction in airway inflammation in the lung of OVA-challenged Brown Norway rat was measured as % reduction of eosinophils in broncho alveolar lavage (BAL) compared to challenged, but untreated rat using the following protocol. As the model control, an i.t. over dose (2*300 μg/kg) of the model reference compound, Budesonide, was used.

A. Animal groups 74 animals were divided into 8 experimental groups and treated as follows:

Group 1 (Saline/Saline/Air), n=6—Sham (saline) sensitisation at Day0 (S1) and Day7 (S2) and sham (saline) challenged at Day14 (P1). Treatment—room air Group 2 (OVA/Saline/Lactose), n=8—Sensitised at Day0 (S1) and Day7 (S2) with Al(OH)$_3$/OVA mixture followed by the i.t. sham (saline) challenge Day14 (P1). Treatment—DPI Lactose.

Group 3 (OVA/OVA/Lactose), n=12—Sensitised at Day0 (S1) and Day7 (S2) with Al(OH)$_3$/OVA mixture followed by the i.t. OVA challenge at Day14 (P1). Treatment—DPI Lactose.

Group 4 (OVA/OVA/Example 35), n=10—Sensitised at Day0 (S1) and Day7 (S2) with Al(OH)$_3$/OVA mixture followed by the i.t. OVA challenge at Day14 (P1). Treatment—DPI; Compound of Example 35, target dose 0.03 µ g/kg Group 5 (OVA/OVA/Example 35), n=10—Sensitised at Day0 (S1) and Day7 (S2) with Al(OH)$_3$/OVA mixture followed by the i.t. OVA challenge at Day14 (P1). Treatment—DPI; Compound of Example 35, target dose 0.3 µ g/kg Group 6 (OVA/OVA/Example 35), n=10—Sensitised at Day0 (S1) and Day7 (S2) with Al(OH)$_3$/OVA mixture followed by the i.t. OVA challenge at Day14 (P1). Treatment—DPI; Compound of Example 35, target dose 3 µ g/kg Group 7 (OVA/OVA/Example 35), n=10—Sensitised at Day0 (S1) and Day7 (S2) with Al(OH)$_3$/OVA mixture followed by the i.t. OVA challenge at Day14 (P1). Treatment—DPI; Compound of Example 35, target dose 30 µ g/kg Group 8 (OVA/OVA/Budesonide), n=8—Sensitised at Day0 (S1) and Day7 (S2) with Al(OH)$_3$/OVA mixture followed by the i.t. OVA challenge at Day14 (P1). Treatment—i.t. with Budesonide (model reference compound) at 2×300 µ g/kg Day 14. Twice daily.

B. Experimental Procedure

Prior to start of first sensitisation (S1), the body weight (BW) was recorded and all rats were tail marked with the identification number. The BW was additionally recorded prior to S2 and prior to the termination point (D15). All of the animals' BAL was determined. At the time of termination, the performer(s) (investigator) were blinded to the status of the individual rats, i. Sensitisation

The rats where subcutaneously (s.c.) injected with a mixture of OVA/Al(OH)$_3$ (100 µg OVA: 100 mg Alum in 1 ml saline/rat), and intraperitoneally (i.p.) injected with 0.5 ml/rat of *B. Pertussis* toxin (0.1 µg/ml) at Day 0 and Day 7. Sham sensitisation was performed by s.c. and i.p. injections of isotonic saline with the same volume and strategy.

ii. Administration of compounds

Dry Powder Inhalation (DPI) operating procedure

Each exposure system consisted of a flow-past exposure inhalation chamber, rat restraining tubes and a Modified Wright Dust Feed mechanism. Measurements of the aerosol concentration in the inhalation chamber for each dose level was performed by filter sampling at one of the inhalation ports (AP40, 47 mm, Millipore). Different doses of the compound of Example 35 was achieved by varying the exposure time whilst keeping the concentrations of the test article and flow in the exposure chambers constant. Rats from Group 2 and 3 were exposed to lactose in the restraining tube (Battelle chambers). Target inhaled doses (µg/kg) were calculated assuming exposure duration of 2-10 minutes and a body weight of 250 g using the following formula:

$$\text{Dose(mg/kg/day)} = \frac{C \times RMV \times D}{BW \times 1000}$$

Where C=Aerosol concentration (µg/L). RMV: Respiratory minute volume (L/min)=4.19×BW (g) 0.66/1000 (McMahon 1977) D=Duration of exposure. BW Body weight (kg).

Based on filter analysis results, the lung burden (lung dose) can be calculated according to the formula: Lung dose=Inhaled dose*fraction deposited in lung Intratracheal administration of the model reference compound (Budesonide)

The rats were weighed the day prior to OVA challenge. At challenge the rats were anaesthetised with Isoflurane mixture (air and 4% isoflurane) put in supine position with 30-40° angle and instilled with vehicle or compound. This intra-tracheal instillation was performed by using a modified metal cannula with bolus-bulb on the end. Rats were placed in cages in a supine position with a head up until regaining consciousness. The reference compound was administered twice daily with the second daily administration 6 hours post the first daily administration. Instillation volume: 0.25 mL/rat.

iii. Challenge (Provocation with OVA)

Five minutes (5') before OVA challenge, blood was collected (0.2 ml) from the tongue vein and plasma (60 ul/well) was collected on 96-deepwell plate. The provocation occurred at Day14 (P1) and was applied 2 hours after compound administration. The rats were anaesthetized with Isoflurane mixture (air and 4% isoflurane) put in supine position with 30-40° angle and instilled with the isotonic saline or OVA (0.1 mg/ml). The intra-tracheal instillation was performed by using a modified metal cannula with bolus-bulb on the end. Rats were placed in cages in a supine position with a head up until regaining consciousness. Sham challenge was performed by i.t. instillation of isotonic saline with the same volume and strategy. Instillation volume: 0.25 ml/rat iv. Termination and Broncho-Alveolar Lavage

At 22 hours post OVA challenge (P1), rats were euthanized with an intraperitoneal injection of 1 ml pentobarbital (50 mg/ml). Blood was be taken from v. jugularis in EDTA coated tubes, centrifuged (Rotanta 46R, 480 xg, 10 min, 20° C.) and plasma samples will be collected on 2×96-deepwell plates (60 ul/well) placed on dry-ice and stored at minimum −70° C. for the further analysis. Broncheo-alveolar lavage (BAL) was performed by manual perfusion of the whole lung with PBS. After the trachea is exposed, a polyethylene tube (PE120) was inserted and ligated with suture. The tube was connected to a syringe, prefilled with 4.2 ml of PBS at room temperature, slowly injected into the lung, with 10 second duration in the lung. The fluid was recollected by slow aspiration into the syringe. This procedure was performed twice. The final BAL fluid was transferred to a test tube (4 ml, polypropylene (PP)). Tubes with BAL samples were weighed (assuming that 1ml of BALF is equal to 1 g). The BAL was kept on ice until centrifugation (Rotanta 46R, 300 xg, 10 min, 4° C.). After centrifugation the supernatant was divided on 4×96-well plates (0.1 ml/well) placed on dry-ice, saved and stored in at min. −70° C. until analysis of mediators. The cell pellet was then re-suspended in 0.5 ml of PBS and kept on ice until cell counting. The total and differential number of cells was counted using a semi -automated SYSMEX XT-1800i Vet (Sysmex, Kobe Japan) with the gated program: BALrOVAi.

C. Results

Based on filter analysis, the following lung doses (µg/kg bodyweight) of micronized example 35 were achieved:
Group 4: 0.08
Group 5: 0.11
Group 6: 0.6
Group 7: 4.76

Figure 3:
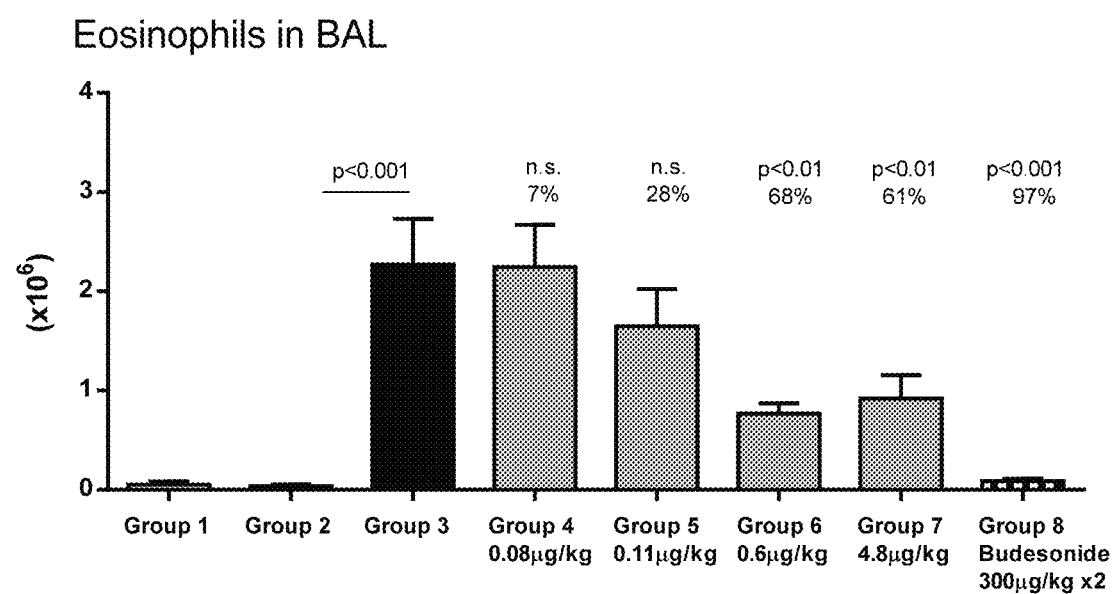
FIG. 3 illustrates the percent reduction of eosinophils in broncho alveolar lavage in OVA challenged Brown Norway rats after treatment with the compound of Example 35 compared to challenged, but untreated rats.

Results are presented as bar graphs with p-values above, alternatively n.s. indicating not significant, and % reduction of eosinophils as compared to the non-treated group 3 (OVA/OVA) of each experimental group in FIG. 3.

The results indicate that:

1. The compound of Example 35 reduced the eosinophils in BAL by 7, (not significant), 28 (not significant), 68 ($p<0.01$) and 61 ($p<0.01$) % at the lung doses of 0.08, 0.11, 0.6 and 4.76 µg/kg respectively.

2. OVA provocation (Group 3) significantly increased the number of eosinophils in BAL.

3. Compound of Example 35 significantly reduced presence of eosinophils in a dose dependent way with a max inhibition of 68% compared to OVA control (group 3), and that an inhibition plateau is observed from the 0.6 µg/kg dose.

4. Model reference compound Budesonide at the over dose 2*300 mg/kg (Group 8) showed a 97% inhibition of eosinophils, in a range observed for this model.

The invention claimed is:

1. A method of treating a JAK1-related disorder in a subject comprising administering a therapeutically effective amount of the compound (R)-N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide, or a pharmaceutically acceptable salt thereof.

2. The method of claim 1, wherein the JAK1-related disorder is chosen from Type 1 diabetes, lupus, multiple sclerosis, rheumatoid arthritis, psoriasis, asthma, atopic dermatitis, autoimmune thyroid disorders, ulcerative colitis, Crohn's disease, COPD, vitiligo, and alopecia areata.

3. The method of claim 2, wherein the JAK1-related disorder is asthma.

4. A method of treating a JAK1-related disorder in a subject comprising administering a pharmaceutical composition which includes: a therapeutically effective amount of the compound (R)-N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide, or a pharmaceutically acceptable salt thereof; and a pharmaceutically acceptable diluent, excipient, or carrier.

5. The method of claim 4, wherein the JAK1-related disorder is chosen from Type 1 diabetes, lupus, multiple sclerosis, rheumatoid arthritis, psoriasis, asthma, atopic dermatitis, autoimmune thyroid disorders, ulcerative colitis, Crohn's disease, COPD, vitiligo, and alopecia areata.

6. The method of claim 5, wherein the JAK1-related disorder is asthma.

7. A method of treating a JAK1-related disorder in a subject comprising administering a therapeutically effective amount of the compound (R)-N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide.

8. The method of claim 7, wherein the JAK1-related disorder is chosen from Type 1 diabetes, lupus, multiple sclerosis, rheumatoid arthritis, psoriasis, asthma, atopic dermatitis, autoimmune thyroid disorders, ulcerative colitis, Crohn's disease, COPD, vitiligo, and alopecia areata.

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: JAK kinases peptide substrates

<400> SEQUENCE: 1

Lys Lys His Thr Asp Asp Gly Tyr Met Pro Met Ser Pro Gly Val Ala
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: JAK kinases peptide substrates

<400> SEQUENCE: 2

Gly Glu Glu Pro Leu Tyr Trp Ser Phe Pro Ala Lys Lys Lys
1               5                   10
```

9. The method of claim 8, wherein the JAK1-related disorder is asthma.

10. A method of treating a JAK1-related disorder in a subject comprising administering a pharmaceutical composition which includes: a therapeutically effective amount of the compound (R)-N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide; and a pharmaceutically acceptable diluent, excipient, or carrier.

11. The method of claim 10, wherein the JAK1-related disorder is chosen from Type 1 diabetes, lupus, multiple sclerosis, rheumatoid arthritis, psoriasis, asthma, atopic dermatitis, autoimmune thyroid disorders, ulcerative colitis, Crohn's disease, COPD, vitiligo, and alopecia areata.

12. The method of claim 11, wherein the JAK1-related disorder is asthma.

13. A method of treating a JAK1-related disorder in a subject comprising administering a therapeutically effective amount of a pharmaceutically acceptable salt of the compound (R)-N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide.

14. The method of claim 13, wherein the JAK1-related disorder is chosen from Type 1 diabetes, lupus, multiple sclerosis, rheumatoid arthritis, psoriasis, asthma, atopic dermatitis, autoimmune thyroid disorders, ulcerative colitis, Crohn's disease, COPD, vitiligo, and alopecia areata.

15. The method of claim 14, wherein the JAK1-related disorder is asthma.

16. A method of treating a JAK1-related disorder in a subject comprising administering a pharmaceutical composition which includes: a therapeutically effective amount of a pharmaceutically acceptable salt of the compound (R)-N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide; and a pharmaceutically acceptable diluent, excipient, or carrier.

17. The method of claim 16, wherein the JAK1-related disorder is chosen from Type 1 diabetes, lupus, multiple sclerosis, rheumatoid arthritis, psoriasis, asthma, atopic dermatitis, autoimmune thyroid disorders, ulcerative colitis, Crohn's disease, COPD, vitiligo, and alopecia areata.

18. The method of claim 17, wherein the JAK1-related disorder is asthma.

19. The method of claim 2, wherein the JAK1-related disorder is COPD.

20. The method of claim 5, wherein the JAK1-related disorder is COPD.

21. The method of claim 8, wherein the JAK1-related disorder is COPD.

22. The method of claim 11, wherein the JAK1-related disorder is COPD.

23. The method of claim 14, wherein the JAK1-related disorder is COPD.

24. The method of claim 17, wherein the JAK1-related disorder is COPD.

* * * * *